United States Patent
Forsell

(10) Patent No.: US 11,963,876 B1
(45) Date of Patent: *Apr. 23, 2024

(54) HIP JOINT METHOD

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 16 days.

This patent is subject to a terminal disclaimer.

(21) Appl. No.: 16/898,524

(22) Filed: Jun. 11, 2020

Related U.S. Application Data

(63) Continuation of application No. 13/383,004, filed as application No. PCT/SE2010/050812 on Jul. 12, 2010, now Pat. No. 10,682,234.

(Continued)

(30) Foreign Application Priority Data

| Jul. 10, 2009 | (SE) | 0900957-2 |
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |
| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |

(Continued)

(51) Int. Cl.
*A61F 2/36* (2006.01)
*A61B 17/16* (2006.01)
(Continued)

(52) U.S. Cl.
CPC ........ *A61F 2/3603* (2013.01); *A61B 17/1617* (2013.01); *A61B 17/1631* (2013.01);
(Continued)

(58) Field of Classification Search
CPC ...... A61F 2/3603; A61F 2/30756; A61F 2/34; A61F 2/36
See application file for complete search history.

(56) References Cited

U.S. PATENT DOCUMENTS

| 8,945,233 B2 * | 2/2015 | Forsell | A61F 2/4603 606/86 R |
| 10,195,037 B2 * | 2/2019 | Forsell | A61F 2/3603 |

(Continued)

*Primary Examiner* — Bruce E Snow

(57) ABSTRACT

A method of treating a hip joint of a human patient is disclosed. The method comprises the steps of: inserting a needle or a tube like instrument into the patient's body, using the needle or tube like instrument to fill a part of the patient's body with gas and thereby expanding a cavity within said body, placing at least two laparoscopic/arthroscopic trocars in said cavity, inserting a camera through one of the laparoscopic/arthroscopic trocars into said cavity, inserting at least one dissecting tool through one of said at least two laparoscopic/arthroscopic trocars, dissecting an area of the pelvic bone on the opposite side from the acetabulum, creating a hole in said dissected area, said hole passing through the pelvic bone and into said hip joint of the patient, and providing said medical device to the hip joint, through said hole in the pelvic bone of the patient.

19 Claims, 63 Drawing Sheets

Related U.S. Application Data

(60) Provisional application No. 61/229,738, filed on Jul. 30, 2009, provisional application No. 61/229,796, filed on Jul. 30, 2009, provisional application No. 61/229,735, filed on Jul. 30, 2009, provisional application No. 61/229,789, filed on Jul. 30, 2009, provisional application No. 61/229,786, filed on Jul. 30, 2009, provisional application No. 61/229,778, filed on Jul. 30, 2009, provisional application No. 61/229,767, filed on Jul. 30, 2009, provisional application No. 61/229,761, filed on Jul. 30, 2009, provisional application No. 61/229,755, filed on Jul. 30, 2009, provisional application No. 61/229,752, filed on Jul. 30, 2009, provisional application No. 61/229,751, filed on Jul. 30, 2009, provisional application No. 61/229,748, filed on Jul. 30, 2009, provisional application No. 61/229,747, filed on Jul. 30, 2009, provisional application No. 61/229,746, filed on Jul. 30, 2009, provisional application No. 61/229,745, filed on Jul. 30, 2009, provisional application No. 61/229,743, filed on Jul. 30, 2009, provisional application No. 61/229,739, filed on Jul. 30, 2009.

(30) Foreign Application Priority Data

| | | |
|---|---|---|
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.
| | |
|---|---|
| *A61B 17/56* | (2006.01) |
| *A61F 2/30* | (2006.01) |
| *A61F 2/32* | (2006.01) |
| *A61F 2/34* | (2006.01) |
| A61B 17/00 | (2006.01) |
| A61B 17/84 | (2006.01) |

(52) U.S. Cl.
CPC ........ *A61B 17/1668* (2013.01); *A61B 17/562* (2013.01); *A61F 2/30756* (2013.01); *A61F 2/34* (2013.01); *A61F 2/36* (2013.01); *A61B 17/00234* (2013.01); *A61B 17/1666* (2013.01); *A61B 17/84* (2013.01); *A61F 2002/30469* (2013.01); *A61F 2002/30471* (2013.01); *A61F 2002/30495* (2013.01); *A61F 2002/305* (2013.01); *A61F 2002/30558* (2013.01); *A61F 2002/30565* (2013.01); *A61F 2002/30579* (2013.01); *A61F 2002/30594* (2013.01); *A61F 2002/30604* (2013.01); *A61F 2002/30616* (2013.01); *A61F 2002/30757* (2013.01); *A61F 2002/3233* (2013.01); *A61F 2002/3241* (2013.01)

(56) References Cited

U.S. PATENT DOCUMENTS

| | | | |
|---|---|---|---|
| 11,234,713 B2* | 2/2022 | Forsell | A61F 2/34 |
| 11,351,040 B2* | 6/2022 | Forsell | A61B 17/3474 |
| 2009/0043344 A1* | 2/2009 | Schlotterback | A61F 2/30756 |
| | | | 604/509 |

\* cited by examiner

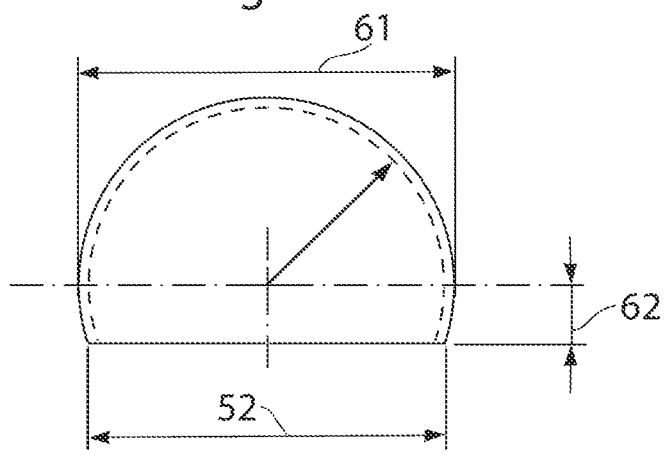
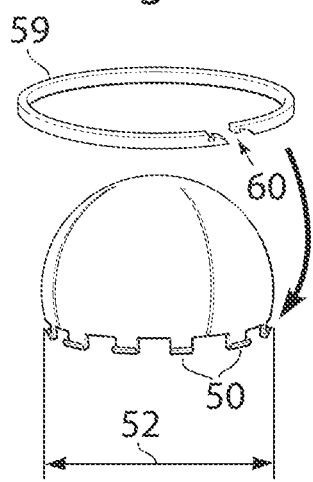
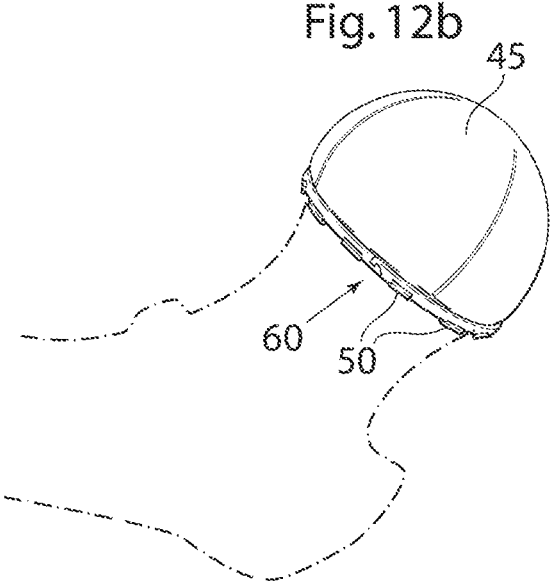

Fig. 13
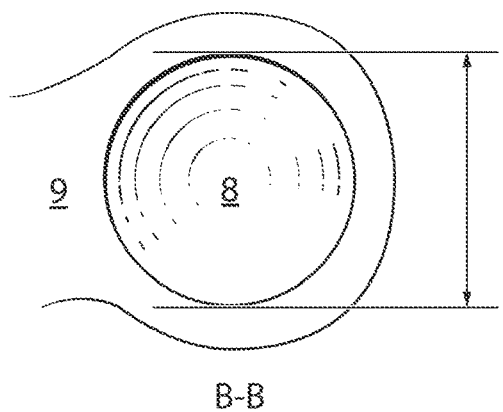
B-B
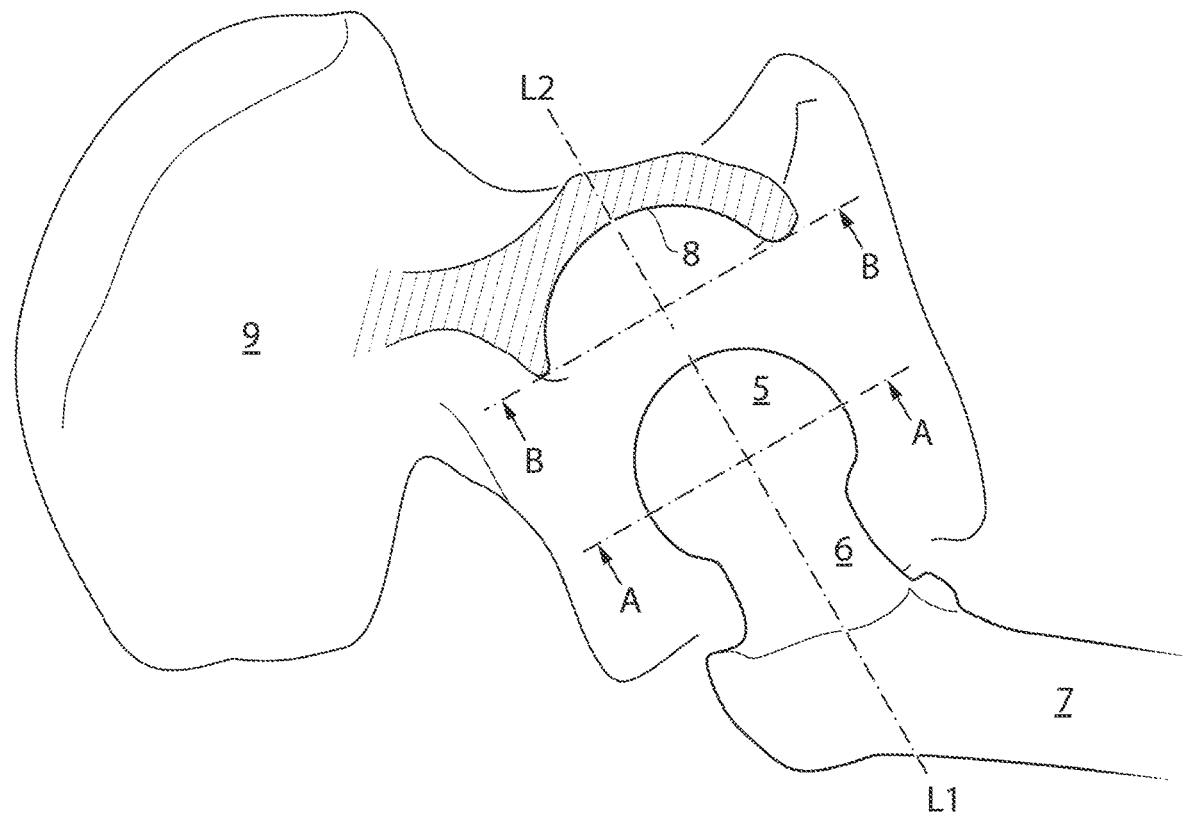
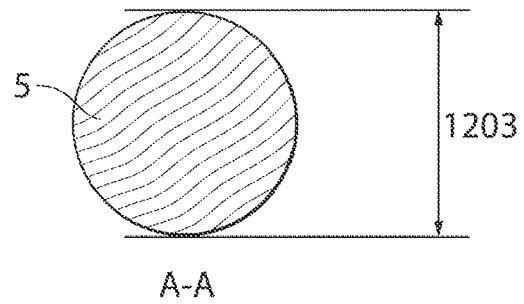
A-A

Fig. 16a
Fig. 16b
Fig. 16c
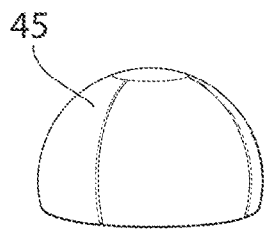
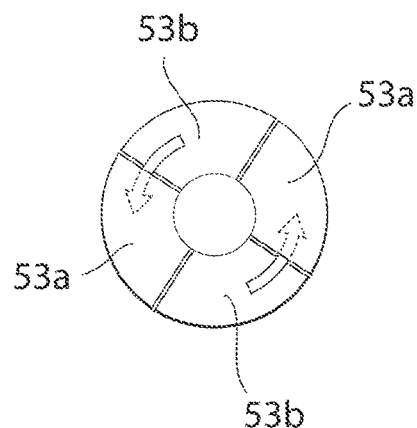
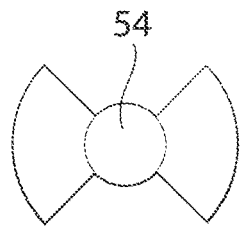
Fig. 16d
Fig. 16e
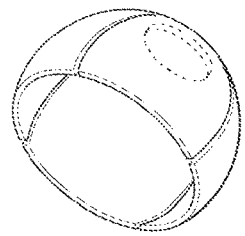
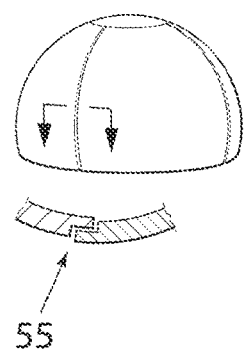
Fig. 17a
Fig. 17b
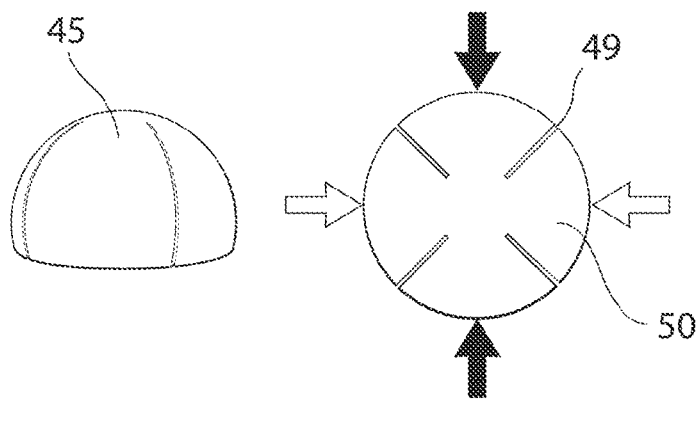
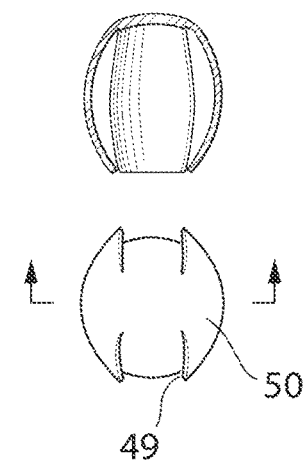

Fig. 20
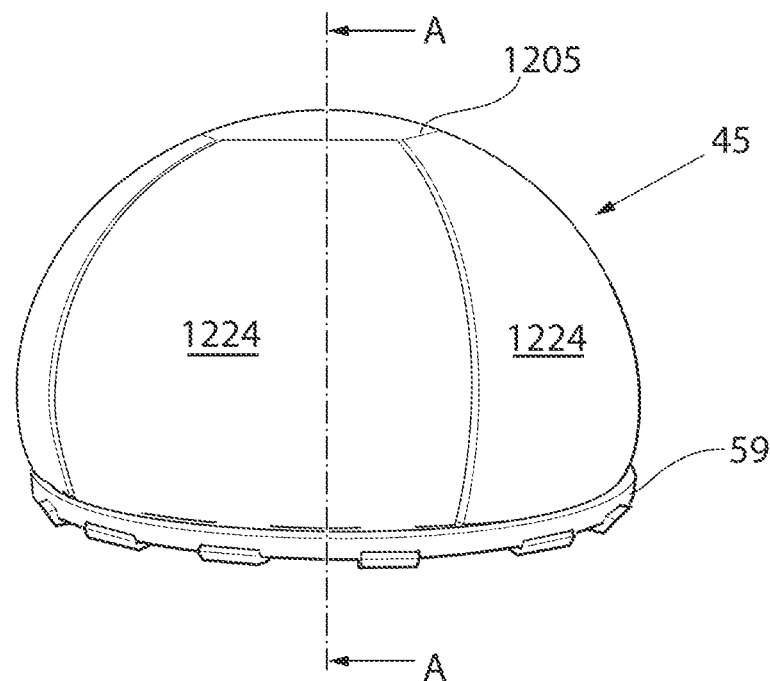
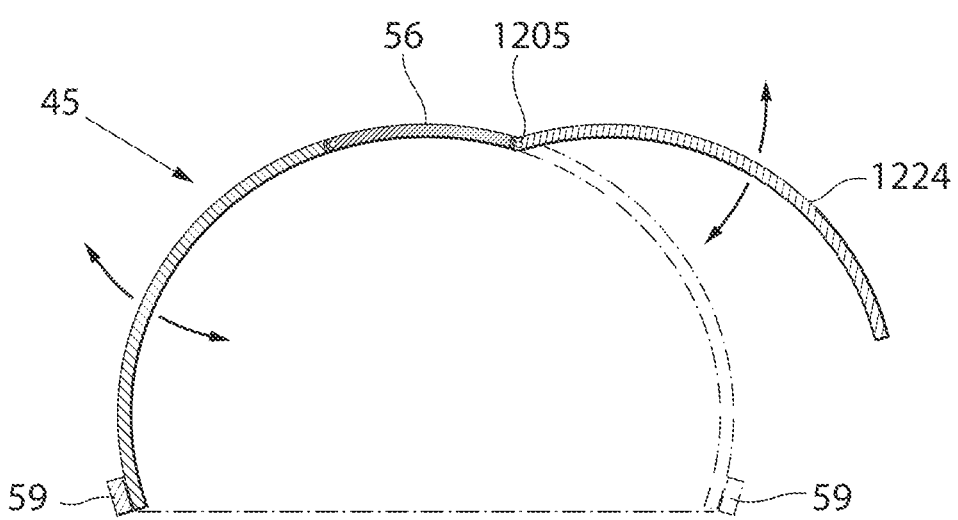
A-A

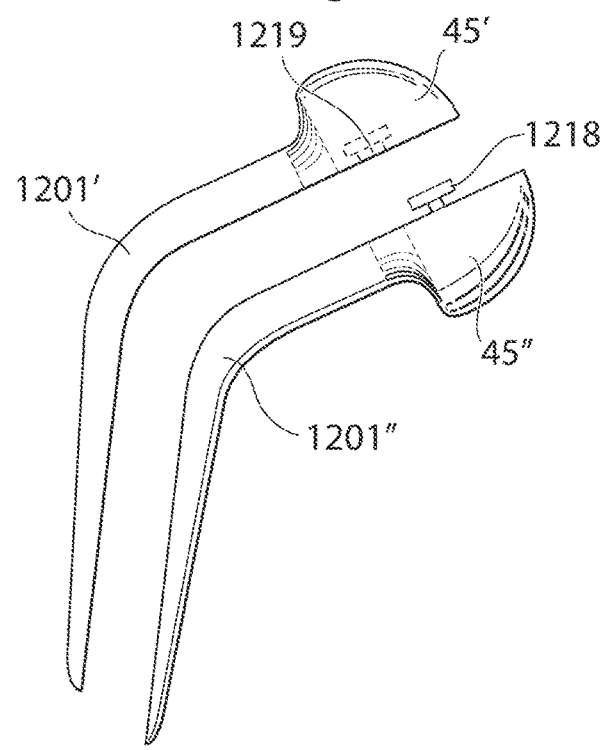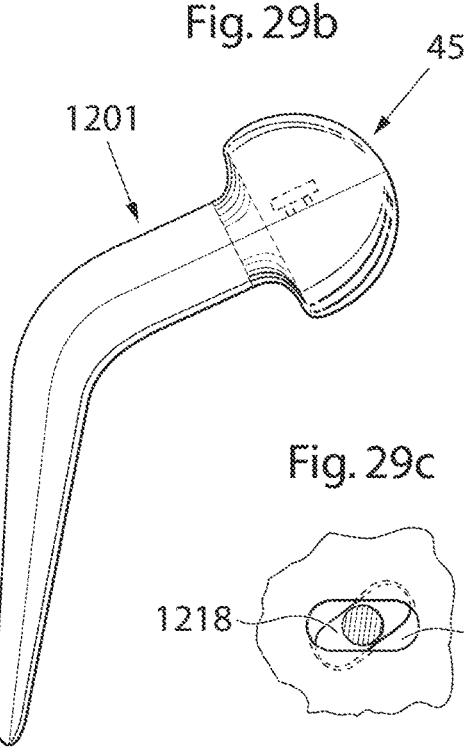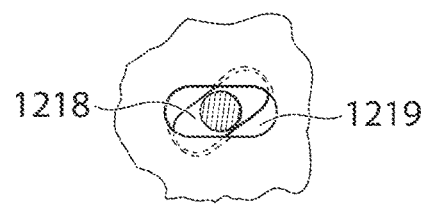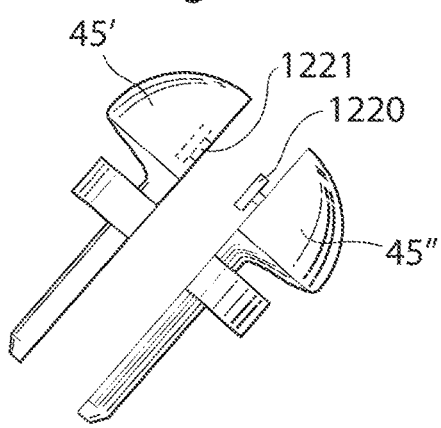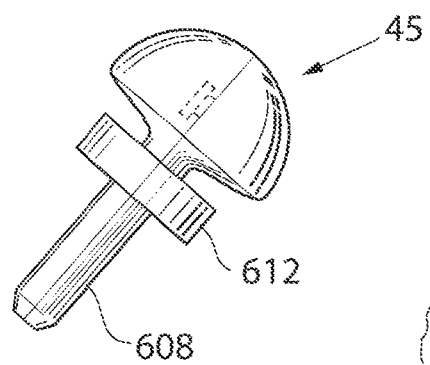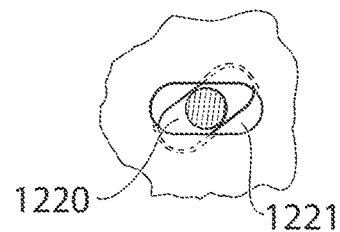

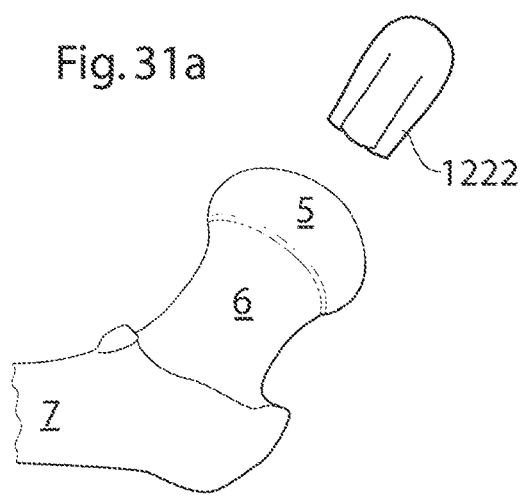
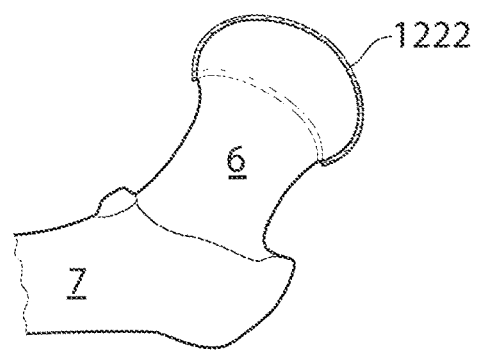
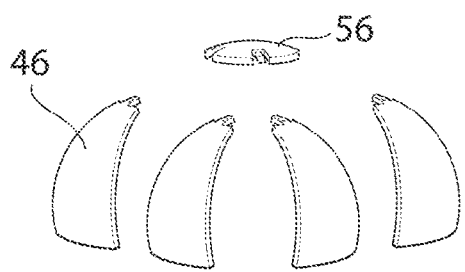
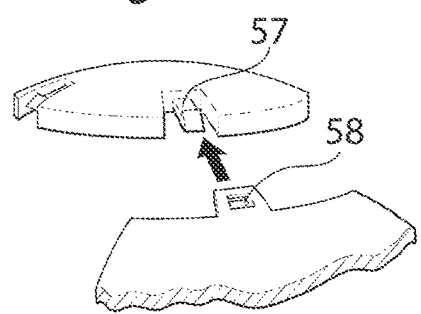
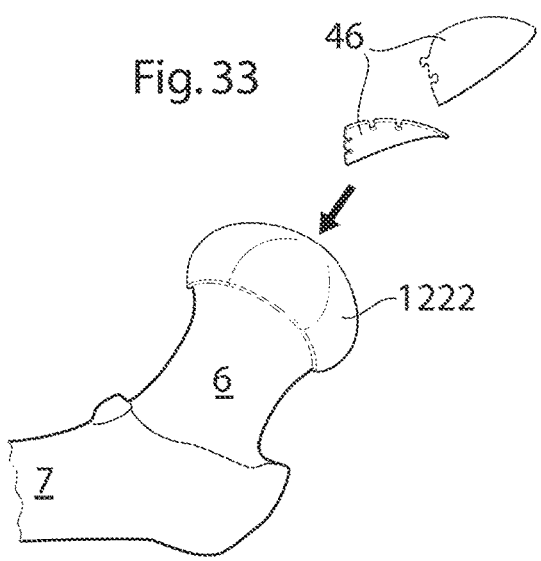
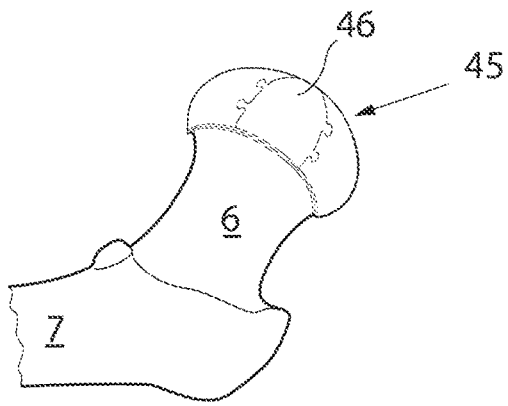

Fig. 79
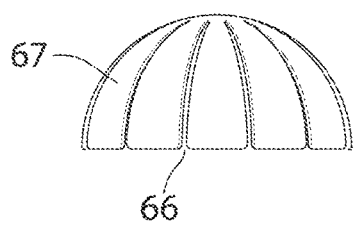
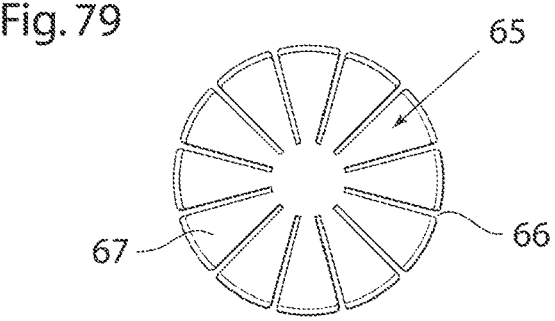
Fig. 80a
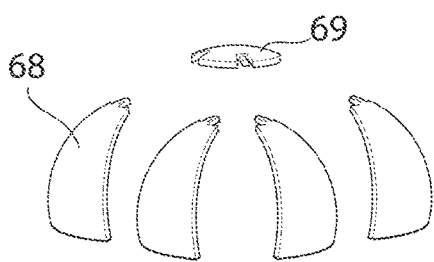
Fig. 80b
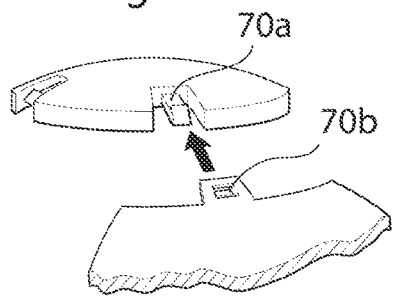
Fig. 80c
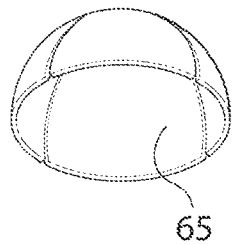
Fig. 81a
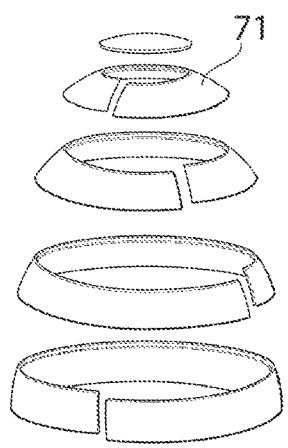
Fig. 81b
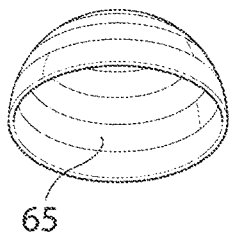
Fig. 81c
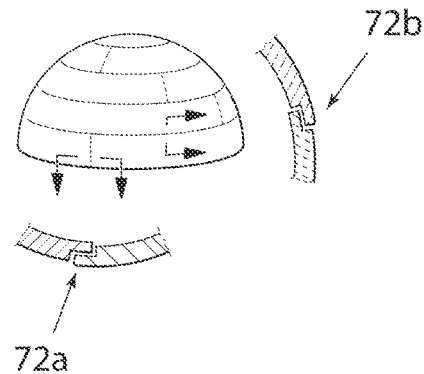

HIP JOINT METHOD

This application is a continuation of U.S. application Ser. No. 13/383,004, filed Jan. 9, 2012, now U.S. Pat. No. 10,682,234, which is the National Stage Entry of PCT/SE2010/050812, which claims the benefit of Provisional Application Nos. 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735, 61/229,738, all filed Jul. 30, 2009, and Priority from Swedish Application Nos. 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2, 0900981-2, all filed Jul. 10, 2009, the entire contents of each application is hereby incorporated by reference in this application.

FIELD OF INVENTION

The present invention relates generally to a medical device for implantation in a hip joint, and a method of providing said medical device.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is usually done through a lateral incision in the hip and upper thigh and through, Fascia Lata and the lateral muscles of the thigh. To get access to the hip joint, the supporting hip joint capsule attached to Femur and Ilium of Pelvis needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

SUMMARY

A medical device for implantation in a hip joint for providing at least one artificial hip joint surface for a patient is provided. The hip joint has two hip joint surfaces; caput femur, a ball shaped proximal part of the femoral bone, and acetabulum, a bowl shaped part of the pelvic bone adapted to hold said caput femur, wherein said medical device comprises at least one partly ball or bowl shaped artificial hip joint surface adapted to replace at least one hip joint surface in a functional hip joint, wherein said medical device has: a largest diameter, largest radius or a largest cross-sectional distance, and an opening, wherein said opening, has a smallest diameter or a smallest radius or a smallest functional opening. The medical device is adapted to have a variable size of said smallest diameter or smallest radius or said smallest functional opening of said opening, and a variable size of said largest diameter, largest radius or a largest cross-sectional distance, such that said medical device can be inserted through a hole having a diameter smaller than said largest diameter or cross-sectional distance of said medical device. This enabling a less invasive surgical procedure which could spare the hip joint capsule and reduce the removal of healthy Femoral bone.

In one embodiment said variable smallest diameter or smallest functional opening in said opening is adapted to be changed during an operation to place said artificial hip joint surface in a functional position in said hip joint.

In another embodiment a medical device for treating hip joint osteoarthritis by providing at least one hip joint surface for a human patient is provided. The medical device comprises at least one hip joint surface having one convex and one opposite concave side being hollow, said device has a largest diameter or largest radius or a largest cross-sectional distance, and an opening with a smallest diameter or a smallest functional opening, said smallest diameter or cross sectional distance is adapted to be changed during an operation.

According to a first embodiment the medical device is adapted to provide an artificial caput femur surface, and according to a second embodiment the medical device is adapted to provide an artificial acetabulum surface.

According to another embodiment the artificial hip joint surface comprises at least one artificial caput femur surface, and the artificial caput femur surface displays a partly spherical shape being hollow, and through its shape being adapted to mechanically fixate said artificial caput femur surface to said caput femur by at least partly surrounding said caput femur beyond a maximum diameter of said caput femur.

According to yet another embodiment the medical device comprises an artificial caput femur surface. The artificial caput femur surface is further adapted to have the diameter or functional opening of said opening being larger than the diameter of the caput femur, when introduced onto the caput femur. Furthermore it is adapted to have said diameter or functional opening of said opening being smaller than the caput femur or said greatest internal cross-sectional diameter, after the mounting of said artificial caput femur surface on the caput femur, thus the opening of the artificial caput femur surface is variable and adapted to either expand during the mounting onto caput femur or decrease in size after being mounted onto the caput femur. The mechanical construction to allow such variable opening could be made in many different ways. Preferable a locking member or self locking construction could be used to fix the position in a functional hip joint. A few examples of such a variable construction are outlined further down.

Furthermore an artificial acetabulum surface could be supplied. This acetabulum surface may also be variable. Thus the opening of the artificial acetabulum surface is variable and adapted to either expand during the mounting onto caput femur or a artificial replacement therefore or decrease in size after being mounted onto said caput femur or said artificial replacement therefore. The mechanical construction to allow such variable opening could be made in many different ways. A few examples of such a variable construction are outlined further down.

According to one embodiment a locking member or self locking construction could be used to fixate the position in a functional hip joint. The artificial acetabulum surface could be mounted on the caput femur or said artificial replacement therefore to withhold hip joint dislocations up until a threshold up until which broken bones are avoided, therefore the artificial acetabulum surface is mounted on the caput femur or said artificial replacement therefore until a certain predetermined pressure cause dislocation of the hip joint.

According to another embodiment the artificial acetabulum surface displays a partly inner side spherical shape being hollow, and through its shape being adapted to mechanically fixate said artificial acetabulum surface to the caput femur or an artificial replacement therefore by at least partly surrounding the caput femur or an artificial replacement therefore beyond a maximum diameter of the caput femur or an artificial replacement therefore. Only a pressure equal to or larger than said predetermined pressure applied to the hip joint will dislocate said mechanical fixation.

In one embodiment, the caput femur which is integrated with the collum femur, said hollow partly ball shaped artificial hip joint surface is adapted to be placed onto said caput femur, said caput femur preferable surgically modified, to replace the surface of the caput femur in a functional hip joint, wherein said opening is adapted to be directed towards the collum femur, wherein said smallest diameter or smallest functional opening in said opening is smaller than said largest diameter or a largest radius inside the hollow part of said artificial hip joint surface, when said artificial surface being placed onto the caput femur in a functional hip joint, wherein the size of said smallest diameter or smallest functional opening in said opening is adapted to be variable.

In a second embodiment, said hollow partly bowl shaped artificial hip joint surface is adapted to replace the acetabulum, the acetabulum preferable surgically modified, to replace the surface of the acetabulum in a functional hip joint, wherein said opening is adapted to be directed towards the caput femur or an artificial replacement for the caput femur, wherein said smallest diameter or smallest functional opening in said opening is smaller than said largest diameter or a largest radius inside the hollow part of said artificial hip joint surface, when said artificial surface is placed onto the caput femur in a functional hip joint, wherein the size of the smallest diameter or smallest functional opening in said opening is adapted to be variable.

In both said first and said second embodiment said variable smallest diameter or smallest functional opening in said opening is adapted to be changed during an operation to place said artificial hip joint surface in a functional position in said hip joint.

In another embodiment said medical device comprises at least an artificial caput femur surface adapted to replace at least a surface of said caput femur, wherein said artificial acetabulum surface is movable pre-mounted onto said at least artificial caput femur surface, wherein said at least an artificial caput femur surface having a largest outer diameter, wherein said artificial acetabulum surface having said smallest diameter or smallest functional opening in said opening smaller than said largest outer diameter of said at least an artificial caput femur surface, when movable pre-mounted on said artificial caput surface, wherein said moveable pre-mounted placement is adapted to withhold a predetermined pressure applied onto said hip joint without dislocating and wherein said smallest diameter or smallest functional opening in said opening of said artificial acetabulum surface is adapted to be increased in size, to a size equal or larger than said largest outer diameter of said caput femur to be able to dislocate, when said predetermined pressure or a higher pressure is applied to said hip joint.

In another further embodiment said at least an artificial caput femur surface, comprise a replacement of the whole caput femur. In another embodiment said at least one artificial caput femur surface comprises a hollow ball shape replacement of the surface of the caput femur.

In another embodiment the size of said smallest diameter or smallest functional opening in said opening is smaller than the caput femur and adapted to be increased in size, to a size at least equal to the size of the caput femur during the placement of said artificial hip joint surface onto the caput femur.

In another embodiment the size of said smallest diameter or smallest functional opening in said opening is equal to, or larger than, the caput femur and adapted to be decreased in size, to a size smaller than the caput femur after the placement of said artificial hip joint surface onto the caput femur.

The medical device may further comprise a locking member, wherein said artificial hip joint surface is further adapted to, have said smallest diameter or smallest functional opening of said opening locked in its final position in said functional hip joint, by said locking member.

Said locking member may be adapted to lock by passing into a hole passing through the femoral bone, following said cross-sectional diameter. Said locking member may also comprise a circular structure adapted to lock by preventing an expansion of the diameter or cross sectional distance of said opening.

Construction

To enable the opening to be expandable, according to one example, the medical device could further comprise at least one slit. It is also conceivable that the medical device comprises at least one elastic member or at least one elastic part, is severable in at least one place or comprises at least two parts. In the embodiment where the medical device comprises at least two parts, the at least two parts could be adapted to mechanically connect using at least one of the following: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. It is further more conceivable that at least one of said at least to parts is a part adapted to serve as base part to which at least one additional part can be connected. This base part could be adapted to be located in the center in relation to said at least one additional part.

According to one embodiment the medical device is larger than equator frustum spherical.

According to one embodiment the medical device comprises two parts rotatably connected to each other, wherein said medical device has a first state adapted for the insertion in the hip joint through a hole, and a second state adapted to enable the artificial caput femur surface to function as caput femur surface, said medical device is further adapted to alter between said first and second state by means of said rotatable connection.

According to a third embodiment the medical device comprises multiple ring shaped objects, said multiple ring shaped objects being adapted to connect to each other after insertion in a hip joint to form an artificial acetabulum surface.

Insertion

For insertion into a hip joint it is conceivable that the medical device comprises at least one elastic member for varying the largest diameter, which enables the insertion through a hole, wherein said hole has a diameter smaller than said largest diameter of said medical device.

According to one embodiment the medical device is adapted to pass through said hole placed in the pelvic bone, the femoral bone or the hip joint capsule.

For insertion, the medical device, according to one embodiment, comprises at least one movable member for varying the largest diameter of the medical device for insertion through said hole, wherein said hole has a diameter smaller than the largest diameter of the medical device. It is furthermore conceivable that the medical device comprises two parts for insertion through said hole. The parts could be adapted to be inserted through a hole in the pelvic bone from the opposite side from acetabulum of a human patient, said hole having a diameter less than the largest diameter of said assembled medical device.

In the embodiment where the medical device comprises at least two hip joint surface parts, the parts could be adapted to be at least partly connected or moved in relation to each other after insertion in a hip joint of a human patient to form an artificial hip joint surface.

The insertion of the at least two artificial hip joint surface parts, according to any of the embodiments, could be performed using manual manipulation or an instrument adapted therefore. The surgical instrument could further comprise a bend comprising at least one of the following: A fixed angle, an adjustable angle, or a parallel displaced part or section.

Fixation

According to a preferred embodiment the fixation is performed without the use of any element penetrating the cortex of caput femur, the femoral bone or the pelvic bone. However, in other embodiments a fixation could go through any of the bones. For example the variable opening of the artificial caput femur surface may be fixated by a cross sectional connection passing through caput femur.

According to one embodiment the opening adapted to be changed is changed during and or after the mounting on said caput femur or an artificial replacement therefore. In one embodiment the opening is smaller than said maximum caput femur diameter when said medical device is mounted on said caput femur or an artificial replacement therefore in said functional position, and larger than said maximum caput femur diameter when said opening travels over said caput femur or an artificial replacement therefore.

According to one embodiment the medical device is adapted to be fixated to a caput femur or an artificial replacement therefore, a femoral bone or a pelvic bone by means of said elastic member exerting a squeezing force on said caput femur or an artificial replacement therefore, said femoral bone or said pelvic bone.

According to one embodiment of the medical device, the opening of said medical device has a normal state diameter, wherein the diameter of said opening is smaller than said normal state diameter when said medical device is inserted into said hip joint, and wherein said diameter of said opening is larger than said normal state diameter when said opening travels over said caput femur or an artificial replacement therefore.

According to one embodiment the medical device is fully adapted to enable the mounting of said medical device on said caput femur or an artificial replacement therefore.

According to one embodiment the medical device the medical device comprises a mechanical shape adapted to enable the mounting of said medical device on the caput femur or an artificial replacement therefore.

According to one embodiment the medical device comprises at least one slit adapted to enable the mounting of said medical device on the caput femur or an artificial replacement therefore.

According to one embodiment the medical device comprises at least one part made of elastic material adapted to enable the mounting of said medical device on said caput femur or an artificial replacement therefore.

According to one embodiment the medical device, at least one part of said device is bent in a way that it is adapted to enable the mounting of said medical device in said hip joint.

To fixate the medical device to the caput femur, an artificial replacement therefore or the pelvic bone, at lest one of the following could be used: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. All embodiments above, when applicable, may apply to said artificial caput femur surface as well as said acetabulum surface or both of them.

The medical device according to any of the embodiments could have the size of the largest diameter, largest radius or a largest cross-sectional distance being variable such that the medical device can be introduced through a hole having a cross sectional area smaller than 530 mm2 or smaller than 380 mm2 or smaller than 250 mm2 or smaller than 180 mm2 or smaller than 110 mm2.

Material

The medical device according to any of the embodiments could comprise at least one of the materials: polyethylene based material, PTFE, Corian, titanium, stainless steel, wolfram, other metal material, a combination of metal material, carbon fiber, boron, a combination of metal and plastic materials, a combination of metal and carbon based material, a combination of carbon and plastic based material, multi-material, wherein one material comprise a flexible material, multi-material, wherein one material comprise an elastic material, multi-material, wherein one material comprising more parts than the other at least one material, PE, an acrylic polymer or a zirconium ceramic material. It is also conceivable that the medical device comprises a self lubricating material. In cases where the medical device do not comprise a self lubricating material or if the self lubricating material is not sufficient it is conceivable that the medical device is adapted to be lubricated after insertion in said hip joint.

Beyond Part and Functional Opening

In yet another embodiment a medical device for treating hip joint osteoarthritis is supplied, the hip joint having a collum femur, having a first axial substantially circular distribution leading to a substantially rounded shape caput femur, wherein said collum femur is placed distal to the caput femur, a center axis of the collum and caput femur in line with the first axial distribution being the caput femur center axis, wherein the caput femur has a substantially ball shaped configuration proximal of the collum femur, with an outer maximum radius perpendicular to the caput femur center axis, the caput femur being placed in a bowl shaped acetabulum, having an opening, wherein the bowl shaped acetabulum has a second axial distribution with an acetabulum center axis from the center of the bottom of the acetabulum bowl and following the center of the bowl towards the center of the opening of the bowl, towards the caput femur, wherein the acetabulum bowl has an inner maximum radius perpendicular to the acetabulum center axis, wherein the caput femur center axis is in line/aligned with the acetabulum center axis, in a special centered position, when the caput femur is placed; aligned, centered and symmetrical in the acetabulum bowl in the hip joint, the aligned center axis is defined as the hip joint center axis, wherein the caput femur and the acetabulum has one hip joint surface each, placed towards and contacting each other, wherein the hip joint surfaces carrying weight in the hip joint are the weight carrying surfaces, wherein the outer maximum radius of the caput femur is forming a circular extending, maximum caput femur radius circle, extending perpendicular to the hip joint center axis, defining a maximum caput femur radius cross-section perpendicular to the hip joint center axis, wherein said medical device comprises at least one artificial hip joint surface, adapted to at least partly replace at least one of the hip joint surfaces, said artificial hip joint surface at least partly being hollow and having an inner and outer surface, wherein said artificial hip joint surface has an artificial hip joint surface center axis aligned with the hip joint center axis when the hip joint is placed in the special centered position, when at least one of said artificial hip joint surfaces is implanted in the hip joint, with the caput femur or an artificial caput femur surface placed; aligned, centered and symmetrical in the acetabulum bowl or an artificial acetabulum surface in the hip joint, wherein said medical device comprises a central part and a surrounding part, the central part being aligned with the artificial hip joint surface center axis and the surrounding part surrounding the surface of the caput femur or an artificial caput femur surface not including the central part, wherein the caput femur or an artificial caput femur surface, has a maximum caput femur radius cross-section, in which the outer maximum radius of the caput femur or said artificial caput femur surface is forming a circular extending maximum caput femur or artificial caput femur radius circle, extending perpendicular to the hip joint center axis, defining the maximum caput femur radius cross-section perpendicular to the hip joint center axis or perpendicular to said artificial hip joint surface center axis, when the hip joint is placed in said special centered position, wherein the surrounding part of said at least one artificial hip joint surface comprises at least one first beyond part of the artificial hip joint surface for extending in distal direction at least partly beyond the maximum caput femur radius cross-section, when the hip joint is placed in said special centered position, when at least one of the artificial hip joint surfaces is implanted in the hip joint, wherein said at least one first beyond part is adapted to have a closest perpendicular distance to said artificial hip joint surface center axis, being smaller than an inner maximum distance, extending perpendicularly from said artificial hip joint surface center axis to said inner surface of said artificial hip joint surface, when the hip joint is placed in the above mentioned special centered position and said artificial hip joint surface is placed in a functional position in the hip joint, thus adapted to create and creating a more stable position of said artificial hip joint surface, wherein said artificial hip joint surface is adapted to have said closest perpendicular distance variable, the distance between said at least one beyond part and the artificial hip joint surface center axis, wherein said closest perpendicular distance is adapted to vary between the placing phase, when said artificial hip joint surface is under placement in the hip joint, and the functional in place phase, when the at least one artificial hip joint surface is mounted in place in a functional position in the hip joint, wherein said closest perpendicular distance, between said at least one beyond part and the artificial hip joint surface center axis, is adapted to hinder the movement of the caput femur or artificial caput femur surface to dislocate out from the their functional position in the hip joint, when the at least one artificial hip joint surface is implanted in the functional position in the hip joint, wherein the artificial hip joint surface with it's beyond parts defines a functional opening, adapted to; with a first defined functional opening hinder the dislocation movement of the caput femur or artificial caput femur surface, when the at least one artificial hip joint surface is mounted in the functional position in the hip joint, and with a second defined functional opening, being different from said first functional opening, the caput femur or artificial caput femur is allowed to be placed with the hip joint surfaces attached and mounted together in the hip joint.

The medical device may have said variable closest perpendicular distance in said functional opening is adapted to be changed during an operation to place said artificial hip joint surface in a functional position in said hip joint.

The caput femur may be integrated with collum femur, wherein said hollow partly ball shaped artificial hip joint surface is adapted to be placed onto the caput femur, the caput femur preferable being surgically modified, to replace the surface of the caput femur in a functional hip joint, wherein said functional opening is adapted to be directed towards the collum femur, wherein said closest perpendicular distance in said functional opening is smaller than said largest radius or distance, extending perpendicular from the artificial hip joint center axis to the inside of the hollow part of said artificial hip joint surface, when said artificial surface being placed onto the caput femur in a functional hip joint, in the special centered position, wherein the size of said closest perpendicular distance in said functional opening is adapted to be variable.

The medical device may have said variable closest perpendicular distance in said functional opening is adapted to be changed during an operation to place said artificial caput femur surface in a functional position in said hip joint.

The medical device may have said hollow partly bowl shaped artificial hip joint surface adapted to replace said acetabulum, said acetabulum preferable surgically modified, to replace the surface of the acetabulum in a functional hip joint, wherein said functional opening is adapted to be directed towards the caput femur or an artificial replacement for the caput femur, wherein said closest perpendicular distance in said functional opening is smaller than said largest distance from the artificial hip joint center axis, to the inside of the hollow part of said artificial hip joint surface, perpendicular to said artificial hip joint center axis, when the hip joint is placed in the special centered position, when said artificial surface being placed onto the caput femur in a functional hip joint, wherein the size of said closest perpendicular distance in said functional opening is adapted to be variable.

The medical device may have said variable closest perpendicular distance in said functional opening adapted to be changed during an operation to place said artificial acetabulum surface in a functional position in said hip joint.

The medical device is in one embodiment, comprising at least one artificial caput femur surface adapted to replace at least a surface of the caput femur, wherein said artificial acetabulum surface is movably pre-mounted onto said at least one artificial caput femur surface, wherein said at least one artificial caput femur surface having a largest outer diameter, wherein said artificial acetabulum surface having said closest perpendicular distance in said functional opening smaller than said largest outer radius of said at least one artificial caput femur surface, when movable pre-mounted on said artificial caput femur surface, wherein said moveable pre-mounted placement is adapted to withhold a predetermined pressure applied onto said hip joint without dislocating and wherein said closest perpendicular distance in said functional opening of said artificial acetabulum surface is adapted to be increased in size, to a size equal to, or larger than said largest outer radius of said caput femur to be able to dislocate, when said predetermined pressure or a higher pressure is applied to the hip joint.

Said at least one artificial caput femur surface, may comprise a replacement of the entire caput femur.

Said at least one artificial caput femur surface, may comprises a hollow ball shape replacement of the surface of the caput femur.

In one embodiment the medical device have the size of said functional opening smaller than the caput femur and adapted to be increased in size, to a size at least equal to the size of the caput femur during the placement of said artificial hip joint surface onto the caput femur.

In another embodiment the medical device have the size of said functional opening is equal to or larger than the caput femur and adapted to be decreased in size, to a size smaller than the caput femur after the placement of said artificial hip joint surface onto the caput femur.

In another embodiment the medical device with said artificial caput femur surface displays a partly spherical shape being hollow, and through its shape being adapted to mechanically fixate said artificial caput femur surface to the caput femur by at least partly surrounding said caput femur beyond a maximum diameter of the caput femur.

In another embodiment the medical device with said artificial acetabulum surface displays a partly spherical shape being hollow, and through its shape being adapted to mechanically fixate to said caput femur or an artificial caput femur or an artificial caput femur surface by at least partly surrounding the caput femur, artificial caput femur or artificial caput femur surface beyond a maximum diameter thereof.

Said artificial caput femur surface may further be adapted to have the diameter of said functional opening being equal or larger than the diameter of the caput femur, when introduced onto the caput femur.

Said artificial caput femur surface may further be adapted to, have the smallest diameter of said functional opening being smaller than said greatest internal cross-sectional diameter, after the mounting of said artificial caput femur surface on the caput femur.

Said artificial caput femur surface may further be adapted to have said closest perpendicular distance of said functional opening being smaller than the caput femur, after the mounting of said artificial caput femur surface on the caput femur.

Said artificial acetabulum surface may further be adapted to have said closest perpendicular distance of said functional opening being equal or larger than the largest outer diameter of the caput femur or an artificial caput femur or an artificial caput femur surface, when said artificial acetabulum surface is introduced thereon.

Said artificial acetabulum surface may further be adapted to, have said closest perpendicular distance of said functional opening being smaller than the largest outer diameter of the caput femur, artificial caput femur or artificial caput femur surface, after said artificial acetabulum surface has been introduced and placed thereon.

The medical device for treating hip joint osteoarthritis according to any embodiment may comprise a locking member, wherein said artificial hip joint surface is further adapted to have said closest perpendicular distance of said functional opening locked in its final position in said functional hip joint, by said locking member.

Said locking member may be adapted to lock by passing into a hole passing through the femoral bone, following said cross-sectional distance.

Said locking member often comprises a circular structure adapted to lock by preventing an expansion of the diameter or cross sectional distance of said functional opening.

The Surgical and Laparoscopic/Arthroscopic Method

A second object is to provide a surgical and laparoscopic/arthroscopic method for treating a hip joint of a human patient by providing the medical device according to any of the embodiments. The hip joint comprises a caput femur located on the very top of the femoral bone and an acetabulum, which is a part of the pelvic bone, the caput femur is in connection with the acetabulum.

The idea is to perform an operation in the hip joint through a hole in the pelvic bone, however some of the aspects of the present invention can be performed using conventional surgery entering the hip joint through the hip joint capsule, or by entering through the femoral bone.

The surgical method comprises the steps of cutting the skin of the human patient, dissecting an area of the pelvic bone on the opposite side from acetabulum, creating a hole in the dissected area which passes through the pelvic bone and into the hip joint, and providing at least one hip joint surface into the hip joint, through the hole in the pelvic bone. The hip joint surface could comprise the medical device according to any of the embodiments above.

According to one embodiment, the step of cutting the skin of the human patient could be performed in the abdominal wall, the inguinal area, the pelvic region or the abdominal region of the patient.

The laparoscopic/arthroscopic method of the present invention comprises the steps of inserting a needle or a tube like instrument into the abdominal region, pelvic region or inguinal region of the patient's body, using the needle or tube like instrument to fill the patient's body with gas, placing at least two laparoscopic/arthroscopic trocars in the patient's body, and inserting a camera through one of the laparoscopic/arthroscopic trocars into the patient's body. At least one dissecting tool is inserted through one of said at least two laparoscopic/arthroscopic trocars after which an area of the pelvic bone on the opposite side from said acetabulum is dissected. Furthermore the method comprises the steps of creating a hole in said dissected area that passes through the pelvic bone and into the hip joint of the human patient, and providing at least one hip joint surface to the hip joint, through the hole in the pelvic bone. The hip joint surface could comprise the medical device according to any of the embodiments above.

According to one embodiment, the step of inserting a needle or tube like instrument is performed in the abdominal wall, the inguinal area, the pelvic region or the abdominal region of the patient.

The step of dissecting an area of the pelvic bone performed in both the surgical and the laparoscopic/arthroscopic method could be performed in the abdominal cavity, an area between peritoneum and the pelvic bone, an area of the pelvic bone and surrounding tissue, the pelvic area or an area of the pelvic bone that comprises the inguinal area. Dissecting a combination of the above mentioned areas is also conceivable.

Further Steps of the Operation

The surgical or laparoscopic/arthroscopic method could further comprise the step of reaming the caput femur and/or the acetabulum, e.g. by means of an expandable reamer.

According to one embodiment the artificial hip joint surface could be fixated to the pelvic bone or to the caput femur after the step of providing said hip joint surface. The fixation could be done by means of mechanical fixating members, such as screws or plates, adhesive, bone cement, or a combination thereof. When the artificial hip joint surface has been placed in the hip joint, the surgical or laparoscopic/arthroscopic method could further comprise the step of closing the hole in the pelvic bone using a bone plug, a prosthetic part, bone cement, or a combination thereof.

According to another embodiment the artificial hip joint surface is provided by means of a mould placed in the hip joint through a hole in the pelvic bone, the hip joint capsule or the femoral bone. Said artificial hip joint surface could comprise an artificial acetabulum surface and/or an artificial caput femur surface. After the mould has been inserted into the hip joint a fluid is injected which serves as an artificial caput femur surface after hardening. It is conceivable that said mould is resorbable by the human body or made of a material adapted to melt.

According to one embodiment the artificial hip joint surface is provided by injecting a fluid into a sealed area of the hip joint. Said artificial hip joint surface could comprise an artificial acetabulum surface and/or an artificial caput femur surface or the surface of acetabulum and/or the surface of caput femur. The sealed area is sealed by means of at least one sealing member placed in said hip joint through a hole in the pelvic bone, the hip joint capsule or the femoral bone. It is conceivable that said at lest one sealing member is resorbable by the human body or made of a material adapted to melt. A second sealing member may be used to seal the injecting member.

After the steps of the surgical method have been performed, the instruments are withdrawn and the skin is closed using sutures or staples.

Acetabulum Surfaces

According to one embodiment, the surgical or laparoscopic/arthroscopic method comprises the step of providing an artificial acetabulum surface connecting with the pelvic bone, and carrying the load placed on said caput femur from the weight of said patient by the connection with said pelvic bone. It is conceivable that the diameter of the hole is larger than the largest diameter of the artificial acetabulum surface thus allowing the artificial acetabulum surface to pass through the hole in its entirety, however it is also conceivable that said hole is smaller than the largest diameter of the artificial acetabulum surface thus hindering the artificial acetabulum surface from passing through the hole, which makes it possible for the edges of said hole to carry the load placed on said acetabulum from the weight of the patient.

According to a first embodiment the artificial acetabulum surface could comprise at least one supporting member which in turn could comprise at least one screw, adhesive, at least one plate, bone cement, a section of the artificial acetabulum surface or a combination of the mentioned alternatives. It is also conceivable that the supporting member comprises a first and second part. The second part is displaceable in relation to the first part and adapted to carry a load by the connection with the pelvic bone, and carries the load when displaced.

According to a second embodiment the artificial acetabulum surface comprises at least two acetabulum surface parts. The at least two artificial acetabulum surface parts are adapted to be connected to each other after insertion in a hip joint of a human patient to form an artificial acetabulum surface. The two artificial caput femur surface parts could be adapted to be mechanically connected using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. The artificial acetabulum being severable enables the insertion of the artificial acetabulum surface through a hole smaller than the artificial acetabulum surface, which makes it possible for the edges of said hole to carry the load placed on said acetabulum from the weight of the patient. The surgical or laparoscopic/arthroscopic method could comprise the steps of inserting said parts through said hole into the hip joint of a human patient, mounting said parts together or moving said parts in relation to each other after insertion in the hip joint and thereby forming an artificial acetabulum surface.

According to another embodiment the artificial acetabulum surface could be adapted to have a varying largest diameter for insertion through a hole in the pelvic bone from the opposite side from acetabulum. Since the largest diameter of the artificial acetabulum surface is adapted to vary between being both smaller and larger than the hole in the pelvic bone, the hole could having a diameter smaller than the largest diameter of the artificial acetabulum surface.

The surgical or laparoscopic/arthroscopic method could comprise the step of inserting the artificial acetabulum surface adapted to have a varying largest diameter through the hole in the pelvic bone. In this embodiment it is conceivable that the artificial acetabulum surface is adapted to be flexible in its construction, thus enabling the insertion of said artificial acetabulum surface through a hole in the pelvic bone that is smaller than said largest diameter of the artificial acetabulum surface. The flexible part of the artificial acetabulum surface could further be adapted to expand after insertion through the hole making the largest diameter of the artificial acetabulum surface larger than the diameter of the hole in the pelvic bone, thus hindering the artificial acetabulum surface from passing through the hole.

According to one embodiment the surgical or laparoscopic/arthroscopic method comprises using an artificial acetabulum surface having at least one first size related to an insertion through a hole, a first hole being smaller than said first size artificial acetabulum surface do not allow passage of the artificial acetabulum surface through said hole. The artificial acetabulum surface is adapted to vary said first size, for allowing insertion through said first hole in the pelvic bone from the opposite side from acetabulum of said human patient, said artificial acetabulum surface is adapted to change said first size to at least one second size, being smaller than said first hole for allowing said insertion through said first hole of said artificial acetabulum surface, including the method step of: Varying the size of the artificial acetabulum surface between being both smaller and larger than said first hole in the pelvic bone.

According to yet another embodiment the artificial acetabulum surface is created using a mould or a sealed area possible to use as mould. The method could further comprise the step of injecting a fluid into said mould or sealed area, the fluid serves as an artificial acetabulum surface when it hardens.

The mould or sealing members could be made of a resorbable material and be placed in the hip joint through at least one of the hip joint capsule, the pelvic bone, or the femoral bone. The mould or sealing members could be placed in the hip joint using manual manipulation or an instrument adapted therefore.

The surgical or laparoscopic/arthroscopic method could comprise the step of reaming said acetabulum or said caput femur, in which case the reamer could be expandable for reaming an area larger than the hole through which the reamer is inserted.

The step of creating a hole in the pelvic bone could be performed using an instrument comprising a driving member, a bone contacting organ in connection with said driving member, an operating device adapted to operate said driving member. The bone contacting organ is adapted to create a hole in the acetabulum area starting from the abdominal side of the pelvic bone of said human patient through repetitive or continuous movement. The surgical instrument could further comprise a bend comprising at least one of the following: a fixed angle, an adjustable angle, or a parallel displaced part or section. The bone contacting organ of the surgical instrument could further be adapted to be replaceable to a bone contacting organ adapted to ream at least one of said acetabulum and said caput femur.

The surgical or laparoscopic/arthroscopic method could further comprise the step of placing an artificial acetabulum surface onto caput femur or an artificial caput femur surface and, when mounted in the joint, acting as an acetabulum bowl. Said artificial acetabulum surface having an axial distribution and centre axis from the concave bottom thereof up until the centre of the opening holding caput femur or said artificial caput femur surface, having a substantially bowl shaped configuration with a maximum inner diameter of said artificial acetabulum surface substantially perpendicular to the centre axis of said axial distribution.

The artificial acetabulum surface, comprises at least one first beyond part adapted to cover the bone of the caput femur or said artificial caput femur surface, on at least a part of said caput femur or said artificial caput femur surface, beyond the maximum inner diameter of said artificial acetabulum surface, away from the concave bottom of said acetabulum bowl, when mounted on said caput femur or an artificial caput femur surface in its functional position in the joint. The at least one first beyond part have a closest perpendicular distance to said centre axis, which is smaller than the distance between the periphery of said maximum inner diameter of said artificial acetabulum surface and said centre axis. The method further comprises the step of mounting said artificial acetabulum surface, including the first beyond part thereof, on the caput femur or said artificial caput femur surface in said functional position. This creates a more stable position of said artificial acetabulum surface. Preferable holding said artificial acetabulum surface in place until a certain predetermined pressure will dislocate it. Said predetermined pressure defined to both avoiding any broken bone or lose artificial hip joint surface and also avoiding unnecessary dislocations in between the joint surfaces.

Caput Femur Surface

The surgical or laparoscopic/arthroscopic method could further comprise the step of placing an artificial caput femur surface onto caput femur on the opposite side of collum femur and, when mounted in the joint, in said acetabulum bowl or an artificial replacement therefore. Said collum femur having an axial distribution leading to said caput femur having a substantially ball shaped configuration with a maximum diameter substantially perpendicular to the centre axis of the prolongation of said axial distribution of said collum femur, said caput femur or said artificial caput femur surface being normally placed in an acetabulum bowl or an artificial replacement therefore creating said hip joint.

The artificial caput femur surface, comprises at least one first beyond part of said artificial caput femur surface adapted to cover and/or go into the bone of the caput femur on at least a part of said caput femur beyond the maximum diameter of said caput femur, away from said acetabulum bowl towards said collum femur, when mounted on said caput femur in its functional position in the joint. The at least one first beyond part have a closest perpendicular distance to said centre axis, which is smaller than the distance between the periphery of said maximum diameter of said caput femur and said centre axis. The method further comprises the step of mounting said artificial caput femur surface, including the first beyond part thereof, on the caput femur in said functional position. This creates a more stable position of said artificial caput femur surface.

According to one embodiment, an artificial caput femur surface is adapted to be in connection with said acetabulum surface. It is conceivable that the diameter of the hole is larger than the largest diameter of the caput femur thus allowing the caput femur to pass through the hole. However it is also conceivable that said hole is smaller than the largest diameter of the caput femur thus hindering the caput femur from passing through the hole.

The artificial caput femur surface could comprises at least two caput femur surface parts adapted to be connected to each other after insertion in a hip joint to form an artificial caput femur surface. According to one embodiment the at least two artificial caput femur surface parts are inserted through a hole in the pelvic bone from the opposite side from acetabulum, said hole having a diameter less than the largest diameter of said artificial caput femur surface. The mechanical connection that connects the parts of the artificial caput femur surface could be created using: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. The surgical or laparoscopic/arthroscopic method could comprise the steps of: mounting said at least two artificial caput femur surface parts on caput femur to form an assembled medical device. The assembled medical device could be hollow. The method further comprises the steps of fixating said assembled medical device to the caput femur and surrounding, at least partly, the caput femur beyond said maximum diameter of said caput femur towards collum femur, the shape of said assembled medical device mechanically stabilizing the device when mounted on said caput femur.

According to another embodiment the artificial caput femur surface could be adapted to have a varying largest diameter for insertion through a hole in the pelvic bone from the opposite side from acetabulum of said human patient. Since the largest diameter of the artificial caput femur surface is adapted to vary between being both smaller and larger than the hole in the pelvic bone, the hole could have a diameter smaller than the largest diameter of the artificial caput femur surface.

The surgical or laparoscopic/arthroscopic method could comprise the step of inserting the artificial caput femur surface adapted to have a varying largest diameter through the hole in the pelvic bone. In this embodiment it is conceivable that the artificial caput femur surface is adapted to be flexible in its construction, thus enabling the insertion of said artificial caput femur surface through a hole in the pelvic bone that is smaller than said largest diameter of the artificial caput femur surface. The flexible part of the artificial caput femur surface could further be adapted to expand after insertion through the hole making the largest diameter of the artificial caput femur surface larger than the diameter of the hole in the pelvic bone, thus hindering the artificial caput femur surface from passing through the hole.

According to one embodiment the surgical or laparoscopic/arthroscopic method further comprises the step of introducing said hollow medical device onto said caput femur, having a diameter or cross-sectional distance of said opening larger than the diameter of said caput femur and having at least the smallest distance of said opening diameter or cross-sectional distance becoming smaller than said maximum diameter of said caput femur, after mounting said device on said caput femur and in a functional position thereon.

According to one embodiment the method further comprises using at least one slit for varying said opening diameter or opening cross-sectional distance, thus allowing the device to be introduced and mounted on the caput femur. The varying diameter according to any of the embodiments can be changed in relation to the mounting of said device onto the caput femur. The changing of said opening could include at least one of the following steps: Increasing an at least partly diameter or cross sectional distance to be able to mount said device on the caput femur, decreasing said at least partly diameter or cross sectional distance, to enable a stable position of the device on the caput femur when mounted thereon.

According to one embodiment the surgical or laparoscopic/arthroscopic method comprises the step of providing an artificial caput femur comprising at least two artificial caput femur surface parts. The method further comprises the step of inserting said at least two artificial caput femur surface parts through said hole in the pelvic bone from the opposite side from acetabulum of a human patient, said hole having a diameter less than the largest diameter of said caput femur. The at least two artificial caput femur surface parts could be adapted to be mechanically connected using at least one of the following: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

According to one embodiment the surgical or laparoscopic/arthroscopic method comprises providing an artificial caput femur surface adapted to have a varying largest diameter for insertion through a hole in the pelvic bone from the opposite side from acetabulum of said human patient. The hole has a diameter less than the largest diameter of said artificial caput femur surface of said human patient. The method further comprises the step of varying said largest diameter of said artificial caput femur surface between being both smaller and larger than the hole in the pelvic bone. The method steps could be performed by inserting said artificial caput femur surface through said hole in the pelvic bone and expanding said flexible construction of said artificial caput femur surface after said insertion through said hole making said artificial caput femur surface larger than said caput femur, thus not allowing passage through said hole in the pelvic bone.

According to one embodiment the surgical or laparoscopic/arthroscopic method comprises providing an artificial caput femur surface, wherein said artificial caput femur surface is hollow and has a greatest internal cross-sectional area and an opening with an area less than said greatest internal cross-sectional area of said artificial caput femur surface, when mounted on the caput femur of the human patient. The artificial caput femur surface further comprises at least one slit allowing the mounting of said artificial caput femur surface on the caput femur, which requires an opening area larger than the largest cross-sectional area of caput femur, and decreasing the size of said opening area to become smaller than said greatest internal cross-sectional area of said hollow medical device after said mounting on the caput femur.

According to one embodiment the artificial caput femur surface is frustum spherical.

According to one embodiment the surgical or laparoscopic/arthroscopic method comprises the steps of inserting said at least two artificial caput femur surface parts into said hip joint of said human patient and mounting said at least two artificial caput femur surface parts on said hip joint of said human patient to form said artificial caput femur surface, wherein said artificial caput femur surface is mechanically fixated to said caput femur by means of said mounting on the caput femur so that said artificial caput femur surface cannot be removed without dismounting said at least two artificial caput femur surface parts.

According to another embodiment the artificial caput femur surface is created inside of the hip joint using a mould or a sealed area. The method further comprises the step of injecting a fluid into a sealed area, the fluid serving as an artificial caput femur surface when it hardens.

According to one embodiment the surgical or laparoscopic/arthroscopic method comprises the step of placing a mould in the hip joint. In this embodiment it is further conceivable that said mould is placed in the hip joint through at least one of, the hip joint capsule, the pelvic bone, or the femoral bone using an instrument adapted therefore. This instrument could be equipped with a fixed angle, an adjustable angle or a parallel displaced part or section for improved reach.

According to another embodiment the above mentioned surgical or laparoscopic/arthroscopic method comprises the step of placing at least one sealing member in the hip joint. In this embodiment it is further conceivable that the mould is placed in the hip joint through at least one of, the hip joint capsule, the pelvic bone or the femoral bone using an instrument adapted therefore. This instrument could be equipped with a fixed angle, an adjustable angle or a parallel displaced part or section for improved reach.

According to above mentioned embodiments the artificial caput femur or acetabulum surface could comprises at least two artificial acetabulum/caput femur surface parts. According to these embodiments the surgical or laparoscopic/arthroscopic method could comprise the step of inserting these at least two artificial acetabulum/caput femur surface parts, in which case a surgical instrument adapted therefore could be used. Said instrument could be adapted to insert the parts through at least one of, the hip joint capsule, the pelvic bone, or the femoral bone. It is furthermore conceivable that said instrument is equipped with a fixed angle, an adjustable angle or a parallel displaced part or section for improved reach.

Please note that any embodiment or part of embodiment, feature, method, associated system, part of system described herein may be combined in any way.

BRIEF DESCRIPTION OF DRAWINGS

The embodiments are now described, by way of example, with reference to the accompanying drawings, in which:

FIG. 11 shows an artificial caput femur surface being larger than equator frustum spherical, FIG. 12a shows an artificial caput femur surface according to one embodiment, FIG. 12b shows an artificial caput femur surface according to one embodiment, when fixated to the caput femur, FIG. 13 shows cross-sectional views of the hip joint.

FIG. 16a-16e shows the artificial caput femur surface according to a yet another embodiment, FIG. 17a shows the artificial caput femur surface according to yet another embodiment, FIG. 17b shows the artificial caput femur surface according to 17a, in its folded state, FIG. 20 shows a conceptual view of the function of the expandable caput femur surface, FIG. 31a shows the providing of a first flexible layer onto the caput femur, FIG. 31b shows the caput femur when a flexible layer has been provided, FIG. 32a shown a medical device comprising multiple parts, FIG. 32b shown a medical device comprising multiple parts, in further detail, FIG. 33 shows the placing of a second stiff layer onto a first flexible layer, FIG. 34 shows the hip joint when a second stiff layer has been placed onto a first flexible layer.

FIG. 79 shows an artificial acetabulum surface according to a first embodiment, FIG. 80a shows an artificial acetabulum surface according to a second embodiment, FIG. 80b shows an artificial acetabulum surface according to the second embodiment in further detail, FIG. 80c shows the artificial acetabulum surface when assembled, FIG. 81a shows an artificial acetabulum surface according to a third embodiment, FIG. 81b shows an artificial acetabulum surface according to the third embodiment when assembled, FIG. 81c shows the connection function of the artificial acetabulum surface according to the third embodiment.

DETAILED DESCRIPTION

Figure 1:
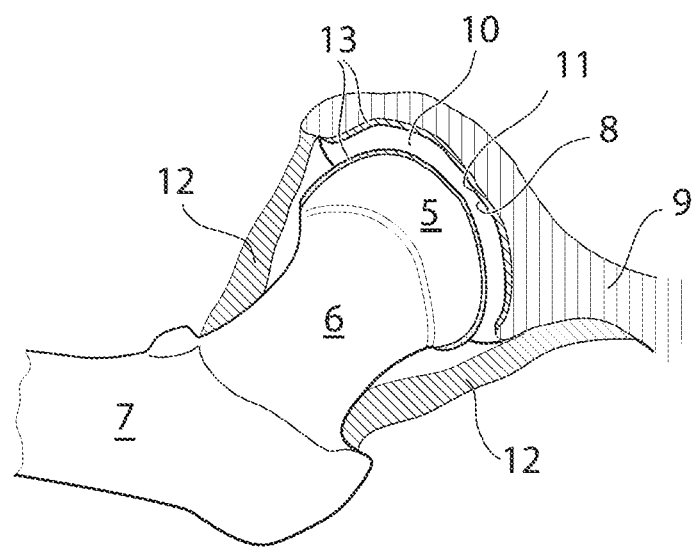
FIG. 1 shows the hip joint in section.

Biocompatible material is to be understood as being a material with low level of immune response. Biocompatible materials are sometimes also referred to as biomaterials. Analogous is biocompatible metals a metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

The contacting surfaces in any of the embodiments herein could comprise a ceramic material such as a Zirconium dioxide ceramic material.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5 placed at the very top of collum femur 6 which is the top part of the femoral bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position or normal functional position, of an implantable medical device or prosthesis is the position in which the hip joint can perform functional hip movements. The final position is to be understood as a functional position in which the medical device needs no further position change.

Functional opening is to be understood as an opening serving a purpose as opening in particular for receiving the caput femur and part of the femoral bone. The functional opening is depicted in all medical devices herein placed on the caput femur, since the caput femur is inserted through the functional opening.

Figure 2:
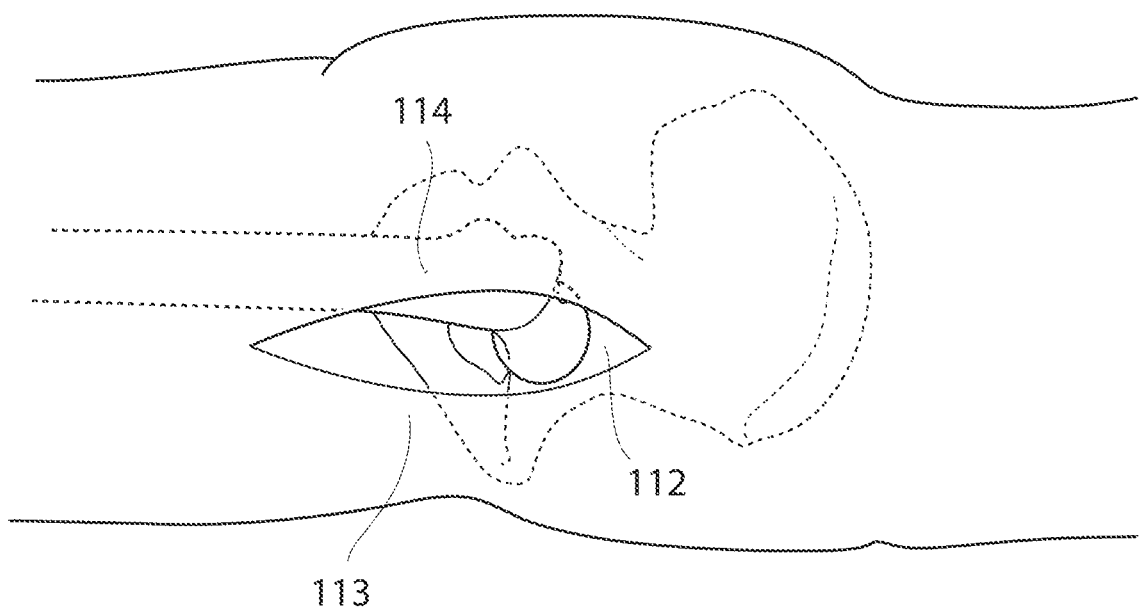
FIG. 2 shows a lateral view of a conventional hip joint surgery.

FIG. 2 shows a lateral view of a conventional hip joint surgery where an incision 112 is made in the tight 113 enabling the surgeon to reach the femoral bone 7 on which the caput femur 5 is located.

Figure 3:
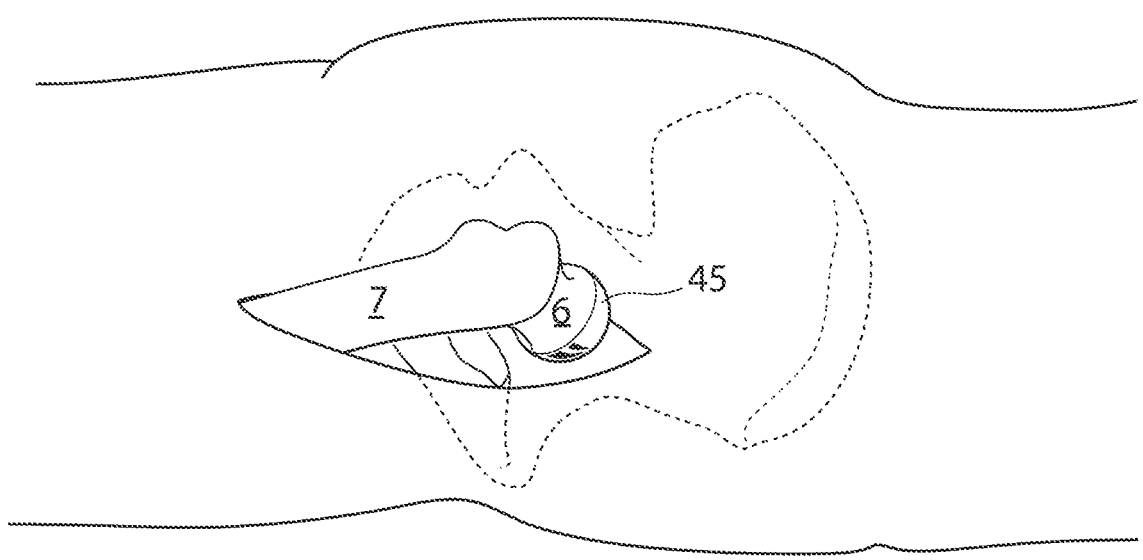
FIG. 3 shows a medical device, according to one embodiment, being used in conventional surgery.

FIG. 3 shows the placing of an artificial caput femur surface 45 on the caput femur 5 in conventional surgery when the femoral bone has been removed from its position in the hip joint.

Figure 4:
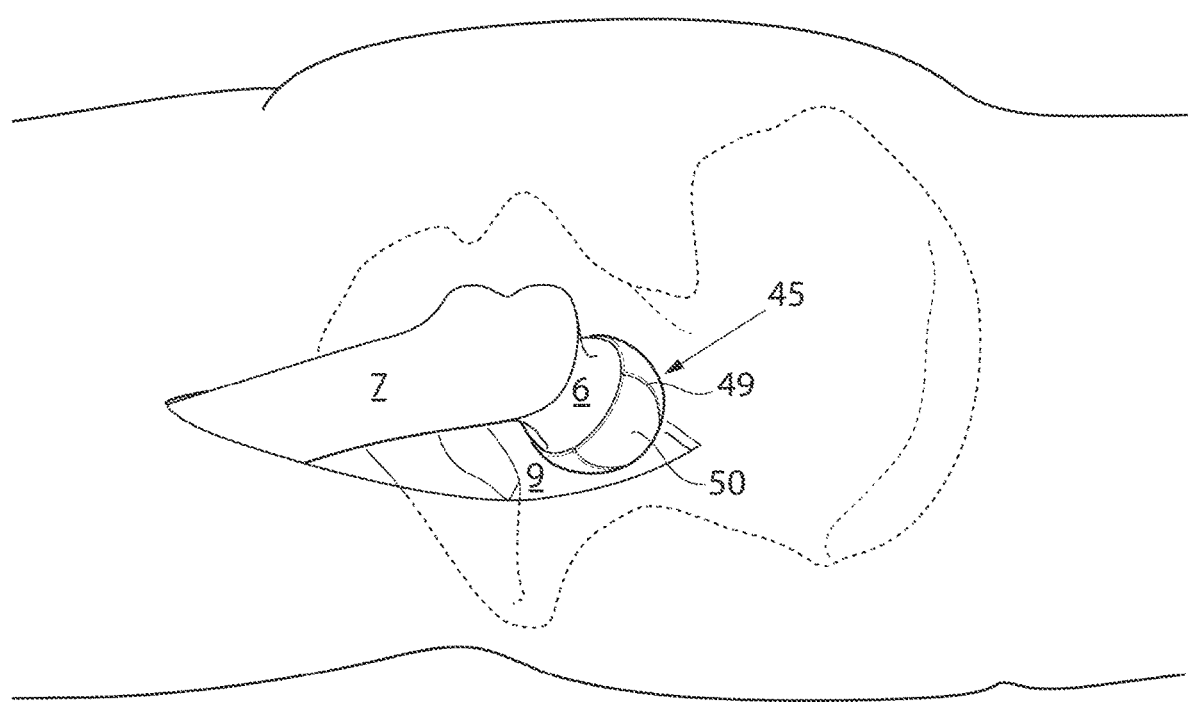
FIG. 4 shows a medical device, according to one embodiment, being used in conventional surgery.

FIG. 4 shows the placing of an artificial caput femur surface 45 on the caput femur in conventional surgery. The artificial caput femur according to this embodiment comprises slits 49 and arms 50 making the structure of the artificial caput femur surface flexible for clasping the caput femur 5 and going beyond the maximum diameter of the caput femur 5. Furthermore the artificial caput femur surface 45 can be inserted into a hip joint through a hole smaller than the full functional size of the artificial caput femur surface 45, enabling a less invasive surgical procedure.

Figure 5:
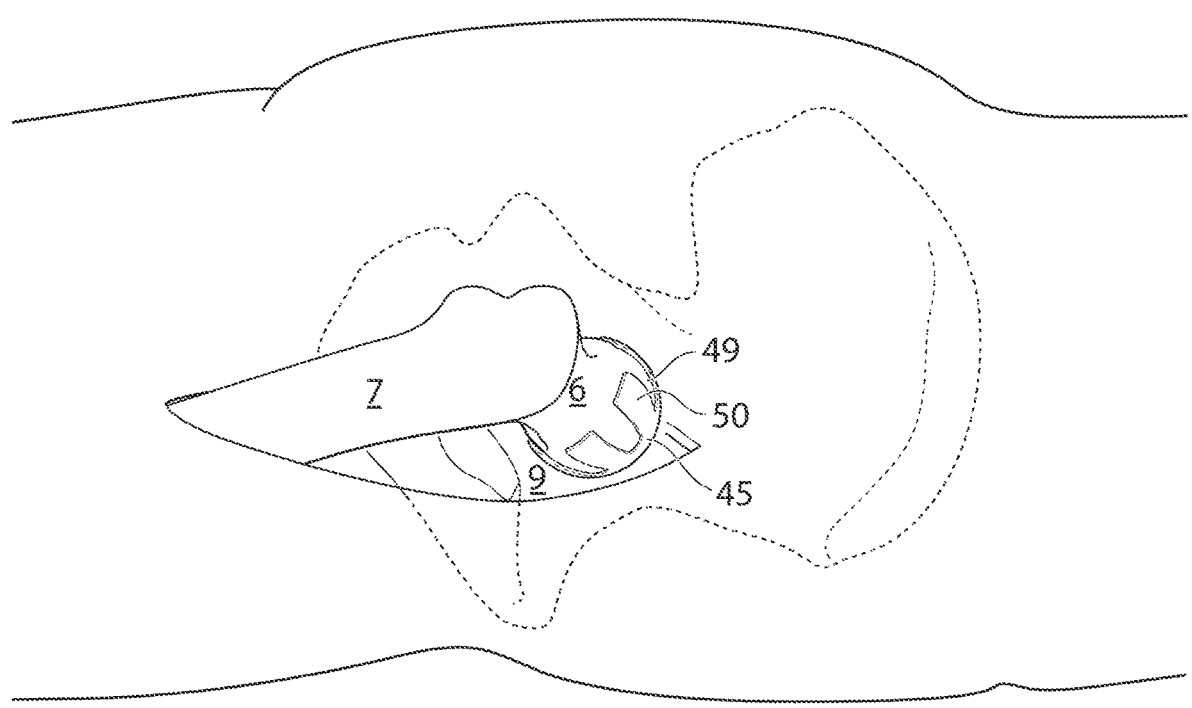
FIG. 5 shows a medical device, according to one embodiment, being used in conventional surgery.

FIG. 5 shows the placing of an artificial caput femur surface 45 on the caput femur in conventional surgery. The artificial caput femur according to this embodiment comprises slits larger slits 49 and smaller arms making the structure of the artificial caput femur surface flexible for clasping the caput femur 5 and going beyond the maximum diameter of the caput femur 5. Furthermore the artificial caput femur surface 45 can be inserted into a hip joint through a hole smaller than the full functional size of the artificial caput femur surface 45, enabling a less invasive surgical procedure.

Figure 6:
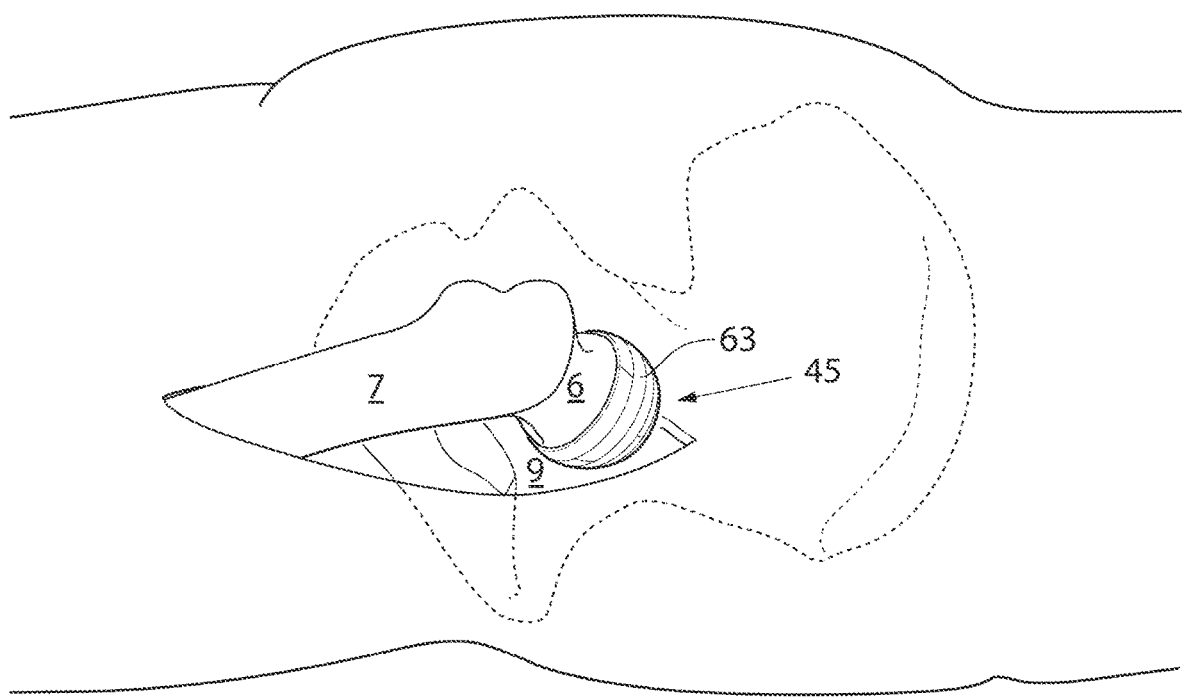
FIG. 6 shows a medical device, according to one embodiment, being used in conventional surgery.

FIG. 6 shows the placing of an artificial caput femur surface 45 on the caput femur in conventional surgery. The artificial caput femur surface 45 comprises multiple ring-shaped artificial caput femur surface parts 63. Said multiple ring-shaped artificial caput femur surface parts 63 are adapted to be connected to each other to form an artificial caput femur surface 45

Figure 7:
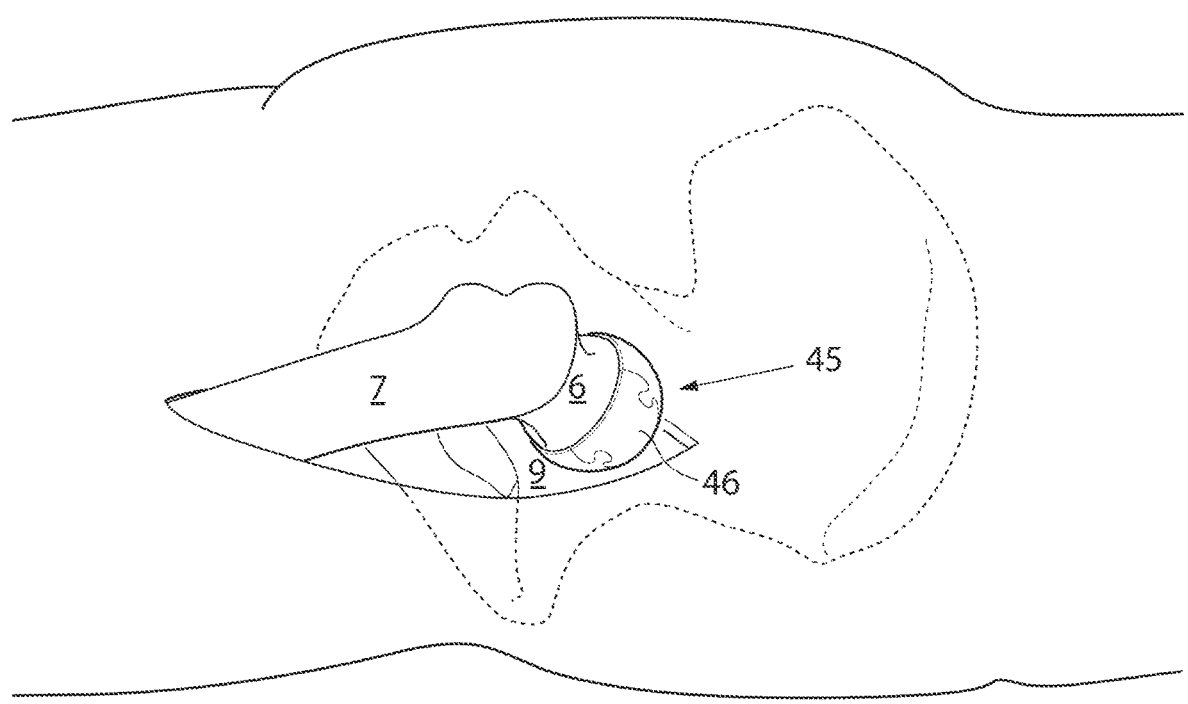
FIG. 7 shows a medical device, according to one embodiment, being used in conventional surgery.
Figure 8:
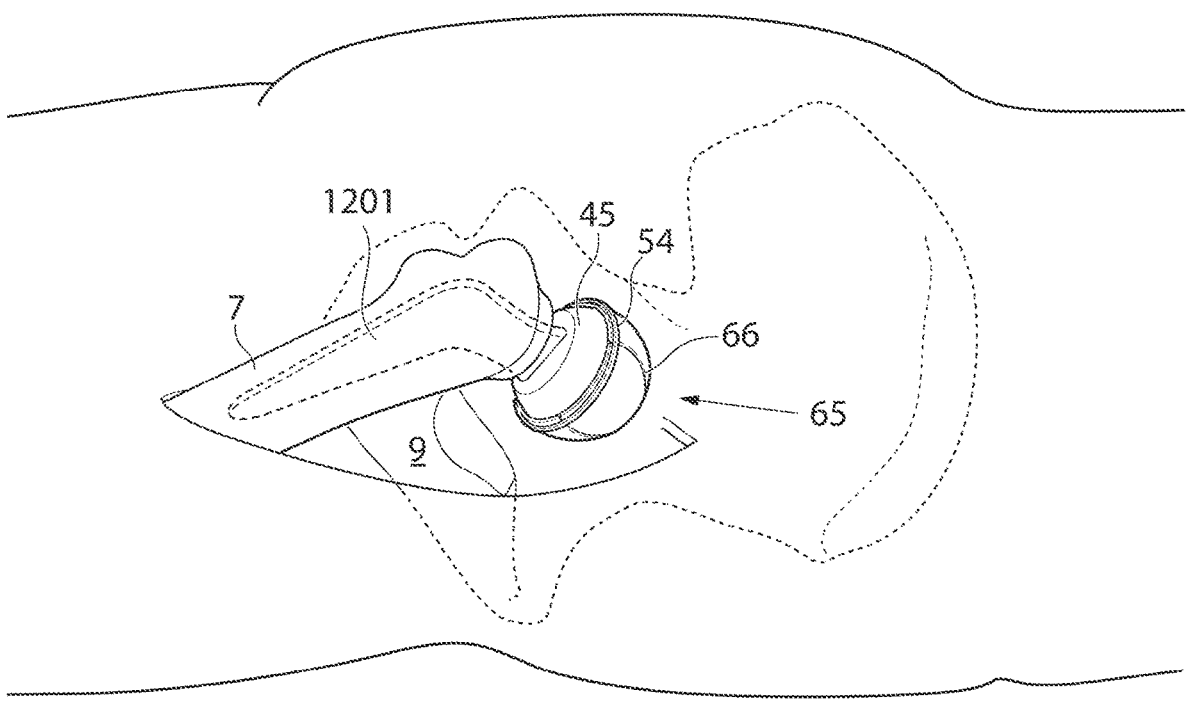
FIG. 8 shows a medical device, according to one embodiment, being used in conventional surgery.

FIG. 7 shows the placing of an artificial caput femur surface 45 on the caput femur in conventional surgery. The artificial caput femur surface 45 comprises multiple parts 46 adapted to be connected to each other to form an artificial caput femur surface 45 FIG. 8 shows the placing of an artificial caput femur 45 in conventional surgery, the femoral bone 7 has been cut at the neck, the collum femur, and the neck is replaced by a prosthetic stem 1201 which also fixates the medical device in the femoral bone 7 by the prosthetic stem being fixated in the femoral bone 7 either with bone cement or without. An artificial acetabulum surface 65 is pre-mounted on the artificial caput femur 45. The artificial acetabulum surface 65 is flexible by means of the artificial acetabulum surface 65 comprising slits 66. The artificial acetabulum surface 65 is further fixated by means of a band, cord or wire 59 placed beyond the maximum diameter of the caput femur for securing the artificial acetabulum 65 to the artificial caput femur 45.

Figure 9:
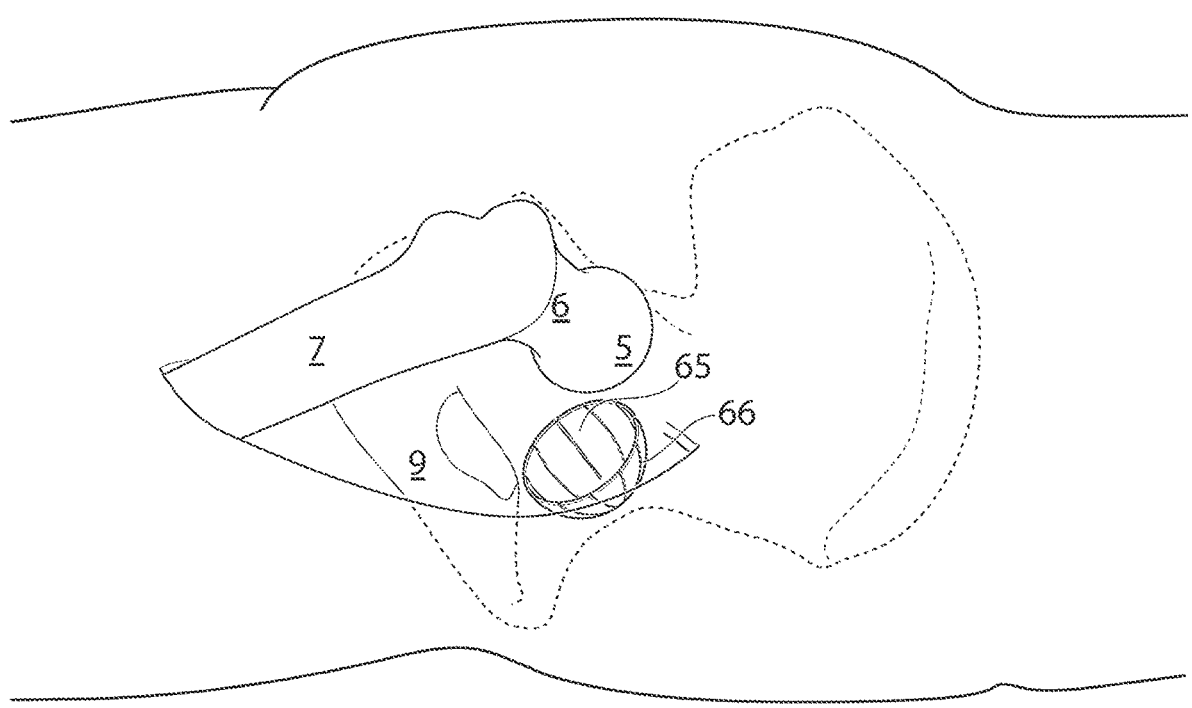
FIG. 9 shows a medical device, according to one embodiment, being used in conventional surgery.

FIG. 9 shows an artificial acetabulum surface 65 which has been placed in the acetabulum of a patient and fixated to the pelvic bone 9. The artificial acetabulum 65 is flexible in its construction by the artificial acetabulum comprising slits 66 which enables the artificial acetabulum 65 to travel beyond the maximum diameter of the caput femur 5 and/or passing through a hole smaller than the full functional size of the artificial acetabulum surface 65 enabling a less invasive surgical procedure.

Figure 10:
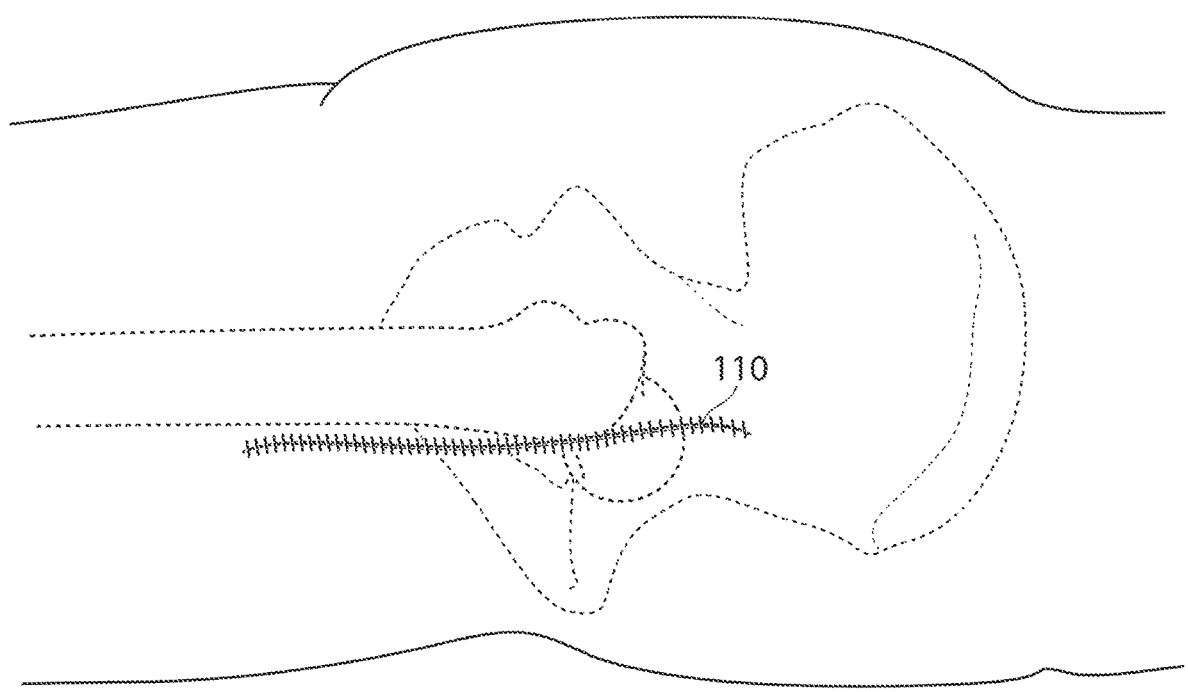
FIG. 10 shows a lateral view of the thigh region of the patient when the incision has been closed using sutures.

FIG. 10 shows a lateral view of the thigh region of a patient when the incision made to reach the hip joint have been closed by means of sutures 110.

FIG. 11 shows an artificial caput femur surface 45 in section having a greatest cross-sectional distance 52 adapted to travel over and beyond the maximum diameter of the caput femur 5. The maximum diameter of the caput femur 5 being positioned at a corresponding largest cross sectional distance 61 of the artificial caput femur surface A second distance 62 is the distance that the artificial caput femur surface 45 travels beyond the maximum diameter of the caput femur 5. Said distance 62 is the beyond part of the artificial caput femur surface and is a part of the mechanical fixation of the artificial caput femur surface 45 to the caput femur 5.

FIG. 12*a* shows an artificial caput femur surface according to a first embodiment, the artificial caput femur surface 45 is adapted to pass beyond the maximum diameter of the caput femur 5. This enables a mechanical fixation using the form of said artificial caput femur surface 45. In this embodiment the artificial caput femur surface 45 comprises at least one slit 49 adapted to make said artificial caput femur surface 45 flexible for traveling over and beyond the maximum diameter of the caput femur 5. The construction could further be made flexible so that the size of the artificial caput femur surface 45 can vary to become smaller for insertion through a hole 18 in the pelvic bone 9 smaller than the full functional size of the artificial caput femur surface 45. It is also conceivable that the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50. For further fixation a band, cord or wire 59 can be placed around the artificial caput femur surface 45 beyond the maximum diameter of the caput femur 5. The band, cord or wire 59 can be mechanically connected using a self locking member 60 for forming a ring-shaped element able to assist in the fixation of the artificial caput femur surface 45 to the caput femur 5.

FIG. 12*b* shows the artificial caput femur surface 45 when fixated to the caput femur with the supporting band, cord or wire placed around the artificial caput femur surface 45 beyond the maximum diameter of the caput femur 5. The arms may also be adapted to go into the bone of caput femur 5 to lock said artificial caput femur surface 45.

FIG. 13 shows the hip joint in section, the hip joint has a collum femur 6, having a first axial distribution leading to a caput femur 5, the center axis L1 of the caput femur 5 being the caput femur center axis L1, caput femur having a substantially ball shaped configuration with an outer maximum diameter 1203, shown in the section A-A, substantially perpendicular to the caput femur center axis L1. The caput femur 5 is normally placed in a bowl shaped acetabulum 8, having an opening, the bowl shaped acetabulum 8 has a second axial distribution with an acetabulum center axis L2 from the center of the bottom of the acetabulum bowl 8 and following the center of the bowl towards the center of the opening of the bowl towards the caput femur 5. The acetabulum bowl 8 has an inner maximum diameter 1202, as shown in the section B-B, substantially perpendicular to the acetabulum center axis L2, wherein the caput femur center axis L1 is in line with the acetabulum center axis L2 in a special centered position when the caput femur 5 is: placed, aligned, centered and symmetrical, as shown in FIG. 13, in the acetabulum bowl 8 in the hip joint. The caput femur 5 and the acetabulum 8 have one hip joint surface each, placed towards and contacting each other, the hip joint surfaces carries weight in the hip joint.

Figure 14:
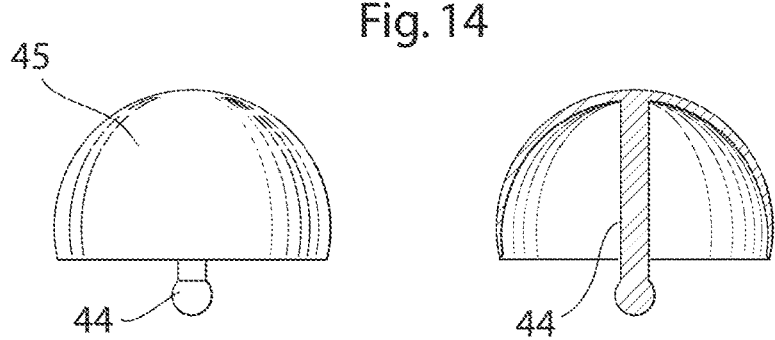
FIG. 14 shows an artificial caput femur surface according to one embodiment.

FIG. 14 shows the artificial caput femur surface 45 according to a second embodiment, The shaft or screw placed in the middle of the artificial caput femur surface 45 serves as a mechanical attachment 44 penetrating the cortex of the caput femur 5 and fixating the artificial caput femur surface 45 to the caput femur 5. However it is also conceivable that said shaft or screw is assisted or replaced with screws, welding, sprints, band, adhesive or some other mechanical connecting member.

Figure 15A:
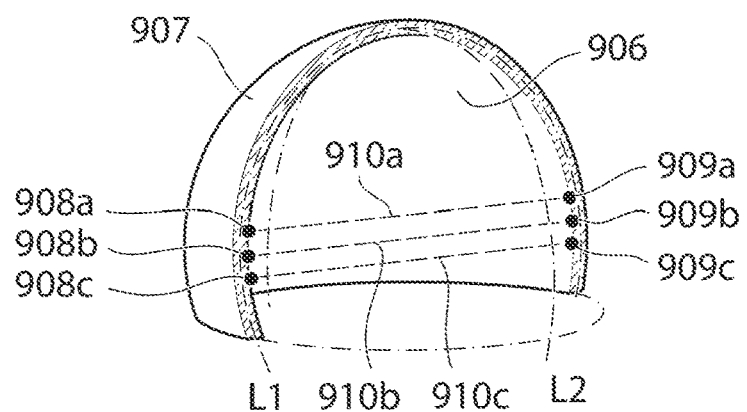
FIG. 15a shows an artificial caput femur surface according to a larger than equator frustum spherical embodiment.

FIG. 15 a shows an artificial hip joint surface according to an embodiment where the artificial hip joint surface comprises an inner surface 906, and an outer surface 907. The inner surface has a first point 908*a*, a second point 909*a*, a third point 908*b*, a fourth point 909*b*, a fifth point 908*c*, and a sixth point 909*c*, all points located on different places along a length axis L1 of said inner surface 906, wherein: a first straight line 910*a*, reaching from said first point 908*a* to said second point 909*a* is parallel to a second straight line 910*b* reaching from said third point 908*b* to said fourth point 909*b*, which in turn is parallel to a third straight line 910*c* reaching from said fifth point 908*c* to said sixth point 909*c*, wherein: said first and said third straight lines 910*a*, 910*c* are of equal length, and wherein said second straight line 910*b* is longer than said first 910*a* and said third 910*c* straight lines and positioned between said first 910*a* and said third 910*c* straight lines. The artificial hip joint surface is thereby passing beyond the maximum diameter of the of the artificial hip joint surface, which enables the artificial hip joint surface to clasp an element such as the caput femur 5, an artificial caput femur surface or an artificial replacement for the caput femur. The artificial hip joint surface is curved in more than one direction, as shown with reference to L1 and L2 being lines following the curvature in perpendicular directions.

Figure 15B:
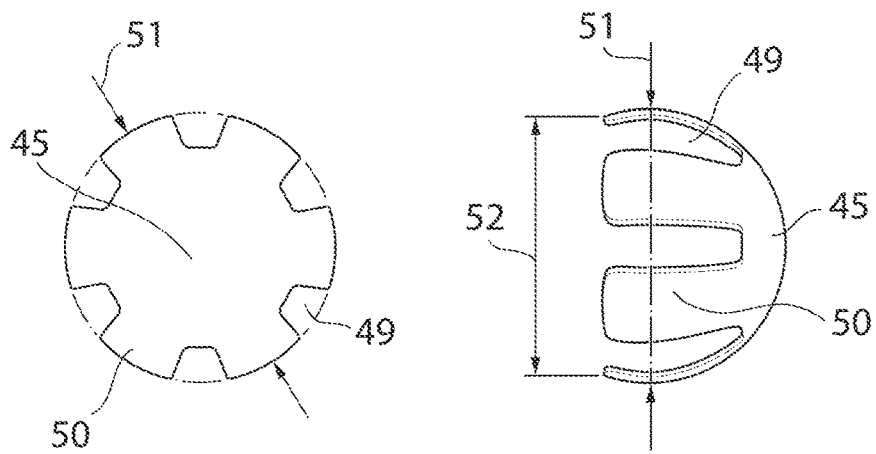
FIG. 15b shows the artificial caput femur surface according to another embodiment.

FIG. 15*b* shows the artificial caput femur surface 45 according to a third embodiment, in which said artificial caput femur surface 45 comprises at least one slit 49 enabling the construction of the artificial caput femur surface 45 to be flexible, thus enabling the largest diameter 51 to vary for insertion of said artificial caput femur surface 45 through a hole in the pelvic bone 9 smaller than the full functional size of said artificial caput femur surface 45. According to this embodiment the artificial caput femur surface 45 further comprises artificial caput femur surface arms 50 located on the sides of said at least one slit 49. The caput femur surface arms 50 can be made of a flexible material enabling the insertion through a hole 18 in the pelvic bone 9 smaller than the largest diameter 51 of said artificial caput femur surface 45 when in its full functional size.

According to one embodiment the artificial caput femur surface 45 of said third embodiment could be adapted to pass beyond the maximum diameter of the caput femur 5. This enables a mechanical fixation using the form of said artificial caput femur surface 45. In the embodiment where the artificial caput femur surface 45 travels beyond the maximum diameter of the caput femur 5 the construction can be made flexible so that the size of the artificial caput femur surface 45 can vary to become smaller for insertion through a hole 18 in the pelvic bone smaller than the full functional size of the artificial caput femur surface 45, and have an opening adapter to travel over the caput femur 5 that can be larger that the same opening is in the full functional size of the artificial caput femur surface 45 enabling the artificial caput femur surface 45 to at least partly cover an area beyond the maximum diameter of caput femur 5 from the direction of the acetabulum 8. According to a second embodiment the artificial caput femur surface 45 comprises two or more artificial caput femur surface arms 50 which have a cross sectional distance 52 between each other. This cross sectional distance 52 is according to one embodiment shorter than the maximum diameter of the caput femur 5 enabling the mechanical fixation of the artificial caput femur surface 45 by means of said artificial caput femur surface arms 50.

FIG. 16a,b,c,d,e shows the artificial caput femur surface 45 according to a fourth embodiment, in which said artificial caput femur surface 45 comprises a first 53a and a second 53b section, as shown in FIG. 8b. The first and second sections are displaceable in relation to each other. According to a first embodiment said first section 53a can be rotated in relation to said second section 53b so that said second section 53b travels underneath said first section 53a to create a displaced artificial caput femur surface 54, as shown in FIG. 8c, which is possible to insert into a hip joint of a human patient through a hole 18 being oval, or at least having an area smaller than the cross sectional area of the artificial caput femur surface 45 when in its full functional size 45, as shown in FIG. 8a. According to this embodiment the two sections are connected to each other when the artificial caput femur surface 45 is returned to its full functional size using a mechanical form fitting 55, as shown in FIG. 8e. However it is also conceivable that said connection is assisted or replaced with screws, welding, sprints, band, adhesive or some other mechanical connecting member.

FIG. 17a,b shows the artificial caput femur surface 45 according to a fifth embodiment, in which said artificial caput femur surface 45 comprises four slits. The artificial caput femur surface 45 is flexible in its construction allowing the four artificial caput femur arms 50 to be folded towards the center axis of the artificial caput femur surface 45 thus allowing the artificial caput femur surface 45 to be inserted into a hip joint through a hole smaller than the full functional size of the artificial caput femur surface 45. The artificial caput femur surface 45 according to this embodiment can be constructed to go beyond the maximum diameter of the caput femur 5, in which case the construction with the slits 49 allows the artificial caput femur surface 45 to change to both a smaller and a larger size than said full functional size.

FIG. 17b shows the artificial caput femur surface 45 in section when said artificial caput femur surface arms 50 are folded for insertion through a hole 18 with an area smaller than the largest area of the artificial caput femur surface 45 when in its full functional size.

Figure 18A:
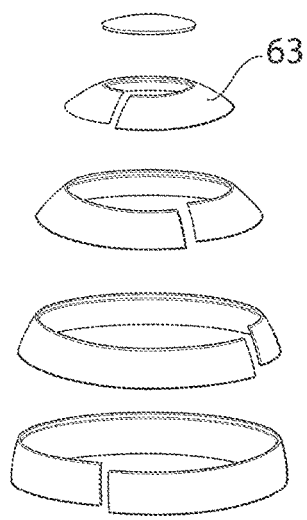
FIG. 18a shows the artificial caput femur surface according yet another embodiment.
Figure 18B:
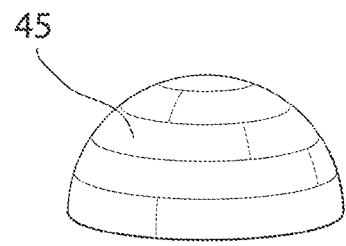
FIG. 18b shows the artificial caput femur surface according to the embodiment of 18a when assembled.
Figure 18C:
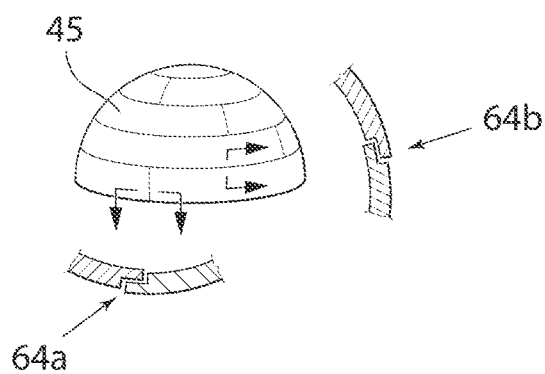
FIG. 18c shows the artificial caput femur surface according to 18a,b with the connecting members enlarged.

FIG. 18a shows the artificial caput femur surface 45 according to a sixth embodiment, in which said artificial caput femur surface 45 comprises multiple ring-shaped artificial caput femur surface parts 63. Said multiple ring-shaped artificial caput femur surface parts 63 are adapted to be connected to each other to form an artificial caput femur surface 45, shown in FIG. 18b. According to one embodiment said artificial caput femur surface parts 63 are adapted to be connected to each other using mechanical connecting members 64a,b. In FIG. 18c, 64a shows how an individual ring-shaped artificial caput femur surface part 63 can be connected to itself to form a continuous ring shape. 64b shows how an individual ring-shaped artificial caput femur surface part 63 connects to other ring-shaped artificial caput femur surface parts 63 to form an artificial caput femur surface 45. The artificial caput femur surface 45 according to this embodiment can further be adapted to go beyond the maximum diameter of the caput femur 5.

Figure 19A:
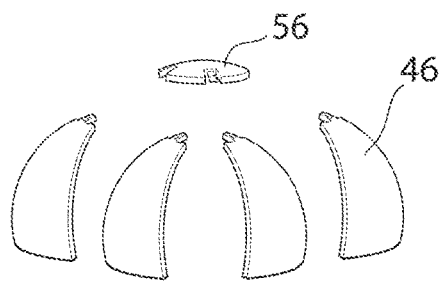
FIG. 19a shows the artificial caput femur surface according to yet another embodiment.
Figure 19B:
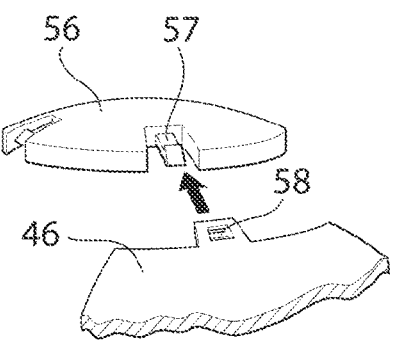
FIG. 19b shows the artificial caput femur surface according to 19a in greater detail.

FIG. 19a,b,c shows the artificial caput femur surface 45 according to a sixth embodiment, in which said artificial caput femur surface 45 comprises multiple artificial caput femur surface parts 46. Said multiple artificial caput femur surface parts 46 are adapted to be connected to an interconnecting artificial caput femur surface part 56 after insertion into a hip joint. The interconnecting artificial caput femur surface part, which serves as a base part 56, comprises self locking connecting members 57, shown in FIG. 19b, that fits with corresponding self locking members 58 of the artificial caput femur surface parts 46. The artificial caput femur surface has a substantially even surface which according to one embodiment has a height difference 1204 of maximally 10 micrometer, according to another embodiment has a height difference 1204 of maximally 100 micrometer and according to another embodiment has a height difference 1204 of maximally 1 millimeter. The artificial caput femur surface 45 can further be adapted to go beyond the maximum diameter of the caput femur 5.

FIG. 20 shows an artificial acetabulum surface 45 according to an embodiment in which the artificial caput femur surface comprises multiple movable portions 1224 connected to an interconnecting part 56 by operable joints 1205 placed along one side of the movable portions 1224. The artificial caput femur surface is further fixated to the caput femur by a band, cord or wire 59 placed beyond the maximum diameter of the caput femur 5, after the movable portions 1224 have been placed in there functional position clasping the caput femur 5. The section A-A shows a movable portion 1224 when not in its functional state. The movable portion being connected to an interconnecting part 56 through a movable member in form of a hinge 1205 allowing the movable portion to move for being able to clasp the caput femur 5 and/or changing the maximum diameter of the artificial caput femur surface for passing through a hole smaller than the maximum diameter of the caput femur surface in its functional state, in which case the movable member is moved in a direction towards the center of the artificial caput femur surface (not shown).

Figure 21:
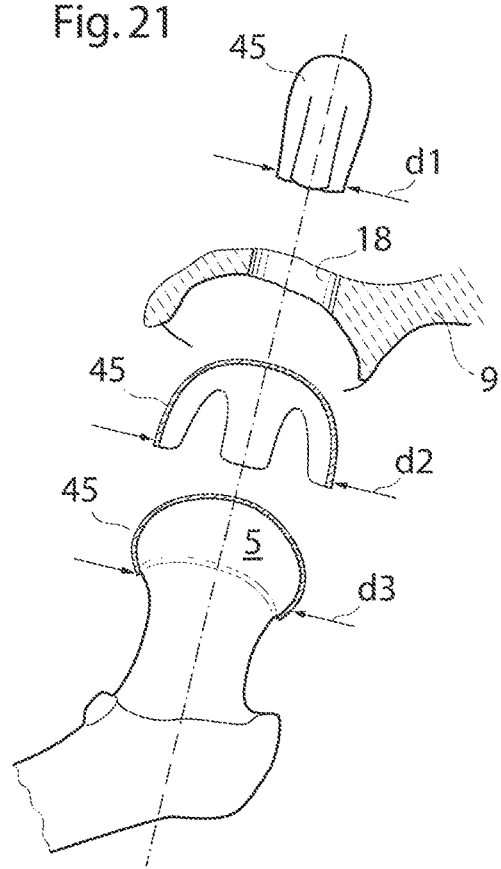
FIG. 21 shows a conceptual view of the function of the expandable caput femur surface.

FIG. 21 shows a conceptual view wherein the artificial caput femur surface 45, according to any of the embodiments herein, has a diameter or cross-sectional distance d1 small enough to enable said artificial caput femur surface 45 to travel through a hole 18 in the pelvic bone 9. After the artificial caput femur surface 45 has traveled through the hole 18 in the pelvic bone 9 the artificial caput femur surface 45 is expanded such that the diameter or cross-sectional distance d2 is large enough to travel over the caput femur 5. Finally the artificial caput femur surface 45 is positioned on the caput femur 5, in this state the diameter d3 or cross-sectional distance is smaller than the largest diameter of the caput femur 5, which mechanically attaches the artificial caput femur surface 45 to the caput femur 5. d3 is the normal sate cross sectional distance of the medical device, i.e. the cross sectional distance that the medical device has when the medical device is in its functional position. This figure may also in an alternative embodiment show the artificial acetabulum surface mounted onto caput femur or an artificial replacement therefore with the same locking principle.

Figure 22A:
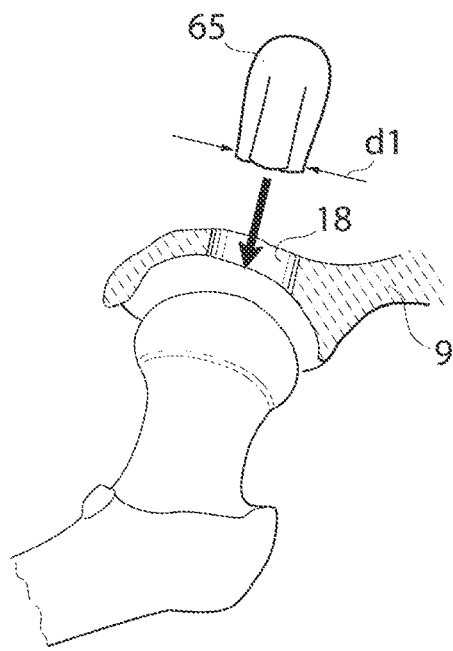
FIG. 22a shows a conceptual view of the function of the expandable acetabulum surface.
Figure 22B:
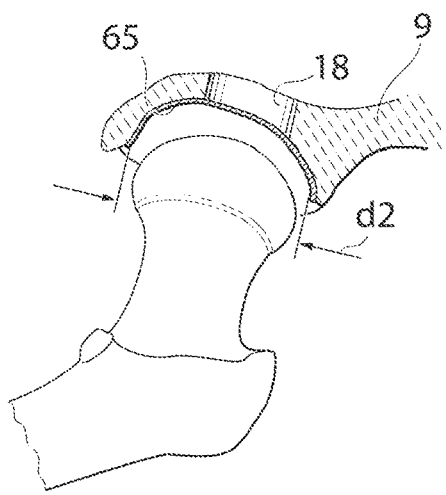
FIG. 22b shows the hip joint in section when an artificial acetabulum surface has been provided.

FIG. 22a shows a conceptual way wherein the artificial acetabulum surface 65 has a diameter or cross-sectional distance d1 small enough to enable said artificial acetabulum surface 65 to travel through a hole 18 in the pelvic bone 9. After the artificial acetabulum surface 65 has traveled through the hole 18 in the pelvic bone 9 the artificial acetabulum surface is expanded such that the diameter or cross-sectional distance d2 is large enough to hinder the artificial acetabulum surface 65 from traveling through the hole 18 in the pelvic bone 9 as shown in FIG. 22b.

Figure 23:
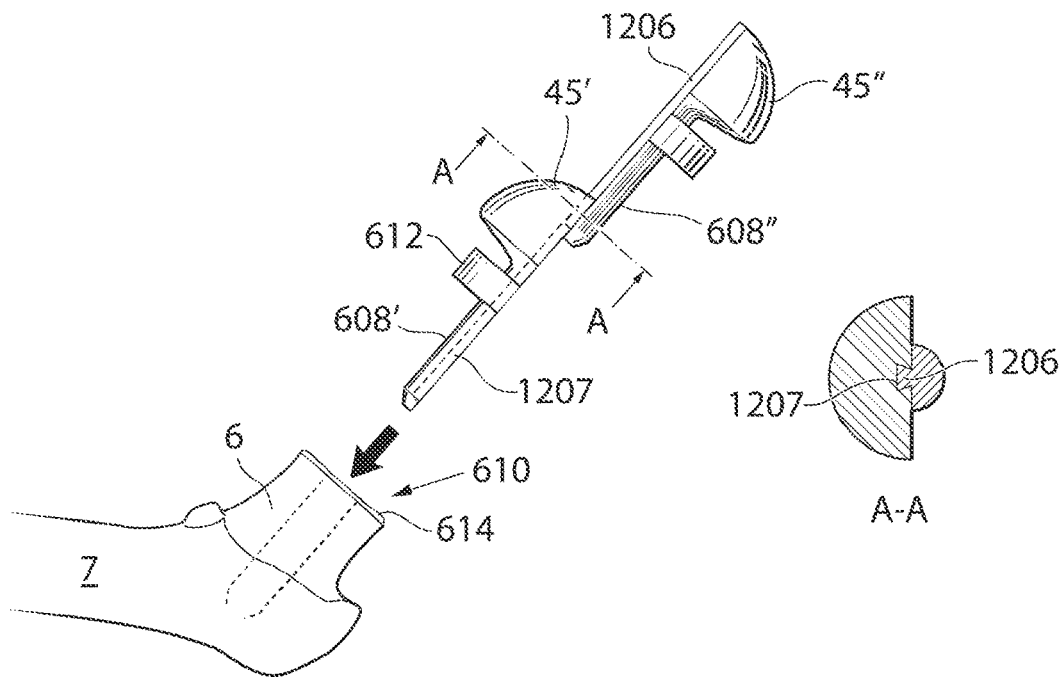
FIG. 23 shows the assembly of a medical device.

FIG. 23 shows the medical device according to an embodiment where the medical device comprises an artificial caput femur 45, a fixating member 608, and a stabilizing member 612 adapted to stabilize the medical device from the outside of the collum femur 6, substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The stabilizing member 612 and the fixating member 608 could be fixated to the collum femur 6 by means of an adhesive 614 or bone cement. The stabilizing member 612 is made from an artificial material such as a biocompatible metal, (e.g. titanium or tantalum), or a biocompatible polymer or ceramic material. The medical device comprises two parts which are adapted to be interconnected to form an interconnected medical device. The first part of the medical device comprises a first part of the fixating member 608', and a first part of the caput femur surface 45'. The second part of the medical device comprises a second part of the fixating member 608", and a second part of the caput femur surface 45". The parts are adapted to be connected to each other by a sliding dovetail joint. The first part of the medical device comprises a dovetail groove 1207 which matches the dovetail section 1206 of the second part of the medical device. The two parts can be interconnected to form the medical device, before or during a surgical procedure, preferably the parts are jointed during the surgical procedure since this enables the parts to be introduced into the hip joint through a hole smaller than a hole which through which the interconnected medical device could pass. The cross-section A-A shows the fixating part and the artificial caput femur 45, when they are interconnected by means of the sliding dovetail 1206, 1207.

Figure 24:
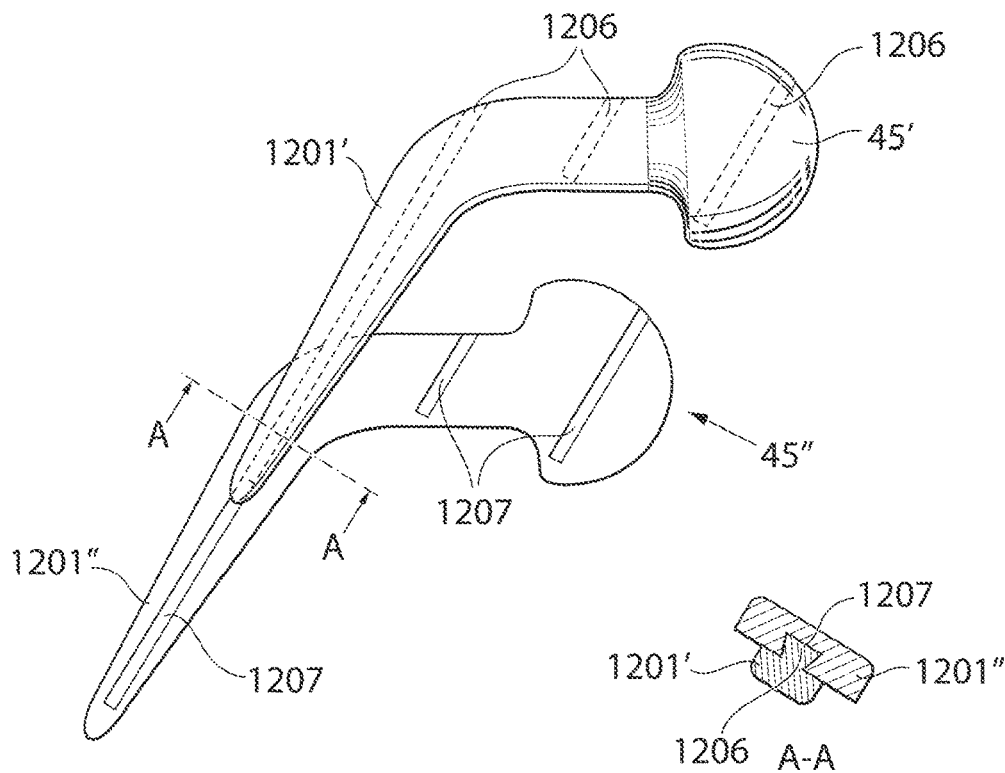
FIG. 24 shows the assembly of a medical device.

FIG. 24 shows the medical device comprising an artificial caput femur 45 and a prosthetic stem 1201. The medical device comprises two parts each comprising a part of the prosthetic stem 1201',1201" and the artificial caput femur surface 45',45". The medical device is adapted to be interconnected by multiple sliding dovetail joints 1206,1207, wherein dovetail grooves 1207 in the second part of the medical device matches the dovetail sections 1206 of the first part of the medical device. The cross-section A-A shows the prosthetic stem of the first part 1201' having a dovetail section 1206 and the prosthetic stem of the second part having a dove tail groove 1207.

Figure 25:
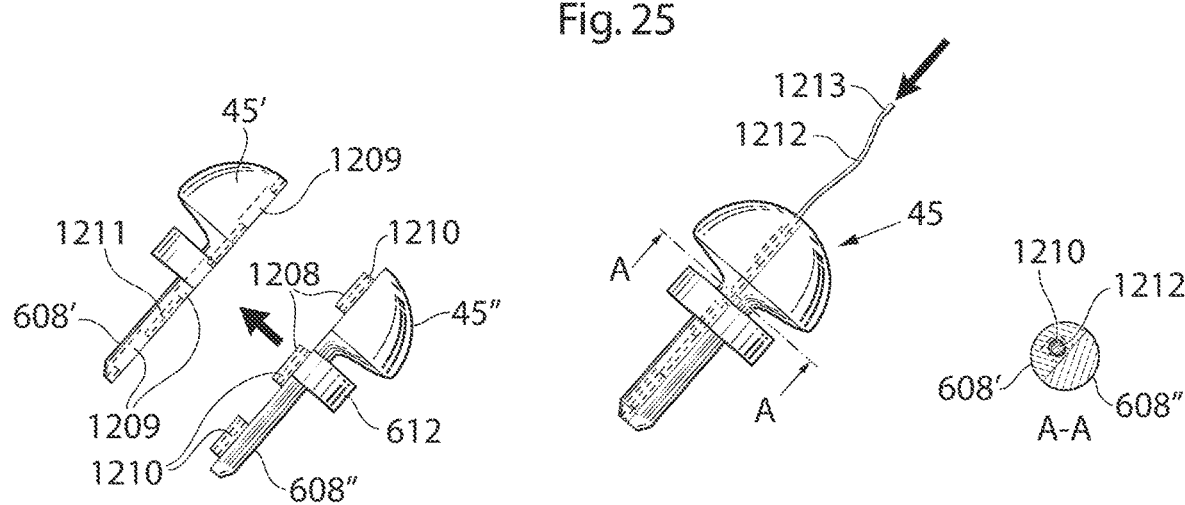
FIG. 25 shows the assembly of a medical device.

FIG. 25 shows the medical device according to an embodiment where the medical device comprises an artificial caput femur 45, a fixating member 608, and a stabilizing member 612 adapted to stabilize the medical device from the outside of the collum femur 6, substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The medical device comprises two parts which are adapted to be interconnected to form an interconnected medical device. The first part of the medical device comprises a first part of the fixating member 608', and a first part of the caput femur surface 45'. The second part of the medical device comprises a second part of the fixating member 608", and a second part of the caput femur surface 45". The parts are adapted to be connected to each other by a construction with pins 1209 and grooves 1208 matching each other. The first part of the medical device comprises the grooves 1209 which matches the pins 1208 of the second part of the medical device. The two parts can be interconnected to form the medical device, before or during a surgical procedure, preferably the parts are jointed during the surgical procedure since this enables the parts to be introduced into the hip joint through a hole smaller than a hole which through which the interconnected medical device could pass. The pins 1208 and grooves 1209 are secured by an elongated member 1212, which could be flexible, such as a wire, or stiff, such as a pin, The elongated member 1212 is adapted to be inserted into a hole 1210 of the pins 1208 and a hole 1211 of the first part of the medical device, thereby securing the pins in the grooves 1211. The cross-section A-A shows the fixating parts 608',608" of the medical device with the elongated member 1212 placed in the hole 1211 in the medical device and the hole 1210 in the pins 1208. The elongated member comprises an end portion 1213 having a flat upper surface adapted to form part of the artificial caput femur surface 45.

Figure 26:
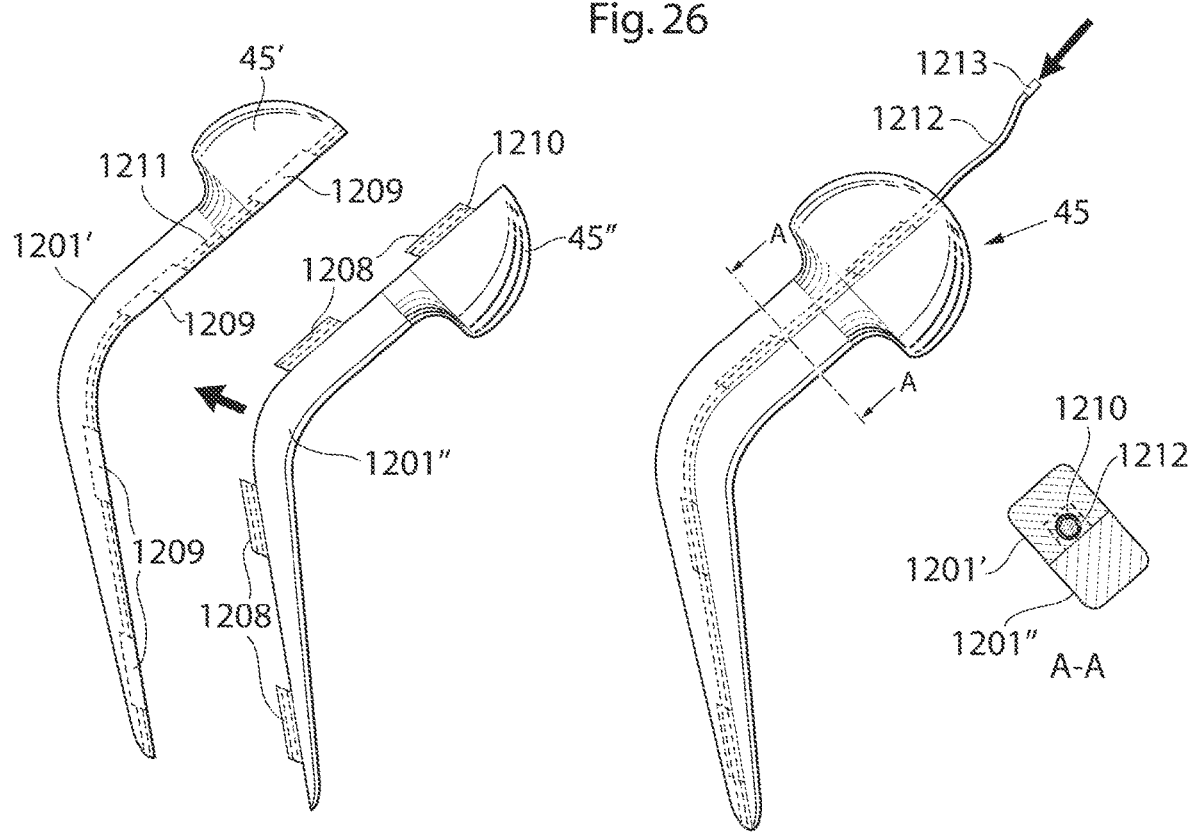
FIG. 26 shows the assembly of a medical device, FIG. 27a,b,c shows the assembly of a medical device, FIG. 28a,b,c shows the assembly of a medical device, FIG. 29a,b,c shows the assembly of a medical device, FIG. 30a,b,c shows the assembly of a medical device.

FIG. 26 shows the medical device comprising an artificial caput femur 45 and a prosthetic stem 1201. The medical device comprises two parts each comprising a part of the prosthetic stem 1201', 1201" and the artificial caput femur surface 45',45". The parts are adapted to be connected to each other by a construction with pins 1208 and grooves 1209 matching each other. The first part of the medical device comprises the grooves 1209 which matches the pins 1208 of the second part of the medical device. The two parts can be interconnected to form the medical device, before or during a surgical procedure, preferably the parts are jointed during the surgical procedure since this enables the parts to be introduced into the hip joint through a hole smaller than a hole which through which the interconnected medical device could pass. The pins 1208 and grooves 1209 are secured by an elongated member 1212, which could be flexible, such as a wire, or stiff, such as a pin, The elongated member 1212 is adapted to be inserted into a hole 1210 of the pins 1208 and a hole 1211 of the first part of the medical device, thereby securing the pins in the grooves 1211. The cross-section A-A shows the prosthetic stem parts 1201', 1201" of the medical device with the elongated member 1212 placed in the hole 1211 in the medical device and the hole 1210 in the pins 1208. The elongated member comprises an end portion 1213 having a flat upper surface adapted to form part of the artificial caput femur surface 45.

Figure 27A:
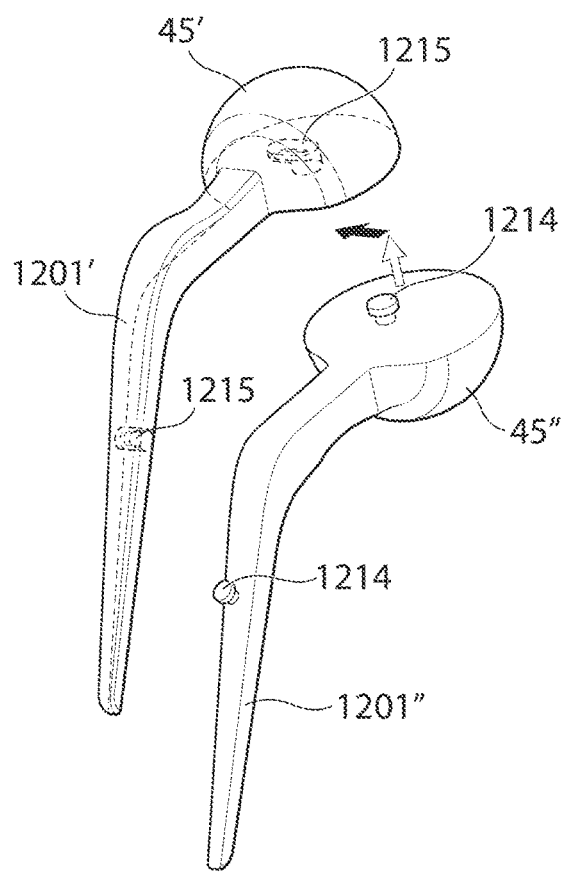
Figure 27B:
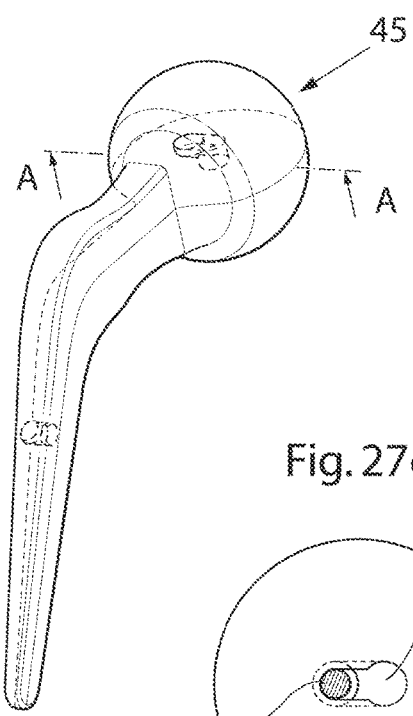
Figure 27C:
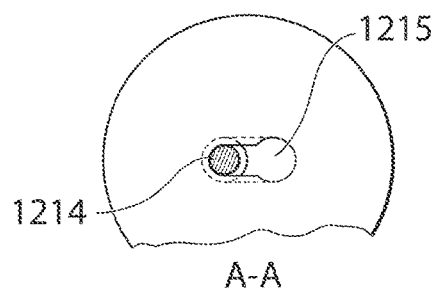

FIG. 27a shows the medical device comprising an artificial caput femur 45 and a prosthetic stem 1201. The medical device comprises two parts each comprising a part of the prosthetic stem 1201',1201" and the artificial caput femur surface 45',45". The parts are adapted to be connected to each other by a construction with pins 1214 and holes 1215 matching each other. The first part of the medical device comprises the holes 1215 which are adapted to receive the pins 1214 in a first direction and thereafter lock the pins in the holes in a second direction. The two parts can be interconnected to form the medical device, as shown in FIG. 27*b*, before or during a surgical procedure, preferably the parts are jointed during the surgical procedure since this enables the parts to be introduced into the hip joint through a hole smaller than a hole which through which the interconnected medical device could pass. The cross section A-A of FIG. 27*c* shows a pin 1214 in a hole 1215 after it firstly has been introduced in one direction and secondly been pushed to the side to lock the pin 1214 in the hole.

Figure 28A:
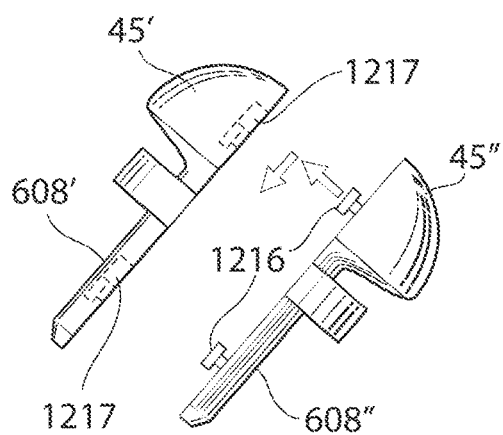
Figure 28B:
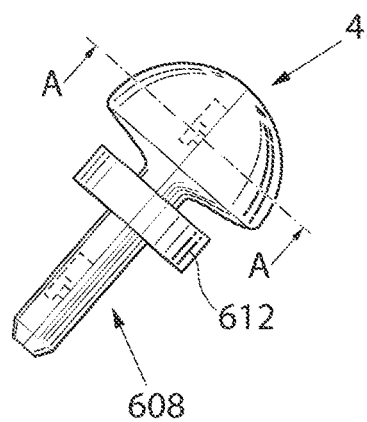
Figure 28C:
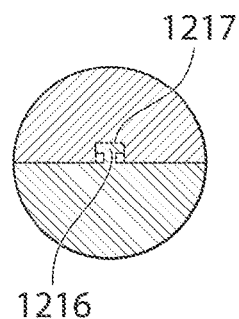

FIG. 28*a* shows the medical device according to an embodiment where the medical device comprises an artificial caput femur 45, a fixating member 608, and a stabilizing member 612 adapted to stabilize the medical device from the outside of the collum femur 6, substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The medical device comprises two parts which are adapted to be interconnected to form an interconnected medical device, as shown in FIG. 28*b*. The first part of the medical device comprises a first part of the fixating member 608', and a first part of the caput femur surface 45'. The second part of the medical device comprises a second part of the fixating member 608", and a second part of the caput femur surface 45". The parts are adapted to be connected to each other by a construction with pins 1216 and holes 1217 matching each other. The first part of the medical device comprises the holes 1217 which are adapted to receive the pins 1216 in a first direction and thereafter lock the pins 1216 in the holes 1217 in a second direction. The two parts can be interconnected to form the medical device, before or during a surgical procedure, preferably the parts are jointed during the surgical procedure since this enables the parts to be introduced into the hip joint through a hole smaller than a hole which through which the interconnected medical device could pass. The cross section A-A, of FIG. 28*c*, shows a pin 1216 in a hole 1217 after it firstly has been introduced in one direction and secondly been pushed to the side to lock the pin 1216 in the hole 1217.

FIG. 29*a* shows the medical device comprising an artificial caput femur 45 and a prosthetic stem 1201. The medical device comprises two parts each comprising a part of the prosthetic stem 1201',1201" and the artificial caput femur surface 45',45". The parts are adapted to be connected to each other by a construction with a pin 1218 and a hole 1219 matching each other. The first part of the medical device comprises the hole 1219 which are adapted to receive the pin 1218 in a first direction and thereafter lock the pin in the hole in a second direction, by turning the first and second parts in relation to each other. The two parts can be interconnected to form the medical device, as shown in FIG. 29*b*, before or during a surgical procedure, preferably the parts are jointed during the surgical procedure since this enables the parts to be introduced into the hip joint through a hole smaller than a hole which through which the interconnected medical device could pass. The cross section A-A of FIG. 29*c* shows a pin 1218 in a hole 1219 after it firstly has been introduced in one direction and secondly been turned to lock the pin 1218 in the hole 1219.

FIG. 30*a* shows the medical device according to an embodiment where the medical device comprises an artificial caput femur 45, a fixating member 608, and a stabilizing member 612 adapted to stabilize the medical device from the outside of the collum femur 6, substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The medical device comprises two parts which are adapted to be interconnected to form an interconnected medical device, as shown in FIG. 30*b*. The first part of the medical device comprises a first part of the fixating member 608', and a first part of the caput femur surface 45'. The second part of the medical device comprises a second part of the fixating member 608", and a second part of the caput femur surface 45". The first part of the medical device comprises a hole 1221 which are adapted to receive a pin 1220 in a first direction and thereafter lock the pin 1220 in the hole 1221 in a second direction, by turning the first and second parts in relation to each other. The two parts can be interconnected to form the medical device, as shown in FIG. 30*b*, before or during a surgical procedure, preferably the parts are jointed during the surgical procedure since this enables the parts to be introduced into the hip joint through a hole smaller than a hole which through which the interconnected medical device could pass. The cross section A-A of FIG. 30*c* shows a pin 1220 in a hole 1221 after it firstly has been introduced in one direction and secondly been turned to lock he pin 1220 in the hole 1221.

FIG. 31*a* shows an embodiment in which a flexible first layer 1222 is applied onto the caput femur 5. The flexible first layer 1222 is adapted to serve as a layer for fixation of a second stiff layer, acting as an artificial acetabulum surface 45. The flexible first layer 1222 could for example be fixated to the caput femur 5 using an adhesive.

FIG. 31*b* shows the hip joint with the caput femur 5, when the flexible first layer 1222 has been applied thereon. The flexible first layer 1222 can further be adapted to go beyond the maximum diameter of the caput femur 5.

FIG. 32*a* shows an example of a stiff artificial caput femur surface 45 comprising multiple artificial caput femur surface parts 46. The multiple artificial caput femur surface parts 46 are adapted to be connected to an interconnecting artificial caput femur surface part 56 after insertion into a hip joint. The interconnecting artificial caput femur surface part 56, which serves as a base part, comprises self locking connecting members 57, shown in FIG. 32*b*, that fits with corresponding self locking members 58 of the artificial caput femur surface parts 46. The artificial caput femur surface parts 46 create an artificial caput femur surface 45 when connected to each other. The self locking members 57,58 can be assisted or replaced by screws, welding, sprints, band, adhesive or some other mechanical connecting member. The artificial caput femur surface 45 according to this embodiment can further be adapted to go beyond the maximum diameter of the caput femur 5.

FIG. 33 shows the parts being applied to the caput femur 5 with the flexible first artificial layer 1222 placed thereon. The flexible first layer 1222 could be adapted to even-out the surface of the caput femur 5 for achieving a better fixation of the stiff second layer, acting as an artificial caput femur surface 45, or to act as a resilient member when the hip joint is in its functional position for absorbing shocks placed on the hip joint.

FIG. 34 shows the caput femur 5 when the stiff artificial caput femur surface 45 is completed and fixated on top of the first flexible layer 1222. The stiff layer is preferably made of a hard material for resisting the wear that is created by the connection with the acetabulum 8, or an artificial replacement therefore. The stiff second layer 45 could be fixated to the first flexible layer 1222 using an adhesive, form fitting or a mechanical fixation element. The second stiff layer 45 according to this embodiment can further be adapted to go beyond the maximum diameter of the caput femur 5.

Figure 35:
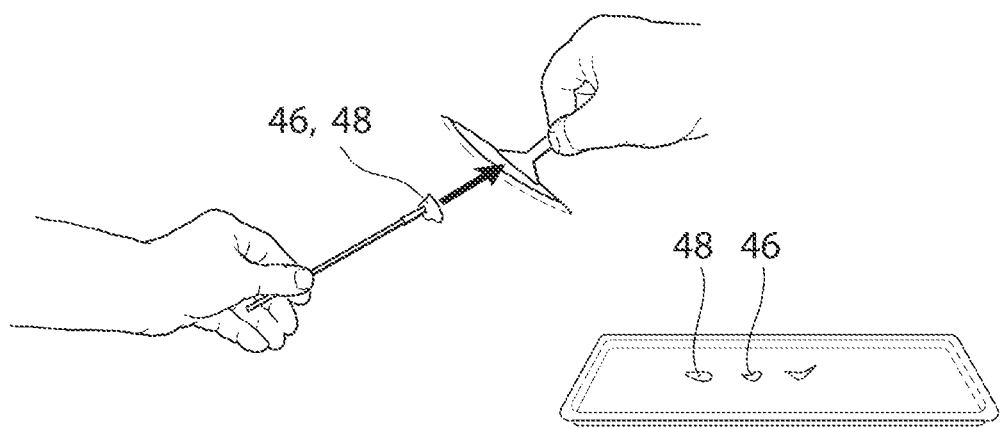
FIG. 35 shows the insertion of artificial hip joint surface parts in the surgical method.

FIG. 35 shows the artificial hip joint surface parts 48 according to any of the embodiments being inserted through an incision according to a surgical method. According to a first embodiment the artificial hip joint surface parts 48 are artificial caput femur surface parts 46, adapted to be connected to each other after the insertion to form an artificial caput femur surface 45.

Figure 36:
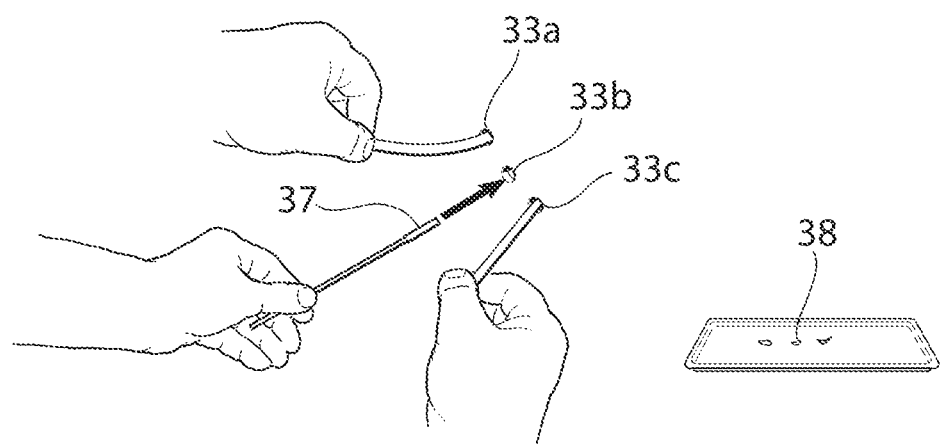
FIG. 36 shows a step of the laparoscopic/arthroscopic method in further detail.

FIG. 36 shows the artificial hip joint surface parts 48 according to any of the embodiments being inserted through laparoscopic/arthroscopic trocars 33a,b,c, through a small incision according to a laparoscopic/arthroscopic method. According to a first embodiment the artificial hip joint surface parts 48 are artificial caput femur surface parts 46, adapted to be connected to each other after the insertion to form an artificial caput femur surface 45.

A surgical and laparoscopic/arthroscopic method of treating hip joint osteoarthritis by providing a hip joint surface through the pelvic bone of a human patient from the opposite side from acetabulum is further provided. Said method will now be described in further detail.

Figure 37:
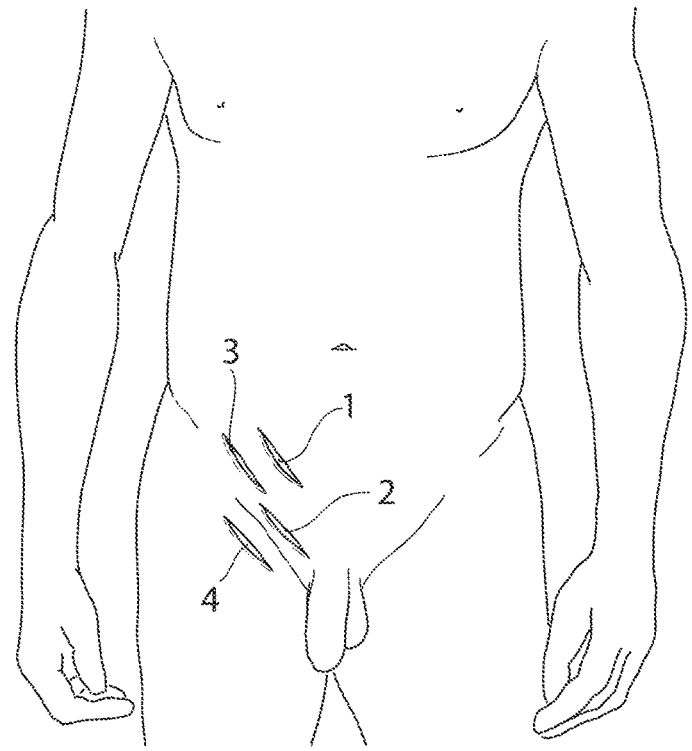
FIG. 37 shows different locations of the incisions made in the human body in the surgical method.

FIG. 37 shows a frontal view of the body of a human patient. A surgical method of operating the hip joint from the opposite side from acetabulum 8 is according to a first embodiment performed starting with an incision 1 in the abdominal wall of the human patient. The incision 1 passes through the abdominal wall, including peritoneum in to the abdomen of the human patent. In a second preferred embodiment the incision 2 is conducted through the abdominal wall and into the pelvic area, below the peritoneum abdominal sac. According to a third embodiment the incision 3 is performed just between Illium of the pelvis bone and the surrounding tissue, an incision 3 which could enable the pelvic bone 9 to be dissected with very little penetration of fascia and muscular tissue. According to a fourth embodiment the incision 4 is made in the inguinal region. In all of the four embodiments the tissue surrounding the pelvic bone 9 in the area opposite to acetabulum 8 is removed or penetrated or divided or moved away which enables the surgeon to reach the pelvic bone 9. It is obvious that the methods described may both be combined or altered reaching the same goal to dissect the pelvic bone 9 on the opposite side of the acetabulum 8.

Figure 38:
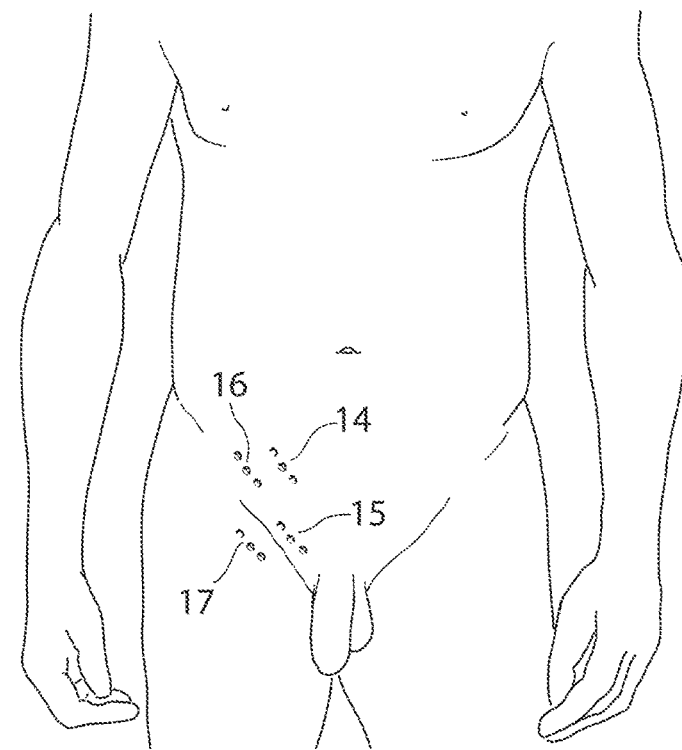
FIG. 38 shows different locations where small incisions can be made in the human body in the laparoscopic/arthroscopic method.

FIG. 38 shows a frontal view of the body of a human patient. A laparoscopic/arthroscopic method of operating the hip joint, from the opposite side from acetabulum 8 is according to a first embodiment performed starting with making small incisions 14 in the abdominal wall of the human patient. The small incisions enable the surgeon to insert laparoscopic/arthroscopic trocars into the abdomen of the human patient. According to the first embodiment the incisions 14 passes through the abdominal wall, and peritoneum in to the abdomen of the human patent. According to a second preferred embodiment the small incisions 15 is conducted through the rectus abdominis or on the side thereof and in to the pelvic area, below peritoneum. According to a third embodiment the small incisions 16 is performed just between Illium of pelvis and the surrounding tissue, an incision 16 which could enable the pelvic bone to be dissected with very little penetration of fascia and muscular tissue. According to a fourth embodiment the incision 17 is made in the inguinal region. In all of the four embodiments the tissue surrounding the pelvic bone 9 in the area opposite to acetabulum 8 is removed or penetrated or divided or moved away which enables the surgeon to reach the pelvic bone 9.

Figure 39:
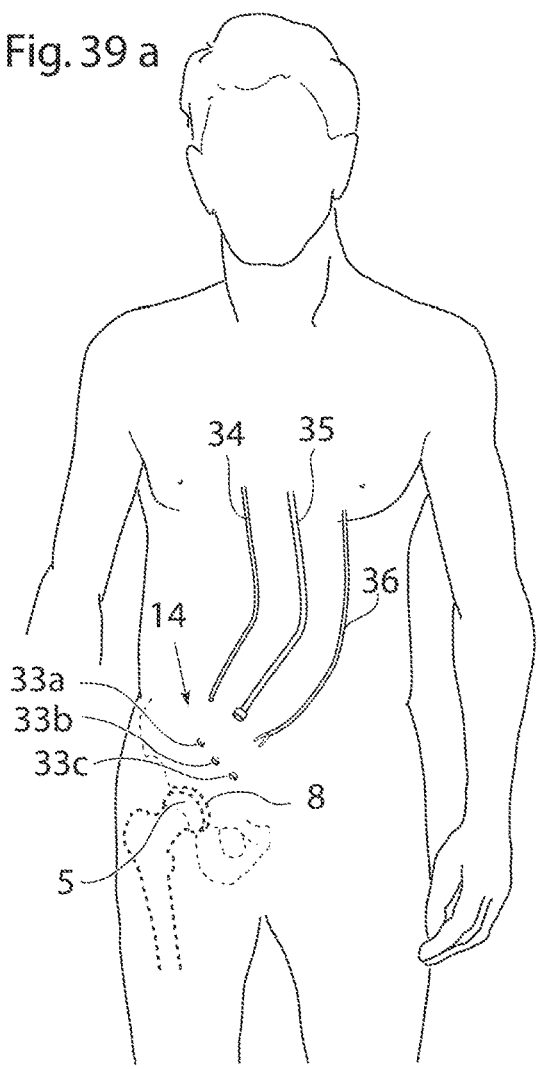
FIG. 39a shows the laparoscopic/arthroscopic method of operating the hip joint of a human patient.
FIG. 39b shows a lateral view in section of the laparoscopic/arthroscopic method.
Figure 39:
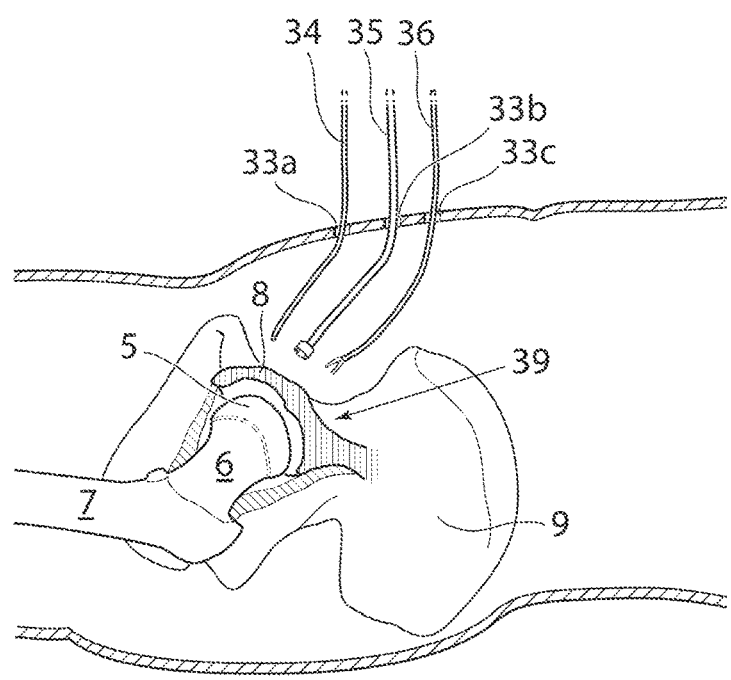

FIG. 39a shows a frontal view of the body of a human patient, illustrating the laparoscopic/arthroscopic method of operating the hip joint from the opposite side from acetabulum 8. The hip joint comprises the acetabulum 8 and the caput femur 5. The small incisions 14 in the abdominal wall of the human patient allows the insertion of laparoscopic/arthroscopic trocars 33a,b,c into the body of the patients. Whereafter one or more camera 34, a surgical instrument adapted to create a hole in the pelvic bone 35, or instruments 36 for dissecting, introducing, placing, connecting, attaching, creating or filling prosthesis or prosthetic parts, can be inserted into said body through said laparoscopic/arthroscopic trocars 33a,b,c.

FIG. 39b shows a lateral cross-sectional view of the body of a human patient, with the hip joint shown in section in further detail. The hip joint comprises a caput femur 5 placed at the very top of collum femur 6 which is the top part of the femoral bone 7. The caput femur 5 is in connection with the acetabulum 8 which is a bowl shaped part of the pelvic bone 9. Laparoscopic/arthroscopic trocars 33a,b,c is being used to reach the hip joint 39 with one or more camera 34, a surgical instrument adapted to create a hole in the pelvic bone 35, or instruments 36 for dissecting, introducing, placing, connecting, attaching, creating or filling prosthesis or prosthetic parts.

Figure 19C:
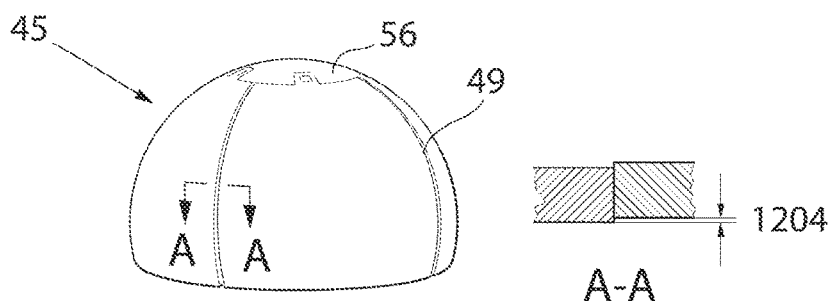
FIG. 19c shows the artificial caput femur surface according to 19a when assembled.

After dissecting the pelvic bone 9 a hole 18 is created in the bone 9, shown in FIG. 19. The hole 18 passes through the pelvic bone 9 from the opposite side from acetabulum 8 and into the hip joint 19.

Figure 40:
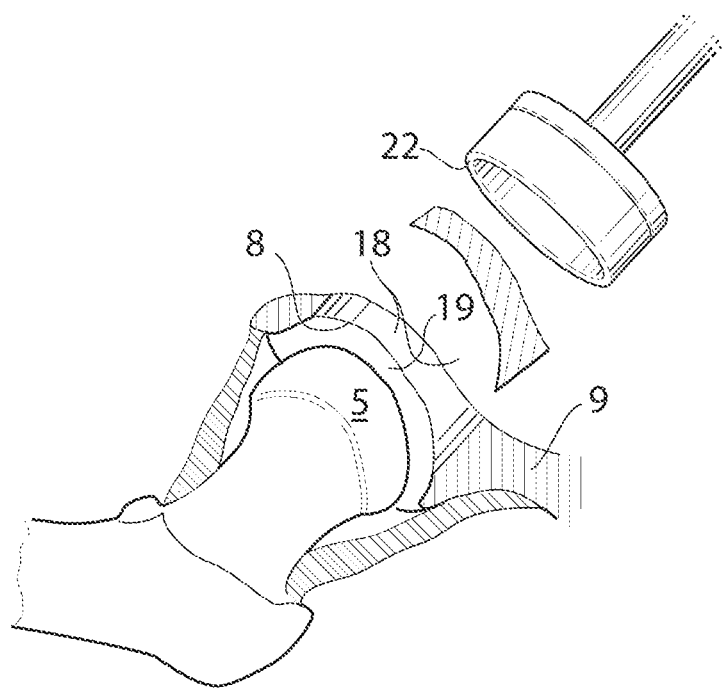
FIG. 40 shows the hip joint in section when a hole is created in the pelvic bone.

FIG. 40 shows the hole 18 in the pelvic bone 9 according to a first embodiment, the hole 18 is large which allows prosthesis to pass through said hole 18 in their full functional size. According to a second embodiment the hole 20 created in the surgical or laparoscopic/arthroscopic method is much smaller as shown in FIG. 41 allowing the surgical instrument creating the hole to be smaller, and thus the incision and dissection performed in the human body.

Figure 41:
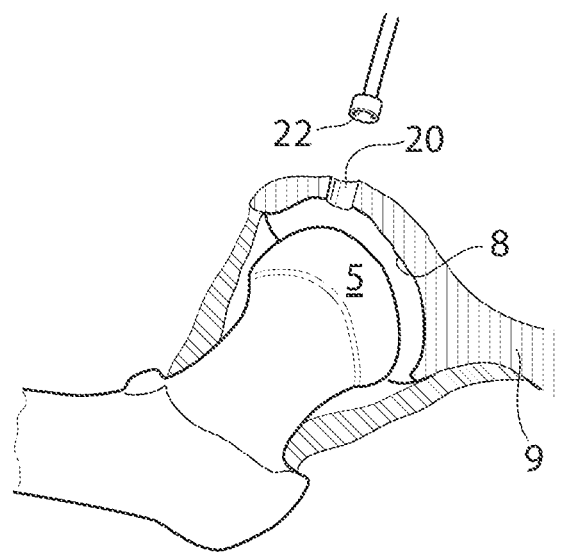
FIG. 41 shows the hip joint in section when a small hole is created in the pelvic bone.

FIG. 41 shows a surgical instrument for creating a hole 18, 20 in the pelvic bone 9a according to a first embodiment. The surgical instrument comprises a driving member 21a, b. The driving member 21a,b could be a shaft, a rod, a belt, a chain or any other element suitable for transferring force or torque. The surgical instrument also comprises a bone contacting organ 22 which is adapted to create the hole 18, 20 in the pelvic bone 9. The bone contacting organ 22 could have a sawing, drilling or milling effect using sharp objects; it is furthermore conceivable that said bone contacting organ 22 creates a hole using water, abrasive fluids, laser or radiation. The surgical instrument also comprises an operating device 23a adapted to operate the driving member 21a,b. The operating device could comprise an electrical, mechanical, pneumatic or magnetic motor and it could be adapted to create a rotating, oscillating, vibrating or repetitive movement. The operation device may include a source of ultrasound, radiation, laser or water.

Figure 42:
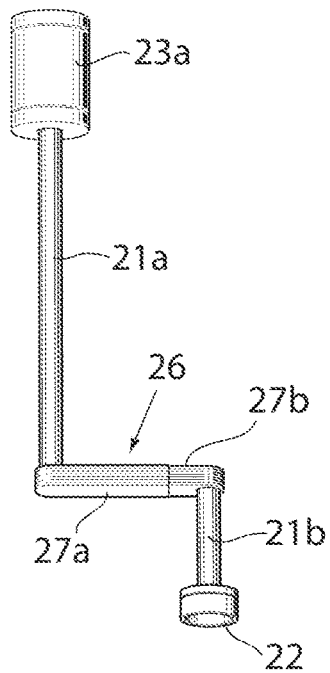
FIG. 42 shows the instrument that creates a hole in the pelvic bone according to a first embodiment.

FIG. 42 shows a surgical instrument that further comprises a parallel displaced part or section 26. The parallel displaced part or section 26 improves the reach of the medical device and enables the creation of a hole 18 in the pelvic bone 9 from the opposite side from acetabulum 8. According to one embodiment shown in FIG. 42 the parallel displaced part or section 26 has a telescopic function by means of the parallel displaced part or section 26 being divided in to a first and second part 27a, b, wherein the second part 27b can slide in and out of the first part 27a.

Figure 43:
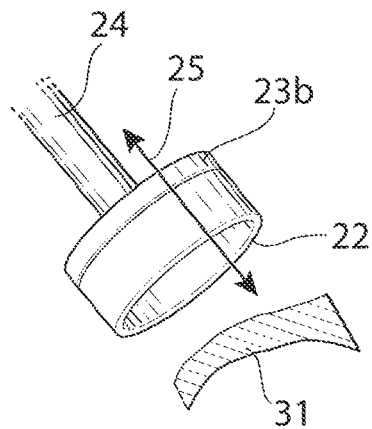
FIG. 43 shows the instrument that creates a hole in the pelvic bone according to a first embodiment in further detail.

FIG. 43 shows one embodiment in which the operating device 23b is be placed in direct connection with the bone contacting organ 22, in which case the operating device 23b also serves as driving member. In this construction a handle portion 24 could be attached to the surgical instrument, facilitating the surgeons handling of said surgical instrument. To improve the reach of the surgical instrument the handle portion 24 could be attached perpendicular to the hole-creating direction 25 of the surgical instrument, it is furthermore conceivable that the handle portion 24 is bent by means of a parallel displaced part or section, a fixed angle, an adjustable angle or a flexible part or section.

Figure 44:
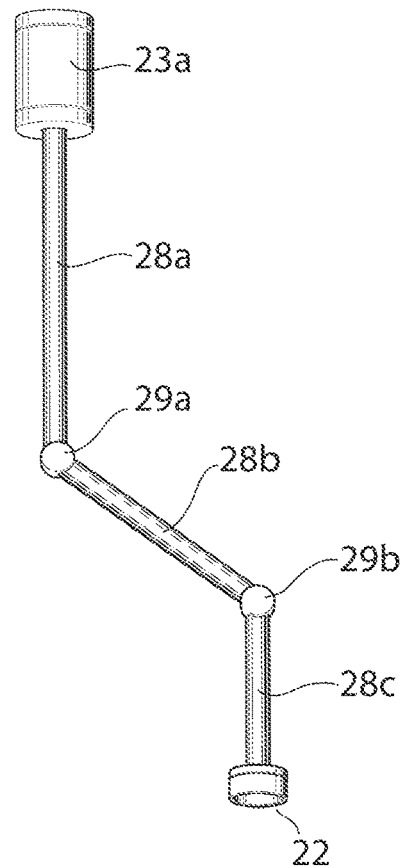
FIG. 44 shows the instrument that creates a hole in the pelvic bone according to a second embodiment.

FIG. 44 shows the surgical instrument according to a second embodiment wherein said surgical instrument comprises a driving member 28a,b,c with two angle adjusting members 29a,b. The angle adjusting members 29a,b could be adjustable for varying the angle of said driving member 28a,b,c or fixed in an angle suitable for creating a hole in the pelvic bone 9 from the opposite side from acetabulum 8. In another embodiment (not shown) the part of the driving member 28c in connection with the bone contacting organ 22 could be very short enabling the surgical instrument to operate very close to the pelvic bone 9 when creating a hole 18 in said pelvic bone 9.

Figure 45:
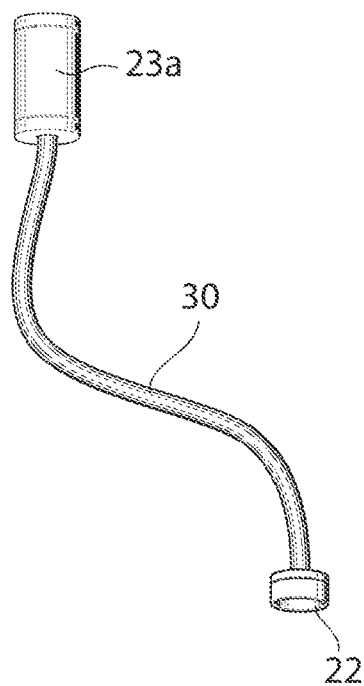
FIG. 45 shows the instrument that creates a hole in the pelvic bone according to a third embodiment.

FIG. 45 shows the surgical instrument according to a third embodiment wherein the driving member 30 is flexible, enabling said driving member 30 to be very precisely adjusted to create a hole 18 in the pelvic bone 9 of the patient. The stiffness of said driving member 30 could range from completely flexible to completely stiff to fit the surroundings of the particular operation.

Figure 46:
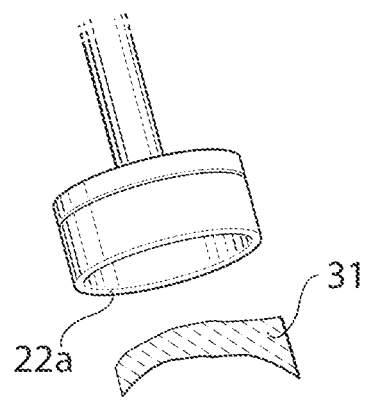
FIG. 46 shows the bone contacting organ according to a first embodiment.

FIG. 46 shows the bone contacting organ according to a first embodiment wherein the bone contacting organ 22a is adapted to crate a bone plug 31. The bone plug 31 could be adapted to be replaced into said hole 18 after the surgical or laparoscopic/arthroscopic steps performed in the hip joint has been concluded.

Figure 47:
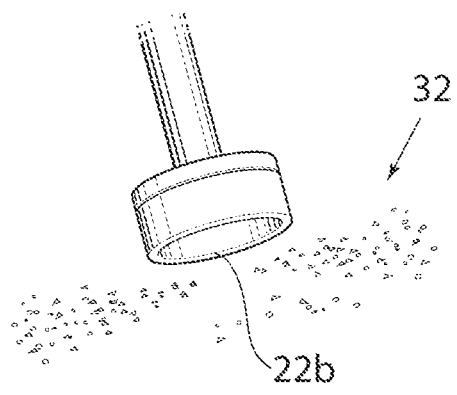
FIG. 47 shows the bone contacting organ according to a second embodiment.

FIG. 47 shows the bone contacting organ according to a second embodiment wherein the bone contacting organ 22b is adapted to create small pieces of bone 32 when creating said hole 18 in the pelvic bone 9. The small pieces of bone could be transported from the area and out of the body using vacuum power or a hydraulic transport system.

Figure 48:
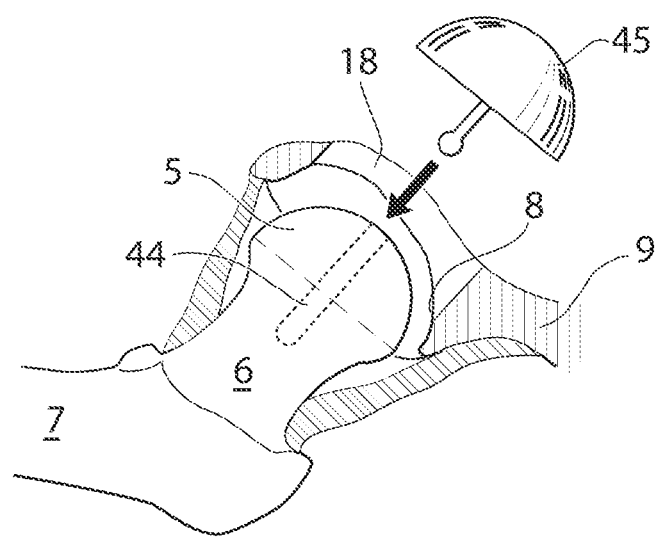
FIG. 48a shows the step of providing an artificial caput femur surface.
FIG. 48b shows the a section of the hip joint after the artificial caput femur surface has been provided.
Figure 48:
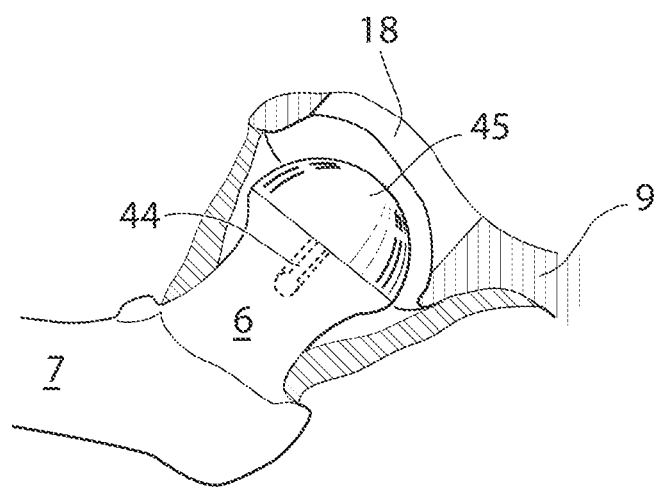

FIG. 48a shows the hip joint in section with the caput femur 5 placed at the very top of collum femur 6, which is the top part of the femoral bone 7. The caput femur is in connection with the acetabulum 8, which is a bowl shaped part of the pelvic bone 9. According to a first embodiment the hole 18 created in the pelvic bone 9 from the opposite side from acetabulum 8, is larger than said artificial caput femur surface 45, enabling the insertion of said artificial caput femur surface 45 in its full functional size. Said insertion of said artificial caput femur surface 45 could be performed as a step of the surgical method, as well as a step of the laparoscopic/arthroscopic method. After the insertion, the artificial caput femur surface 45 is attached to the caput femur 5, the attaching is performed by means of a mechanical attachment 44 comprising a shaft or screw penetrating the cortex. It is however also conceivable that the mechanical attachment 44 is assisted or replaced by bone cement or adhesive placed between caput femur 5 and the artificial caput femur surface 45, or in connection with said shaft or screw 44. Alternative ways of attaching the artificial caput femur surface 45 includes: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

FIG. 48b shows the hip joint in section with the artificial caput femur surface 45 attached to the caput femur 5.

The surgical and laparoscopic/arthroscopic methods described could further comprise the step of reaming the acetabulum 8 or the caput femur 5. According to a first embodiment the reaming of the acetabulum 8 or the caput femur is performed using an expandable reamer shown in FIGS. 49-51. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 49:
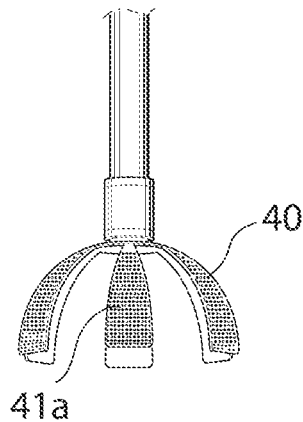
FIG. 49 shows the expandable reamer.
Figure 50:
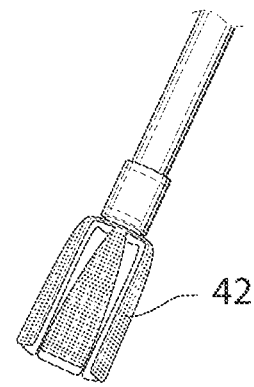
FIG. 50 shows the expandable reamer in its folded state.

FIG. 50 shows the expandable reamer, according to any of the embodiments, wherein the reaming blades 40 can be folded towards a center of the semi-sphere that the expandable reamer produces in its expanded state, shown in FIG. 49. The folding of the reaming blades 40 enables the expandable reamer to be introduced into a hip joint through a hole smaller than the area possible to ream using said expandable reamer.

Figure 51:
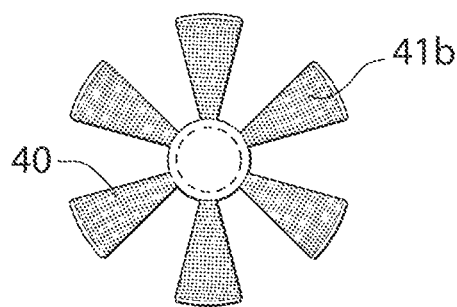
FIG. 51 shows the expandable reamer from underneath.

FIG. 51 shows the interior said of the expandable reamer with the reaming blades 40. In the embodiment when the expandable reamer is adapted to ream the caput femur, said interior side of the at least one reaming blade 40 comprises a reaming surface 41b.

Figure 52:
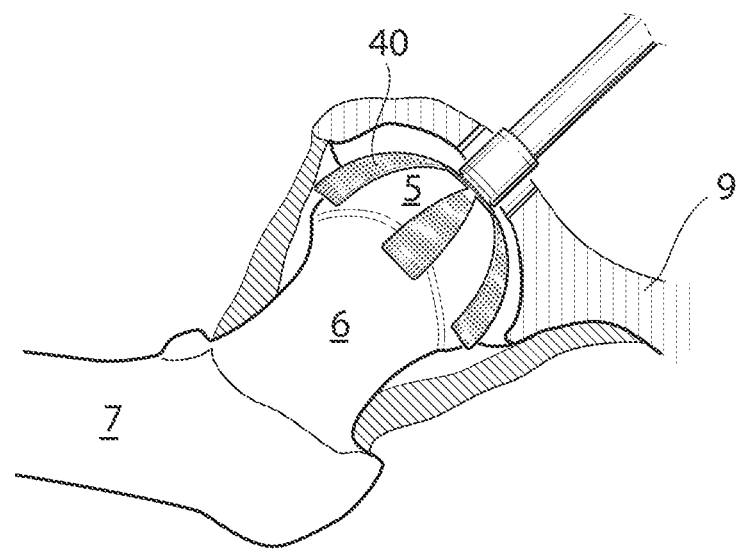
FIG. 52 shows the expandable reamer being used in the surgical or laparoscopic/arthroscopic method.

FIG. 52 shows the expandable reamer according to any of the embodiments when reaming said acetabulum 8 and/or said caput femur 5. The reamer can be adapted to be operated manually or by means of a rotating, vibrating or oscillating operating device.

According the one embodiment the bone contacting organ 22 of the surgical instrument for creating a hole in the pelvic bone can be replace with the expandable reamer shown in FIGS. 49-51, in which case the expandable reamer can be powered using the operating device 23a,b used in said surgical instrument.

After the preparation of the hip joint surfaces the method step of inserting or creating new surfaces is performed.

Figure 53:
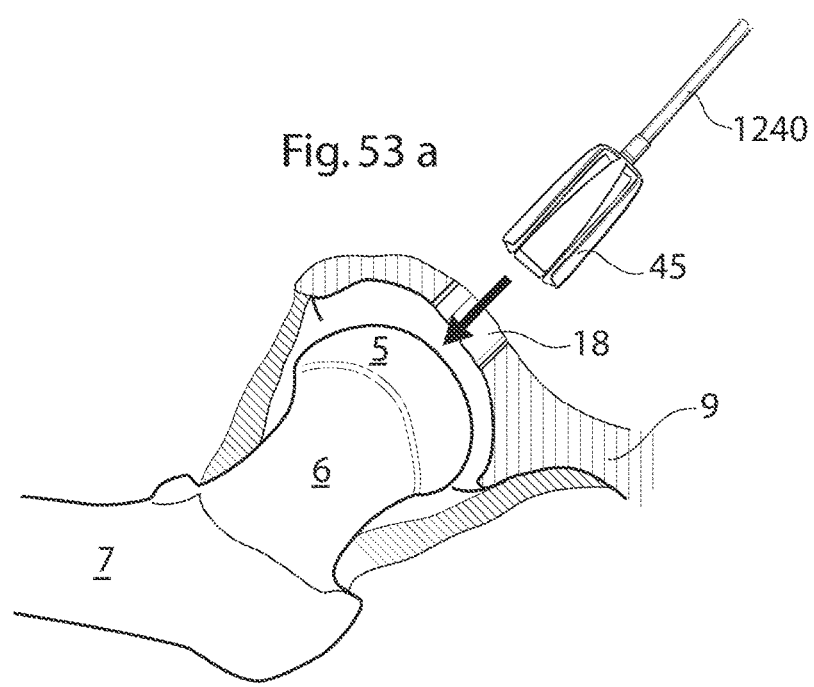
FIG. 53a shows an expandable artificial caput femur surface, according to the second embodiment, when travelling through a hole in the pelvic bone.
FIG. 53b shows an expandable artificial caput femur surface, according to the second embodiment, when being placed on the caput femur.
FIG. 53c shows an expandable artificial caput femur surface, according to the second embodiment, when placed on the caput femur.
Figure 53:
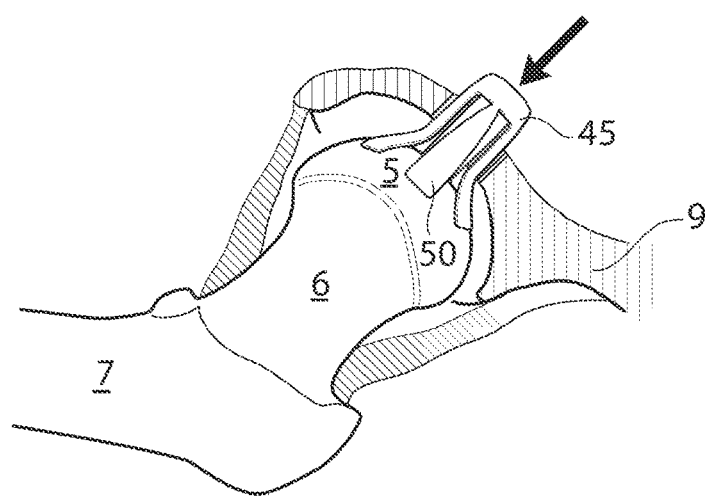
Figure 53:
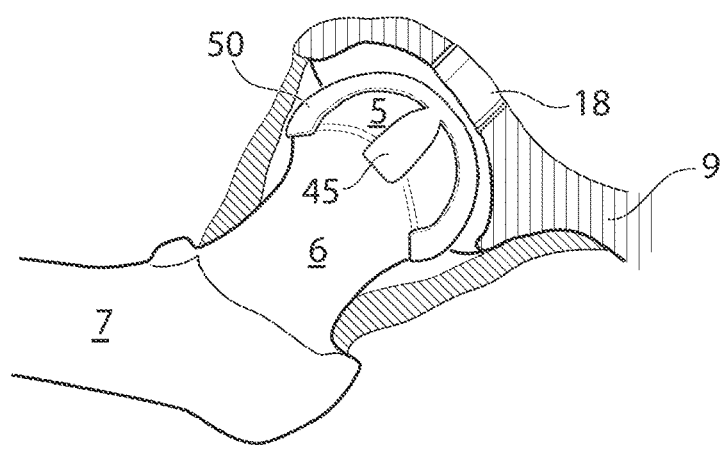

FIG. 53a shows how an expandable artificial caput femur surface 45 is being inserted through a hole 18 in the pelvic bone 9, using a tool for insertion of a medical device 1240.

FIG. 53b shows how an expandable artificial caput femur surface 45 goes through the hole 18 in the pelvic bone 9 and travels over caput femur 5, by means of arms 50 of the artificial caput femur surface making the artificial caput femur surface flexible.

FIG. 53c shows an expandable artificial caput femur surface 45 is after it has been placed on said caput femur 5. In this embodiment the artificial caput femur surface arms 50 clasps the caput femur 5.

The medical device according to any of the embodiments could have the size of the largest diameter, largest radius or a largest cross-sectional distance being variable such that the medical device can be introduced through a hole 18 having a cross sectional area smaller than 530 mm2 or smaller than 380 mm2 or smaller than 250 mm2 or smaller than 180 mm2 or smaller than 110 mm2.

Figure 54:
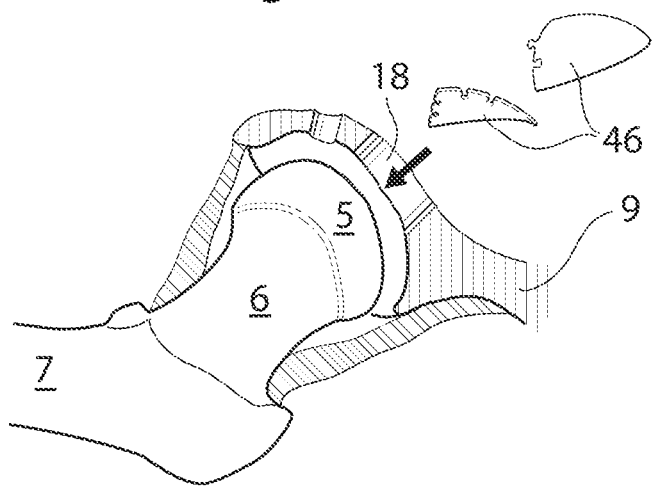
FIG. 54a show the insertion of artificial caput femur surface parts into the hip joint.
FIG. 54b shows the artificial caput femur surface parts after they have been connected inside of the hip joint forming an artificial caput femur surface.
FIG. 54c shows how the form of the artificial caput femur surface parts enables the connection of the artificial caput femur surface parts to form an artificial caput femur surface.
FIG. 54d shows a camera being inserted into the hip joint.
Figure 54:
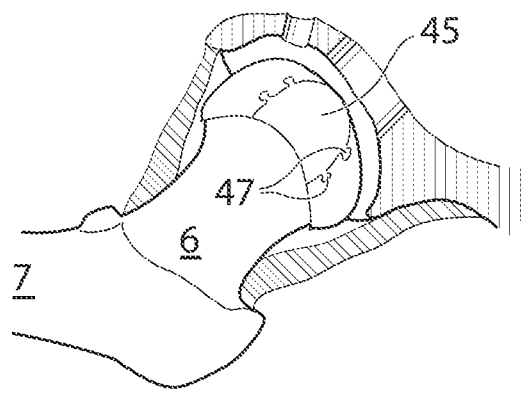
Figure 54:
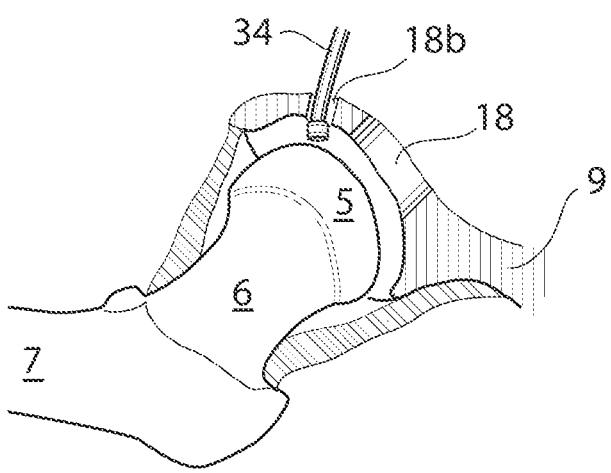
Figure 54:
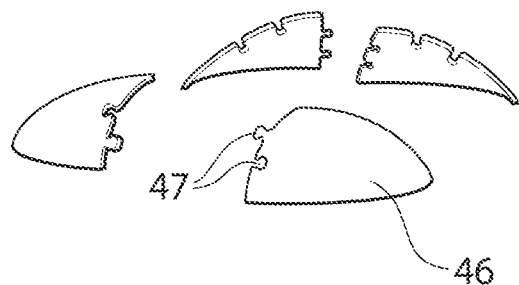

FIG. 54a shows the hip joint in section according to a second embodiment in which the hole 18 in the pelvic bone 9 is smaller than the artificial caput femur surface 45 in its full functional size. According to this embodiment the artificial caput femur surface 45 is introduced into said hip joint through the hole 18 in the pelvic bone 9 form the opposite side from acetabulum 8. The artificial caput femur surface parts 46 are connected to each other after insertion into said hip joint to form the artificial caput femur surface 45.

FIG. 54b shows the hip joint in section when the artificial caput femur surface parts 46 are connected to each other using form fitting 47, however it is conceivable that the form fitting is assisted or replaced with adhesive or bone cement. After the artificial caput femur surface parts 46 have been introduced and connected in the hip joint, they are mechanically fixated to the caput femur 5, the mechanical fixation could be done by means of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

FIG. 54c shows the artificial caput femur surface parts 46 with the parts supplying the form fitting 47 for connecting the parts to each other.

FIG. 54d shows the hip joint in section wherein a second hole 18b in the pelvic bone 9 enables the surgeon to place a camera 34 into the hip joint, preferably used in the laparoscopic/arthroscopic method.

Figure 55:
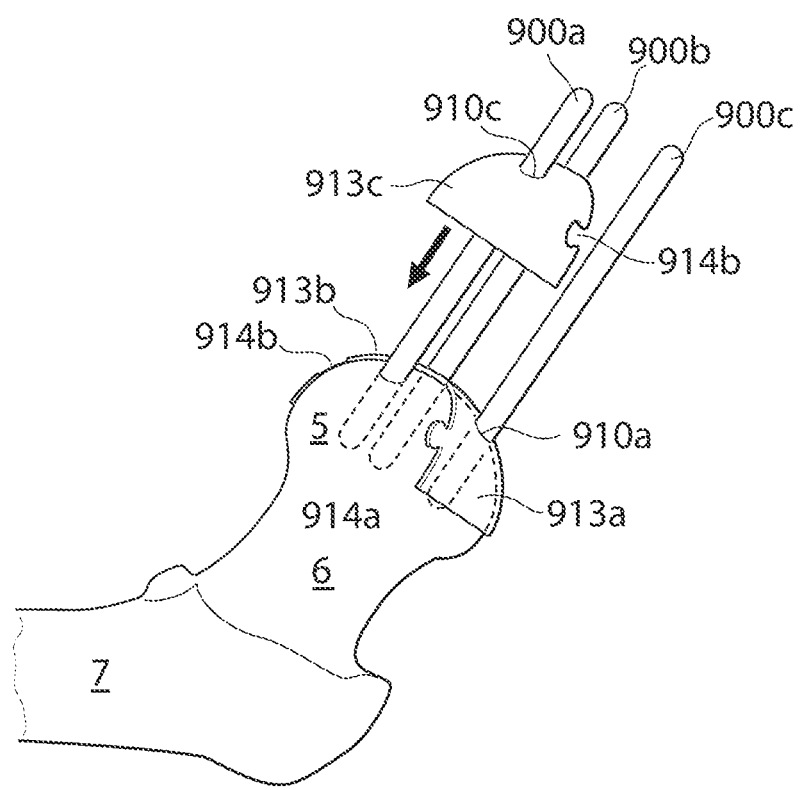
FIG. 55a shows the hip joint when a medical device comprising multiple parts is being provided.
FIG. 55b shows the hip joint when a medical device comprising multiple parts is being provided, in a top view.
Figure 55:
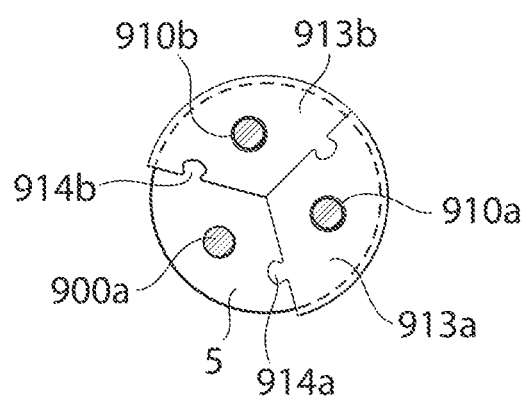

FIG. 55a shows the femoral bone 7 where multiple positioning shafts 900a,b,c are placed in the caput femur 5. The positioning shafts 900a,b,c are adapted to guide, position and center artificial hip joint surface parts 913a,b on to the caput femur 5, or guide, position and center artificial hip joint surface parts 913a,b to be placed in the acetabulum. The artificial hip joint surface parts 913a,b each have a positioning hole 910a,b which are adapted to encircle the positioning shafts 900a,b,c placed in the caput femur 5. The artificial hip joint surface parts 913a,b are adapted to be connected to each other after insertion the hip joint using mechanical connecting members 914a,b, wherein the mechanical connecting members comprises a first part 914a placed in a first artificial hip joint surface part 913b and adapted to fit in a corresponding second part 914b, placed in a second artificial hip joint surface part 913a. The multiple positioning shafts 900a,b thereby assists in the connection of multiple artificial hip joint surface parts 913a,b to each other. However the mechanical connecting members 914a,b could be assisted or replaced by an adhesive.

FIG. 55b shows the positioning of the artificial hip joint surface parts 913a,b from above with the positioning holes 910a,b of the artificial hip joint surface parts 913a,b encircling the positioning shafts 900a,b,c and thereby the positioning shafts 900a,b,c guiding, positioning and centering the artificial hip joint surface parts 913a,b in the hip joint.

Figure 56:
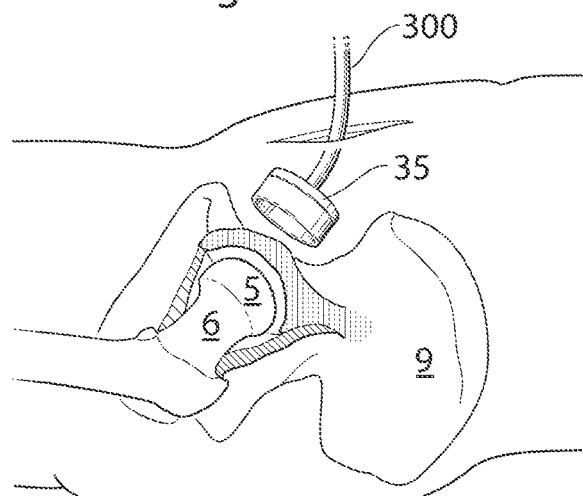
FIG. 56 shows the human patient in section when a medical device adapted to create a hole in the pelvic bone is provided.

FIG. 56 shows a lateral view of a human patient where a surgical instrument 35 adapted to create a hole in the pelvic bone from the abdominal side of the pelvic bone 9 is inserted through an incision in the abdominal wall. The surgical instrument could comprise a flexible part or section 300, enabling the surgical instrument to be very precisely adjusted to reach the pelvic bone or the hip joint from the abdominal side of the pelvic bone. The stiffness of said flexible part or section 300 could range from completely flexible to completely stiff to fit the surroundings of the particular operation. The surgical instrument 35 could be powered through an operating device which in turn could comprise an electrical, hydraulic, mechanical, pneumatic or magnetic engine and it could be adapted to create a rotating, oscillating, vibrating or repetitive movement.

According to another embodiment (not shown) the surgical instrument 35 is powered from an operating device being placed outside of the human body, in the thigh region. The force created in the operating device is then transferred through a force transferring member placed which is placed in the collum femur and femoral bone. This allows the surgeon to supply force to an area of the hip joint and its surroundings through an incision in the thigh.

Figure 57:
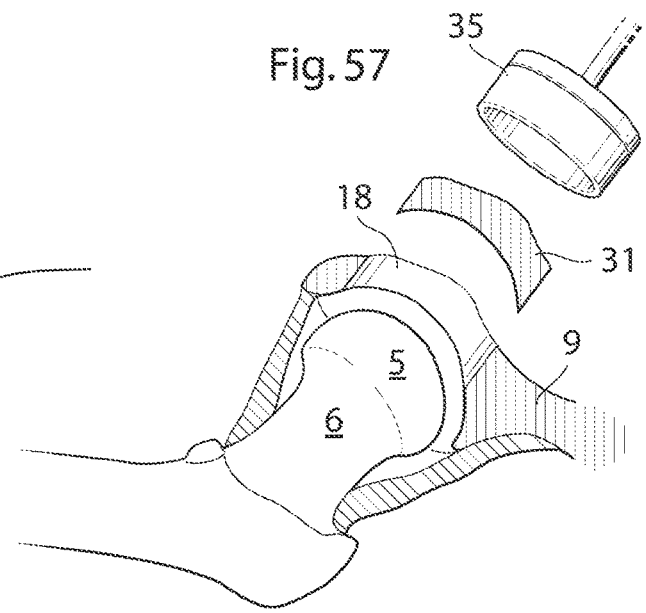
FIG. 57 shows the hip joint in section when a hole is being created in the pelvic bone.

FIG. 57 shows a hip joint in section wherein a surgical instrument 35 adapted to create a hole 18 in the pelvic bone 9 is adapted to create a bone plug 31. The bone plug 31 could be adapted to be replaced into said hole 18 after the surgical or laparoscopic steps performed in the hip joint has been concluded.

Figure 58:
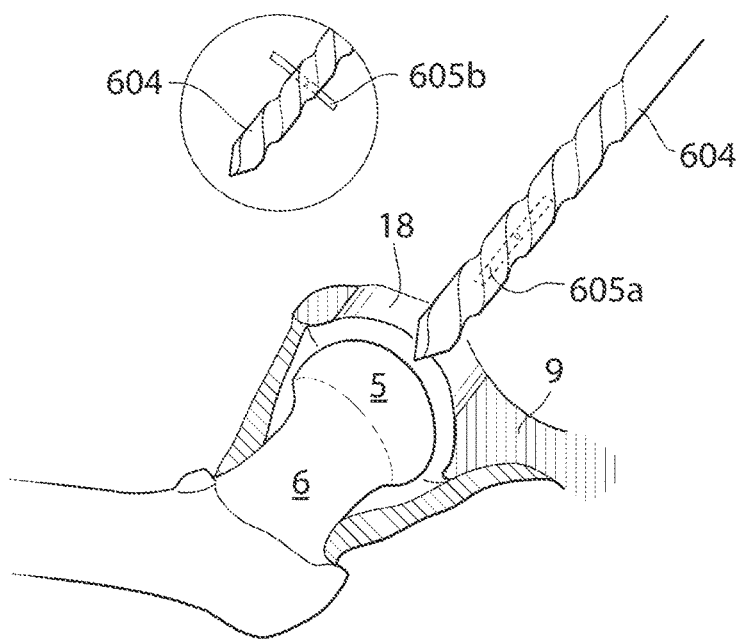
FIG. 58 shows the hip joint in section when a surgical instrument for removing the caput femur is provided.

FIG. 58 shows a hip joint in section wherein a surgical instrument 604 for removing the caput femur 5 is provided through a hole 18 in the pelvic bone 9. The surgical instrument is adapted to create a hole in the caput femur 5, passing down a longitudinal extension of the collum femur 6. The surgical instrument further comprises a sawing member 605a,b adapted to separate the caput femur from the collum femur. In a first state 605a, the sawing member 605a is retracted within the surgical instrument 604. When the surgical instrument is positioned inside of the collum femur in a desired position the sawing member is folded to a second state 605b allowing the sawing member to create a section in the collum femur, separating the caput femur 5 from the collum femur 6.

Figure 59:
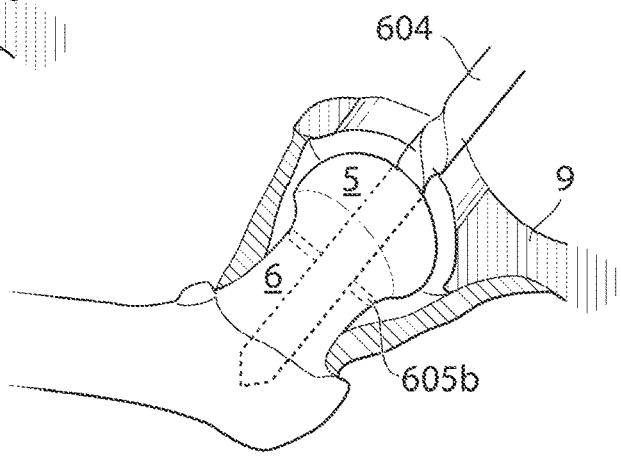
FIG. 59 shows the hip joint in section when a surgical instrument for removing the caput femur is positioned inside of the caput and collum femur.

FIG. 59 shows the hip joint in section when the surgical instrument 604 and the sawing member 605b is positioned inside of the collum femur. After the caput femur 5 has been removed, a stabilizing part of the collum femur 6 is retained. The stabilizing part of collum femur 6 could be defined to be the proximal half of said collum femur 6, the proximal two third of said collum femur, the proximal three quarter of said collum femur, the proximal 90% of said collum femur or the whole collum femur. The proximal part of collum femur being the part of collum femur closest to the torso of the human body.

FIG. 60-64 shows the medical device and the method of placing said medical device according to a one embodiment.

Figure 60:
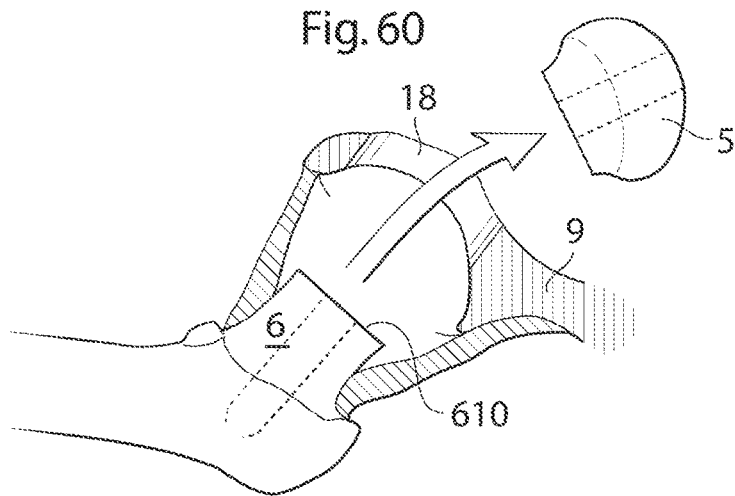
FIG. 60 shows the removing of the caput femur through a hole in the femoral bone.

FIG. 60 shows the removal of the caput femur 5 after the surgical instrument 604 has created a surface of a section 610 substantially perpendicularly to the longitudinal extension of the collum femur 6. The separated caput femur 5 is then removed through the hole 18 in the pelvic bone 9.

Figure 61:
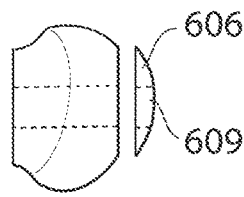
FIG. 61 shows the removing of a part of a piece of bone from the caput femur.

FIG. 61 shows the removal of a piece of bone 609 from the caput femur 5. The removal of the piece of bone 609 is preferably performed outside of the human body. FIG. 13 shows the removal of the top part of caput femur 5; however it is equally conceivable that the piece of bone is removed from any other side of the caput femur 5.

Figure 62:
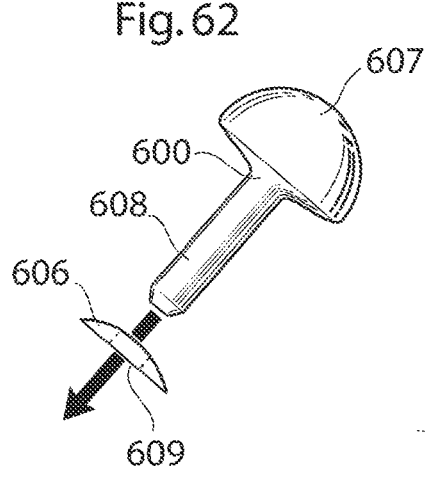
FIG. 62 shows the piece of bone being placed on the medical device.

FIG. 62 shows the medical device 600 according to one embodiment. The medical device comprises a fixating member 608 and an artificial caput femur surface 607. The artificial caput femur surface 607 is adapted to be in contact with the acetabulum surface 11 or an artificial replacement therefore. The fixating member 608 is adapted to at least partly be stabilized by the cortical bone 601 of a stabilizing part of the collum femur 6. The stabilizing could be performed from the inside, substantially perpendicular to the longitudinal extension of the collum femur 6, and from the acetabulum side, substantially in line with the longitudinal extension. The stabilizing could further be performed from the acetabulum side, substantially in line with the longitudinal extension of the collum femur 6, and from the outside, substantially perpendicular to the longitudinal extension of the collum femur 6, from the inside, substantially perpendicular to the longitudinal extension of the collum femur 6, and from the outside, substantially perpendicular to the longitudinal extension of the collum femur 6, or from the acetabulum side, substantially in line with the longitudinal extension of the collum femur 6, and from the outside, substantially perpendicular to the longitudinal extension of the collum femur 6. The medical device 600 could be adapted to at least partly be directly stabilized by the cortical bone 601 of said stabilizing part of said collum femur 6, or to be indirectly stabilized by the cortical bone 601 of said stabilizing part of said collum femur 6. In the embodiments (not shown) when the medical device 600 is indirectly stabilized by the cortical bone 601 of the collum femur 6 it is conceivable that a material is placed between said cortical bone 601 and the fixating member 608 of the medical device 600. The material could be: bone cement, an at least partly elastic material, glue, adhesive, antibiotic, biocompatible plastic material, biocompatible ceramics and/or a biocompatible metal such as titanium or tantalum.

The hole 609 in the piece of bone 606 from the caput femur 5 is preferably the hole created by the surgical instrument 604 in the process of removing the caput femur, however it is conceivable that the hole 609 needs to be altered or adapted for fitting the fixating member 608 which is adapted to be placed inside of the hole 609 in the piece of bone 606 removed from the caput femur 5.

Figure 63:
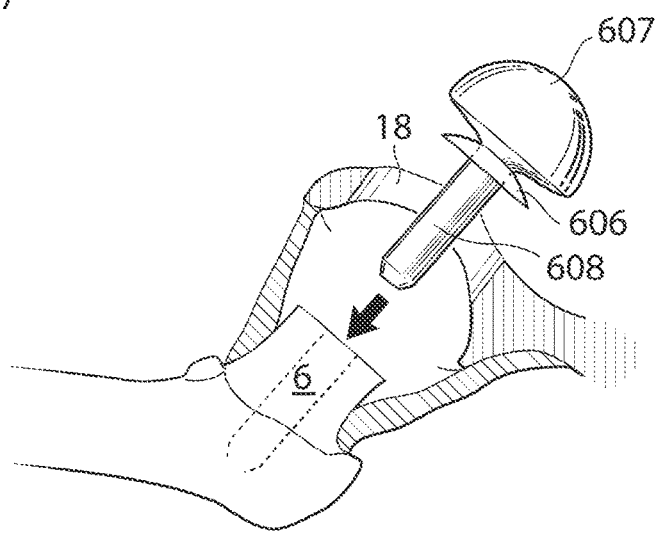
FIG. 63 shows the medical device with the piece of bone being inserted through a hole in the pelvic bone.

FIG. 63 shows a hip joint in section when the medical device 600, comprises an artificial caput femur surface 607, a fixating member 608 and a stabilizing member 606, being inserted through a hole 18 in the pelvic bone 9. According to this embodiment the stabilizing member is a piece of bone 606 placed on the outside of the fixating member 608. The stabilizing member 606 could be fixated to the fixating member 608 using adhesive or any mechanical connection, such as screws, cord, band or pop-rivets. According to this embodiment the medical device is stabilized by the cortical bone 601 of the collum femur 6 on the inside thereof substantially perpendicular to the longitudinal extension of the collum femur 6, and from the acetabulum side, substantially in line with the longitudinal extension of the collum femur 6 through the stabilizing member being placed in contact with the surface of a section 610 on the collum femur 6. The stabilizing member and the fixating member could be fixated to the collum femur 6 by means of an adhesive or bone cement.

Figure 64:
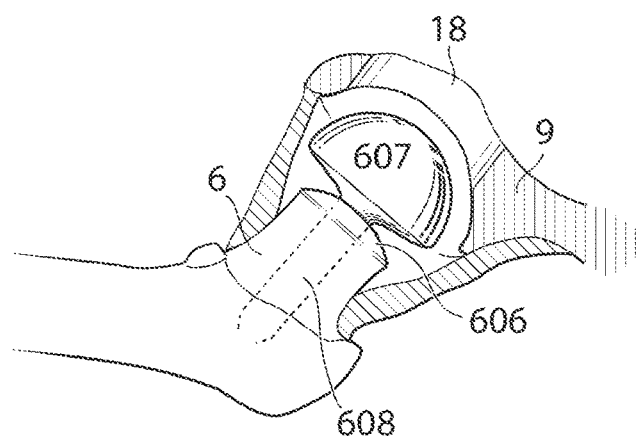
FIG. 64 shows the hip joint in section when the medical device has been provided.

FIG. 64 shows the hip joint in section when the medical device 600, according to the first embodiment, has been placed on the collum femur 6 and is stabilized from the inside thereof by the direct or indirect connection with the cortical bone 601 of the collum femur 6.

Figure 65:
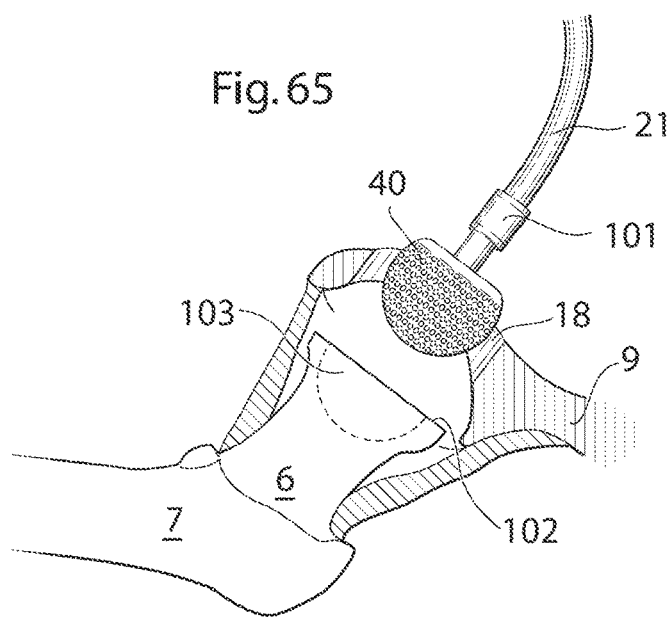
FIG. 65 shows the step of reaming the collum femur from a hole in the pelvic bone.

FIG. 65 shows the caput femur 5 after the proximal part has been removed along the section created by the medical device for creating a hole. The removing of the proximal part of the caput femur 5 creates a surface of a section 102 in the cortical bone of the caput femur 5. A reamer 40 adapted to create a concave surface 103 in the caput femur 5 is applied to the force transferring member 21 through a connecting section 101. According to this embodiment the force transferring member 21 is the same as the force transferring member used for the medical device adapted to create a hole in the pelvic bone 9, however it is equally conceivable that the force transferring member 21 is specifically designed to enable the reaming of the caput femur 5. The reaming in the caput femur and part of the collum femur 6 is mainly performed in the cancellous bone, however that does not exclude the possibility the some of the reaming needs to be performed in the cortical bone of the caput femur 5 and/or the collum femur 6.

Figure 66:
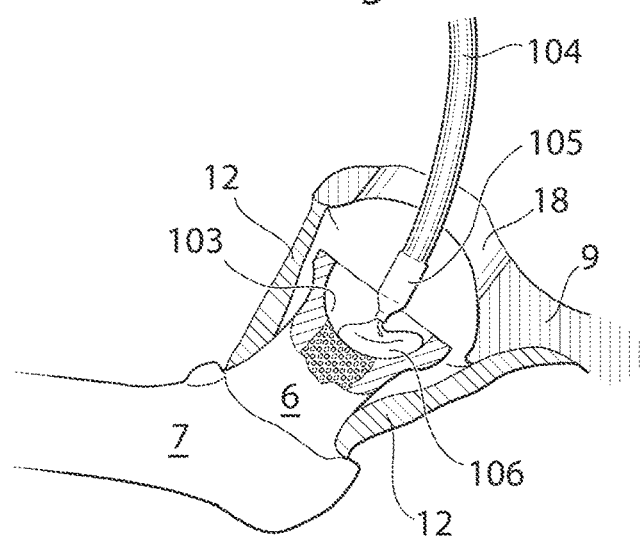
FIG. 66 shows the step of applying an adhesive to an area of the collum femur.

FIG. 66 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

Figure 67:
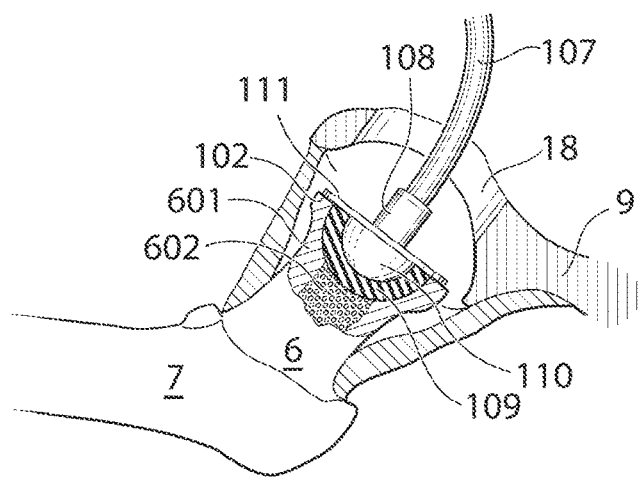
FIG. 67 shows the step of placing an artificial hip joint surface in the collum femur.

FIG. 67 shows the step of providing a medical device 109 comprising an artificial concave hip joint surface 110. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a inserting member 107. According to this embodiment the inserting member is bent and thereby adapted to operate through a hole 18 in the pelvic bone 9. The inserting member 107 comprises a connecting member 108 which is adapted to connect to the medical device 109. According to one embodiment the medical device 109 comprises a self lubricating material such as PTFE, however it is also conceivable that said medical device comprises: titanium, stainless steel, Corian, PE, or other acrylic polymers, in which case the medical device could be adapted to be lubricated after insertion in said hip joint.

Figure 68:
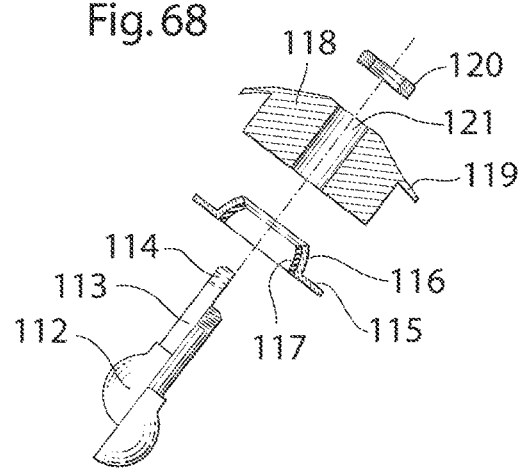
FIG. 68 shows the parts of a medical device according to another embodiment.

FIG. 68 shows a medical device comprising an artificial convex hip joint surface 112. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking element 116 comprising a surface 117 adapted to be in contact with the artificial convex hip joint surface 112. The locking element 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to a attachment rod 113 comprising a thread 114 that corresponds to the thread of the nut 120 in connection with the prosthetic part 118. According to the embodiment shown in FIG. 68 a part comprising the artificial convex hip joint surface 112, the attachment rod 113 and the thread 114 is formed by two parts wherein the first part 1241' comprises the first part of the artificial convex hip joint surface 112, the first part of the attachment rod 113 and the first part of the thread 114, and the second part 1241" comprises the second part of the artificial convex hip joint surface 112', the second part of the attachment rod 113 and the second part of the thread 114'. The first and second parts are adapted to the connected to each other to form a connected part for examples by means of the interconnecting functions as described with reference to FIGS. 23-30.

Figure 69:
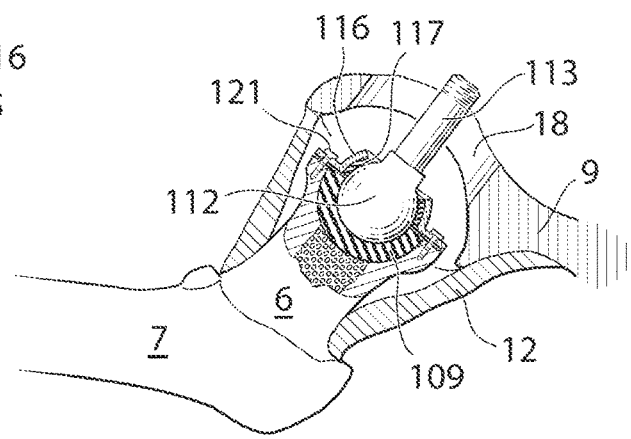
FIG. 69 shows the hip joint in section when a medical device has been provided.

FIG. 69 shows the hip joint in section when the artificial convex hip joint surface is fixated in the medical device 109 comprising a concave hip joint surface 110. The convex hip joint surface 112 is secured in place by the locking element 116 which is fixated to the caput femur using screws 121. The surface of the locking element 117 and the concave hip joint surface 117 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient.

Figure 70:
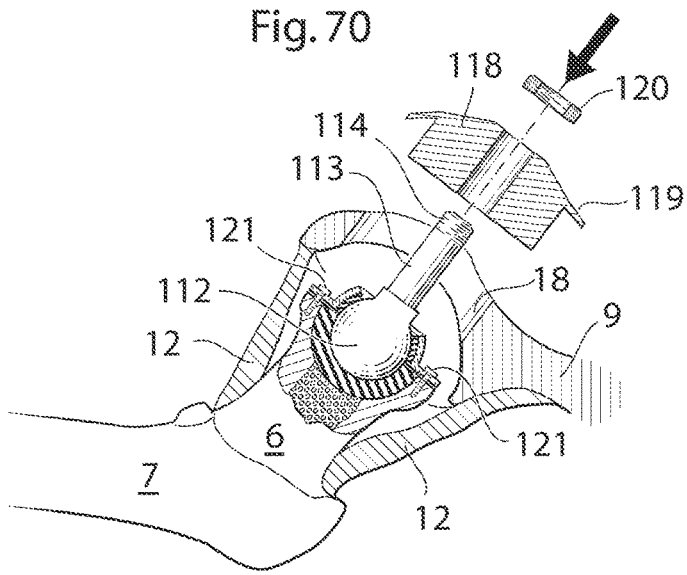
FIG. 70 shows the placing of a prosthetic part in the hole in the pelvic bone.

FIG. 70 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. According to the embodiment shown in FIG. 12 the supporting members 119 are located on the abdominal side of the pelvic bone 9, however it is equally conceivable the supporting members 119 are located on the acetabulum side of the pelvic bone 9, in which case they are preferably displaceable for allowing insertion of the prosthetic part 118 through the hole 18 in the pelvic bone 9. Furthermore FIG. 12 shows the fixation of a nut 120 to the attachment rod 113. According to the embodiment shown in FIG. 12 the hole 18 in the pelvic bone 9 is adapted to be larger than the medical device allowing the medical device to be inserted in its full functional size. According to other embodiments the hole 18 is smaller in which case the medical device could comprise of several parts adapted to be connected after insertion in the hip joint, such as shown in FIG. 68, or the medical device could be expandable for insertion through a hole smaller than the full functional size of the medical device. The expandable medical device could be enabled through the elements of the medical device comprising elastic material.

Figure 71:
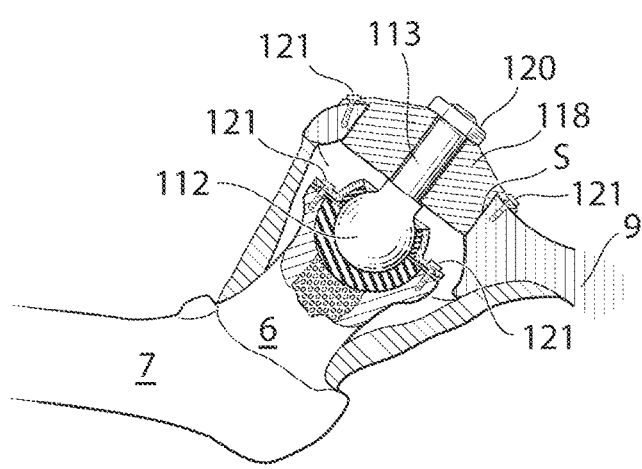
FIG. 71 shows a section of the hip joint when a medical device has been fixated.

FIG. 71 shows the hip joint in section when all the elements of the medical device has been fixated in the area of the hip joint or its surroundings. The prosthetic part 113 adapted to occupy the hole 18 in the pelvic bone 9 is here fixated with screws 121, however these screws 121 could be assisted or replaced by an adhesive which could be applied to the surface S between the prosthetic part and the pelvic bone 9.

In the above embodiments the medical device 600 have been described in the context of a surgical procedure from the abdominal side of the pelvic bone, however it is also conceivable that the medical device is inserted through the a hole in the femoral bone or a hole in the hip joint capsule, and is adapted therefore. A conceptual view of the embodiment where the medical device 600 is inserted through the hip joint capsule as shown with reference to FIGS. 2-10, what is commonly described as conventional hip joint surgery.

After the step of providing an artificial caput femur surface, the surgical and laparoscopic/arthroscopic methods could further comprise the step of providing an artificial acetabulum surface.

Figure 72:
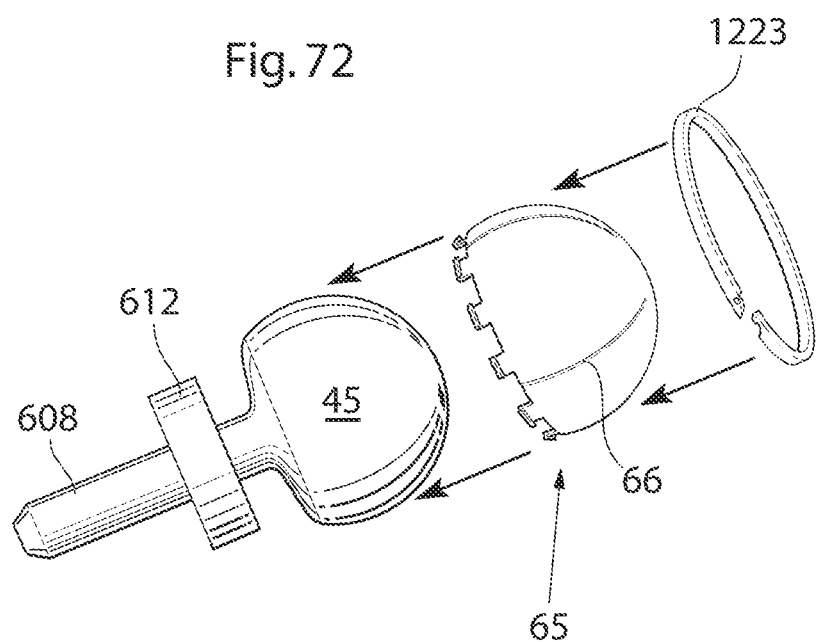
FIG. 72 shows a pre-mounted embodiment of the medical device.

FIG. 72 shows an embodiment where an artificial acetabulum surface 65 is pre-mounted onto the artificial caput femur surface 45. The medical device comprising the artificial caput femur surface 45 further comprises a fixating member 608 and a stabilizing member 612, adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member 612 being placed in contact with the surface of a section on the collum femur 6. According to the embodiment shown in FIG. 72 the artificial acetabulum surface 65 has a flexible construction with multiple slits 66 enabling the artificial acetabulum surface 65 to pass beyond the maximum diameter of the artificial caput femur surface 45 and thereby clasping the artificial caput femur surface 45. The artificial acetabulum surface is secured by a band, cord or wire 1223 placed encircling the artificial acetabulum surface 65.

Figure 73:
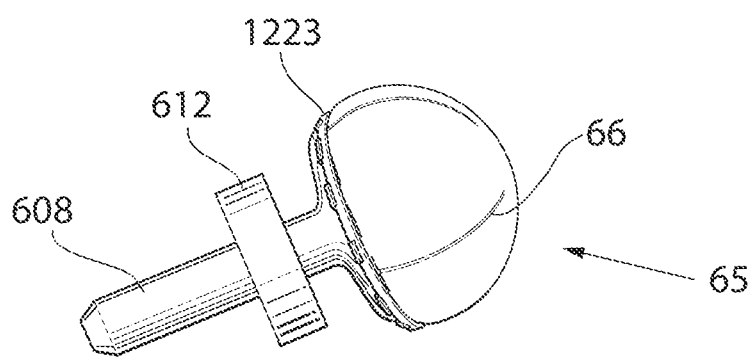
FIG. 73 shows a pre-mounted embodiment of the medical device, when assembled.

FIG. 73 shows the medical device when the pre-mounted artificial acetabulum surface 65 has been provided and secured by the band, cord or wire 1223 encircling the artificial acetabulum surface 65 beyond the maximum diameter of the artificial caput femur surface 45.

Figure 74:
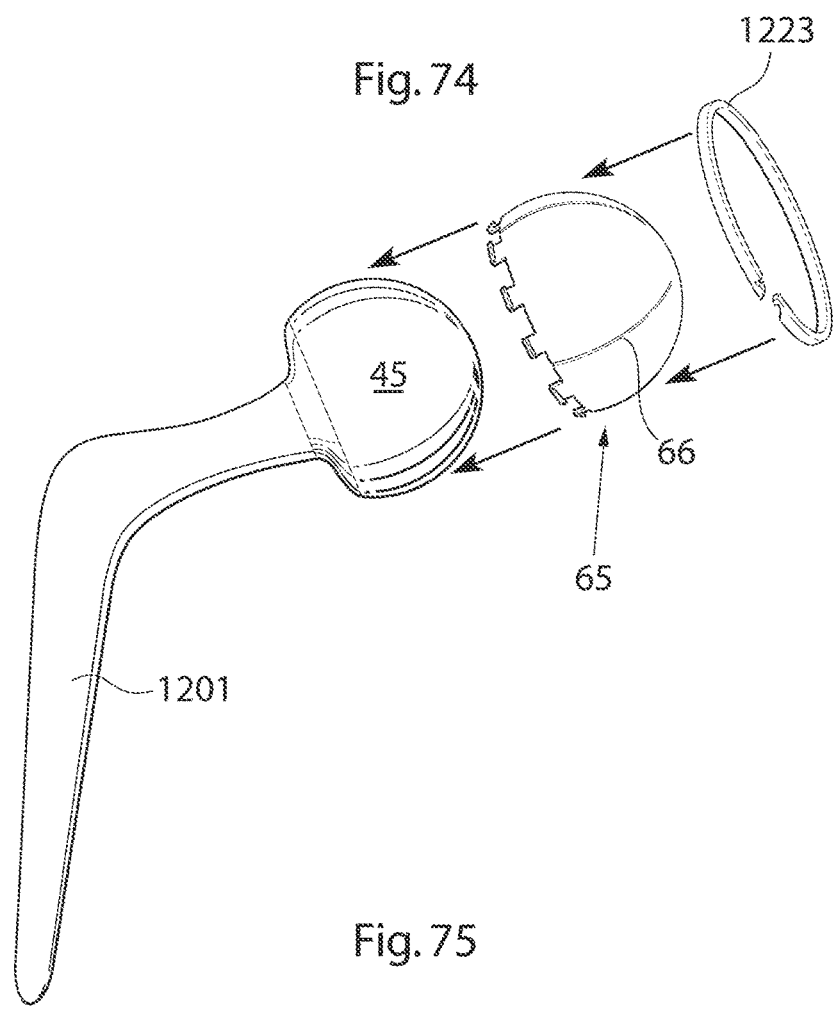
FIG. 74 shows a pre-mounted embodiment of the medical device.

FIG. 74 shows an embodiment where an artificial acetabulum surface 65 is pre-mounted onto the artificial caput femur surface 45. The medical device comprising the artificial caput femur surface 45 further comprises prosthetic stem for fixation of the medical device in the femoral bone. According to the embodiment shown in FIG. 74 the artificial acetabulum surface 65 has a flexible construction with multiple slits 66 enabling the artificial acetabulum surface 65 to pass beyond the maximum diameter of the artificial caput femur surface 45 and thereby clasping the artificial caput femur surface 45. The artificial acetabulum surface is secured by a band, cord or wire 1223 placed encircling the artificial acetabulum surface 65.

Figure 75:
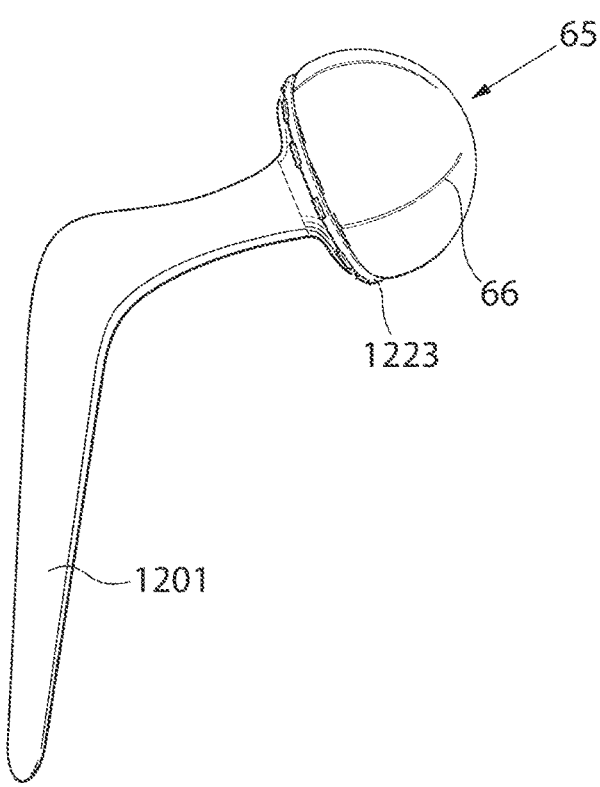
FIG. 75 shows a pre-mounted embodiment of the medical device, when assembled.

FIG. 75 shows the medical device when the pre-mounted artificial acetabulum surface 65 has been provided and secured by the band, cord or wire 1223 encircling the artificial acetabulum surface 65 beyond the maximum diameter of the artificial caput femur surface 45.

Figure 76:
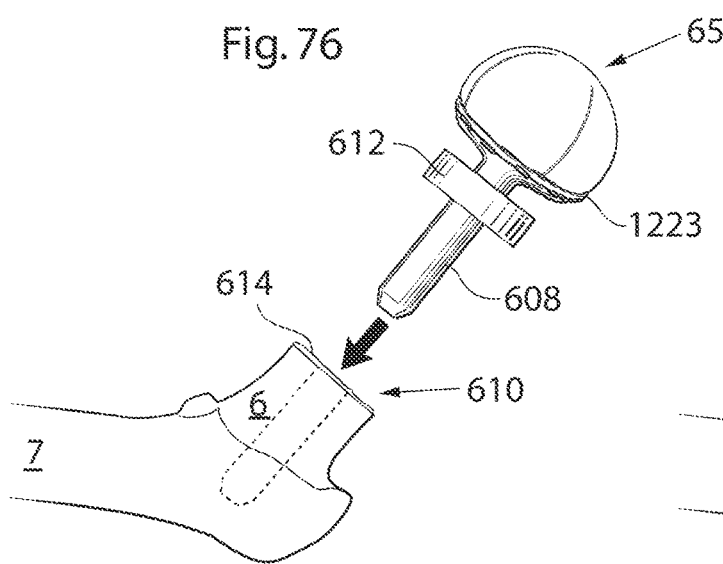
FIG. 76 shows a pre-mounted embodiment of the medical device, when being mounted in the collum femur.

FIG. 76 shows the femoral bone, in the step in which the surface of the section 610 in the collum femur 6 is prepared. An adhesive 614 is applied to the surface of the section 610 of the collum femur 6 for fixating the medical device, comprising a pre-mounted artificial acetabulum surface 65 on the artificial caput femur surface, to the collum femur 6 using the fixating member 608 and the stabilizing member 612.

Figure 77:
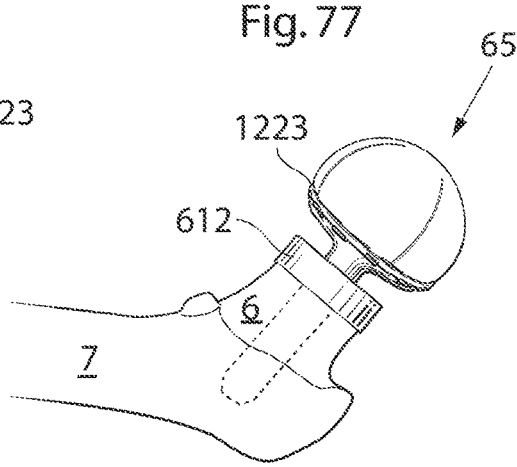
FIG. 77 shows a pre-mounted embodiment of the medical device, when mounted in the collum femur.

FIG. 77 shows the femoral bone after the step of introducing and fixating the medical device to the collum femur 6 has been preformed. The stabilizing member 612 is adapted to stabilize the medical device 600 from the outside of the collum femur 6 substantially perpendicular to the longitudinal extension of the collum femur 6, and from the acetabulum side, substantially in line with the longitudinal extension of the collum femur 6 through the stabilizing member being placed in contact with the outside of the collum femur 6 and the surface of the section 610 in the collum femur 6. The stabilizing member 612 is fixated to the outside of the collum femur 6 and/or to the surface of the section 610 in the collum femur 6 by means of the adhesive 614. However the adhesive 614 could be replaced or assisted by bone cement or a mechanical fixation element.

According to one embodiment the artificial acetabulum surface 65 is provided through a hole 18 in the pelvic bone 9 from the opposite side from acetabulum 8.

Figure 78:
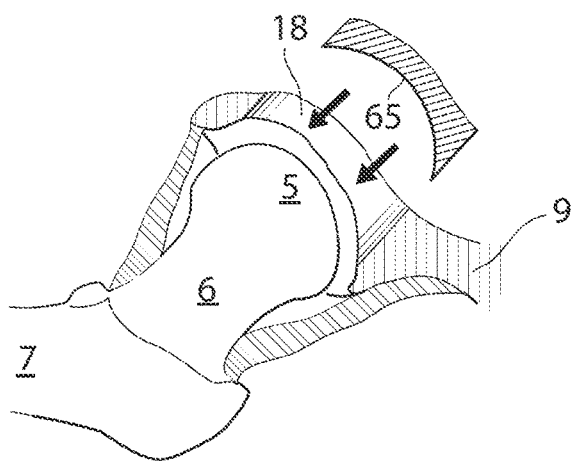
FIG. 78 shows an artificial acetabulum surface when being inserted into a hip joint.

FIG. 78 shows an artificial acetabulum surface 65 in its full functional size as it is being inserted through a hole 18 in the pelvic bone 9.

FIG. 79 shows an artificial acetabulum surface 65 according to a second embodiment in which the artificial acetabulum surface 65 comprises at least one slit 66 enabling the artificial acetabulum surface 65 to vary in size for insertion through a hole 18 in the pelvic bone 9 smaller than the full functional size of the artificial caput femur surface 45. The slits are placed between one or more artificial acetabulum surface arms 67 which are flexible by means of the material or by means of a joint affecting said artificial acetabulum surface arms 67.

FIG. 80a,b,c shows an artificial acetabulum surface 65 according to a second embodiment in which the artificial acetabulum surface 65 comprises multiple artificial acetabulum surface parts 68. Said multiple artificial acetabulum surface parts 68 are adapted to be connected to an interconnecting artificial acetabulum surface part 69 after insertion into a hip joint. The interconnecting artificial caput femur surface part 69 comprises self locking connecting members 70a, shown in FIG. 80b, that fits with corresponding self locking members 70b of the artificial acetabulum surface parts 68. The artificial acetabulum surface parts 68 create an artificial acetabulum surface 65 when connected to each other, shown in FIG. 80c. The self locking members 70a,b can be assisted or replaced with at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

FIG. 81a,b,c shows an artificial acetabulum surface 65 according to a third embodiment in which the artificial acetabulum surface 65 comprises multiple ring-shaped artificial acetabulum surface parts 71. Said multiple ring-shaped artificial acetabulum surface parts 71 are adapted to be connected to each other to form an artificial acetabulum surface 65 after insertion in a hip joint. According to one embodiment said artificial acetabulum surface parts 71 are adapted to be connected to each other using mechanical connecting members 72a,b. FIG. 81c shows how an individual ring-shaped artificial acetabulum surface part 71 can be connected to itself using the mechanical connecting member 72a to form a continuous ring shape. Further 81c shows how an individual ring-shaped artificial acetabulum surface part 71 connects to other ring-shaped artificial acetabulum surface parts 71 using the mechanical connecting member 72b to form an artificial acetabulum surface 65.

Figure 82A:
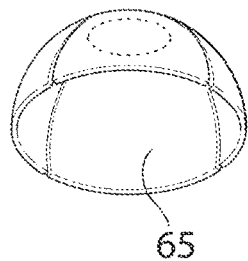
FIG. 82a shows an artificial acetabulum surface according to a fourth embodiment.
Figure 82B:
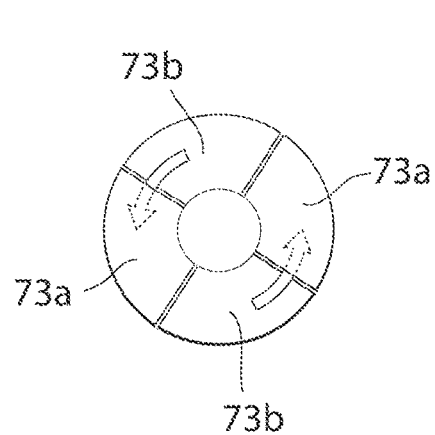
FIG. 82b shows the function of the artificial acetabulum surface according to the fourth embodiment.
Figure 82C:
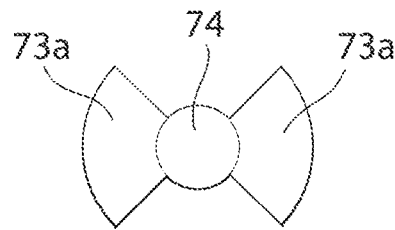
FIG. 82c shows an artificial acetabulum surface according to a fourth embodiment in its folded state.
Figure 82D:
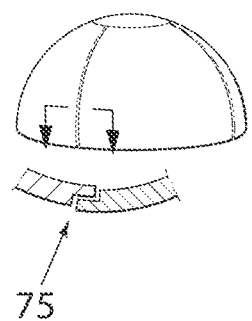
FIG. 82d shows the connection function of the artificial acetabulum surface according to a fourth embodiment.

FIG. 82a,b,c,d shows an artificial acetabulum surface 65 according to a fourth embodiment in which the artificial acetabulum surface 65 comprises a first 73a and a second 73b section, shown in FIG. 82b. The first and second sections are displaceable in relation to each other. According to a first embodiment said first section 73a can be rotated in relation to said second section 73b so that said second section 73b travels underneath said first section 73a to create a displaced artificial acetabulum surface 74, as shown in FIG. 38c, which is possible to insert into a hip joint of a human patient through a hole being oval, or at least having an area smaller than the cross sectional area of the artificial acetabulum surface 65 when in its full functional size 65. According to this embodiment the two sections 73a,b are connected to each other when the artificial acetabulum surface is returned to its full functional size using a mechanical form fitting 75, as shown in FIG. 82d. However it is also conceivable that said connection is assisted or replaced with at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 83A:
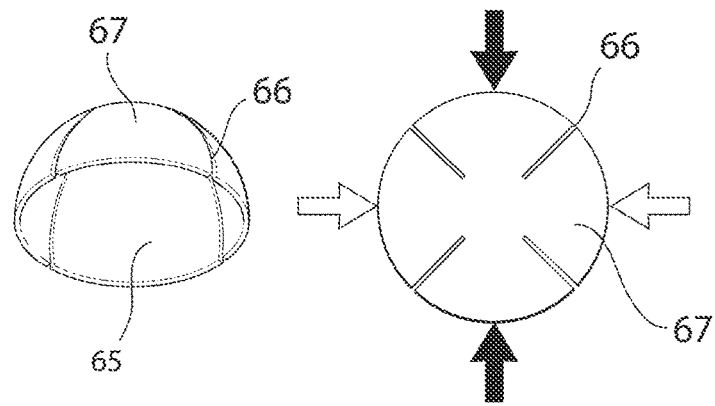
FIG. 83a shows an artificial acetabulum surface according to a fifth embodiment.

FIG. 83a shows an artificial acetabulum surface 65 according to a fifth embodiment in which the artificial acetabulum surface 65 comprises four slits 66. The artificial acetabulum surface 65 is flexible in its construction allowing the four artificial acetabulum arms 67 to be folded towards the center axis of the artificial acetabulum surface 65 thus allowing the artificial acetabulum surface to be inserted into a hip joint through a hole smaller than the full functional size of the artificial acetabulum surface 65.

Figure 83B:
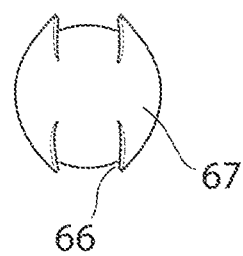
FIG. 83b shows an artificial acetabulum surface according to the fifth embodiment in its folded state.

FIG. 83b shows the artificial acetabulum surface 65 according to the fifth embodiment in its folded state. The artificial acetabulum surfaces 65 of any of the embodiments could be adapted to pass beyond the maximum diameter of the caput femur 5 and thereby fixate the artificial acetabulum surface 65 to the caput femur, or an artificial replacement therefore, by clasping the caput femur 5.

Figure 84A:
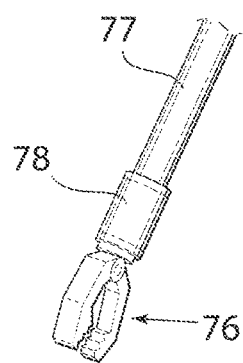
FIG. 84a shows an instrument for inserting parts into a hip joint according to a first embodiment.

FIG. 84a shows a surgical instrument adapted to insert a prosthesis, prosthetic parts or parts needed to create or provide a hip joint surface, according to a first embodiment. The surgical instrument comprises a gripping portion 76 and a handling portion 77. According to the embodiments shown in FIG. 84a,b,c the instrument further comprises a rotation element 78 that enables the gripping part 76 to rotate in relation to the handling part 77, however it is equally conceivable that the surgical instrument lacks this rotation element 78.

Figure 84B:
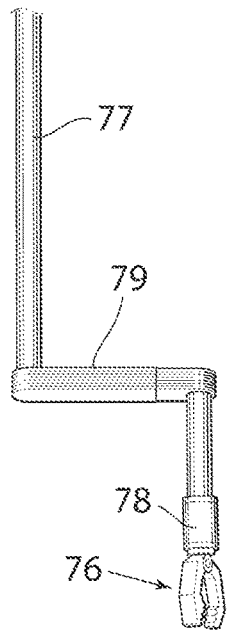
FIG. 84b shows an instrument for inserting parts into a hip joint according to a second embodiment.

FIG. 84b shows the surgical instrument adapted to insert a prosthesis, prosthetic parts or parts needed to create or provide a hip joint surface, according to a second embodiment. According to this embodiment the surgical instrument further comprises a parallel displaced section 79, which increases the reach of the instrument and facilitates the reaching of the hip joint through a hole in the pelvic bone from the opposite side from acetabulum.

Figure 84C:
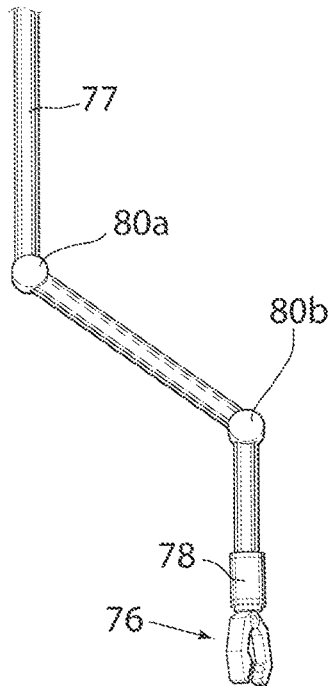
FIG. 84c shows an instrument for inserting parts into a hip joint according to a third embodiment.

FIG. 84c shows the surgical instrument adapted to insert a prosthesis, prosthetic parts or parts needed to create or provide a hip joint surface, according to a third embodiment. According to this embodiment the surgical instrument further comprises two angle adjusting members 84a,b. The angle adjusting members could be adjustable for varying the angle of said gripping part 76 in relation to the handling portion 77, or fixed in an angle suitable for creating operating in a hip joint through a hole in the pelvic bone from the opposite side from acetabulum 8.

Figure 85:
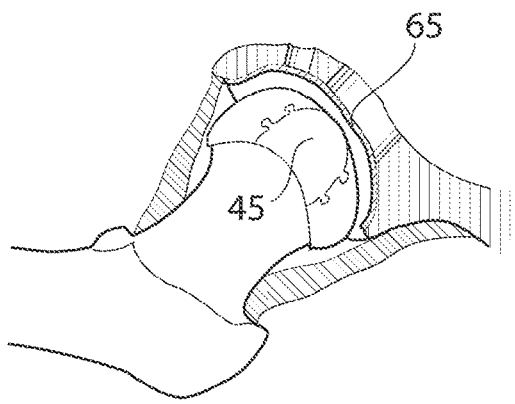
FIG. 85 shows a hip joint in section after an artificial caput femur surface and an artificial acetabulum surface have been provided.

FIG. 85 shows the hip joint in section after the artificial caput femur surface 45, and the artificial acetabulum surface 65 have been provided through a hole in the pelvic bone.

Figure 86:
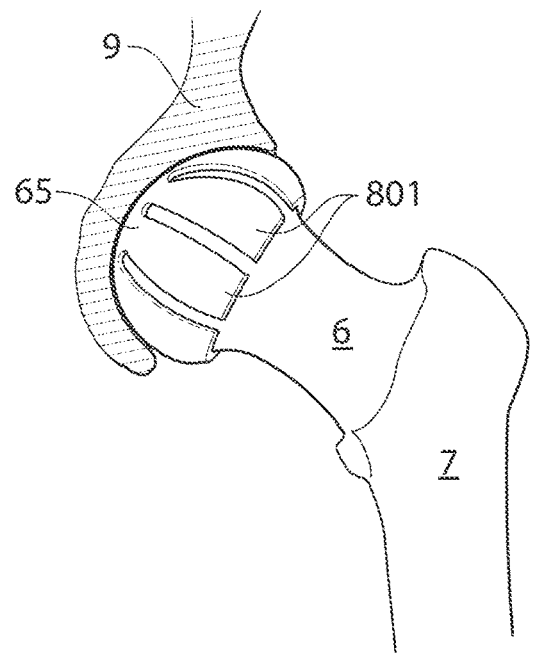
FIG. 86 shows the hip joint in section when a medical device has been provided, in a first state.

FIG. 86 shows an artificial bowl shaped acetabulum cup 65 placed in the pelvic bone 9. The artificial bowl shaped acetabulum cup 65 comprises releasing members 801 adapted, in a first state, to hold the caput femur 5 which is a ball shaped piece attached to the collum femur 6 in position in the hip joint to the artificial bowl shaped acetabulum cup 65 placed in the pelvic bone 9. In a second state the releasing member 801 is adapted to release the caput femur 5, or an artificial replacement therefore, from the artificial bowl shaped acetabulum cup 65 placed in the pelvic bone 9. The releasing member 801 is adapted to change from the first state to the second state when a pre-determined strain is placed on the releasing member 801. The strain is preferably caused by an abnormal movement of the hip joint, e.g. as the result of the patient falling. According to the embodiment shown in FIG. 9 the releasing member 801 comprises an elastic portion comprising elastic material, in the embodiment shown being the entire releasing member 801. The releasing member is adapted to non-invasively be able to change from the first state to the second state and from the second state to the first state, when a pre-determined strain is placed on the releasing member 801.

Figure 87:
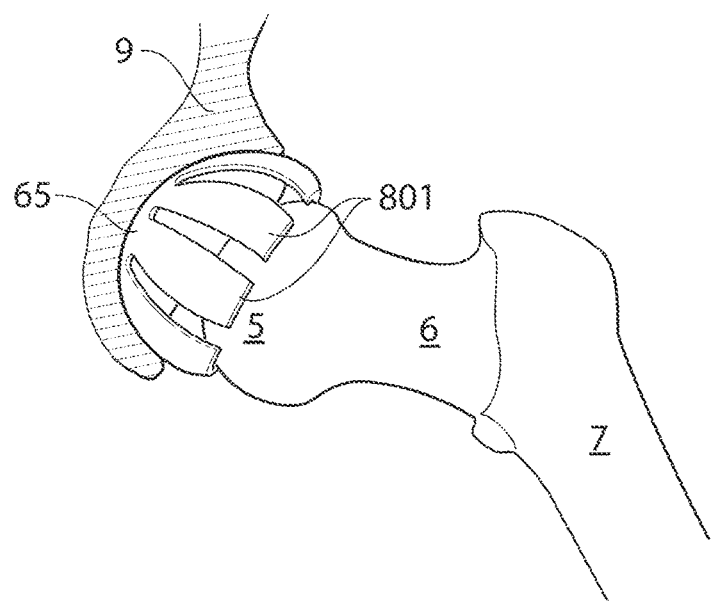
FIG. 87 shows the hip joint in section when a medical device has been provided, in a second state.

FIG. 87 shows the hip joint in section when the releasing member 801 is in its second state, wherein the releasing member 801 is adapted to release the caput femur 5, or an artificial replacement therefore, from the artificial bowl shaped acetabulum cup 65 placed in the pelvic bone 9. The releasing member 801 has changed from the first state to the second state because of a pre-determined strain has been placed on the releasing members 801.

Figure 88:
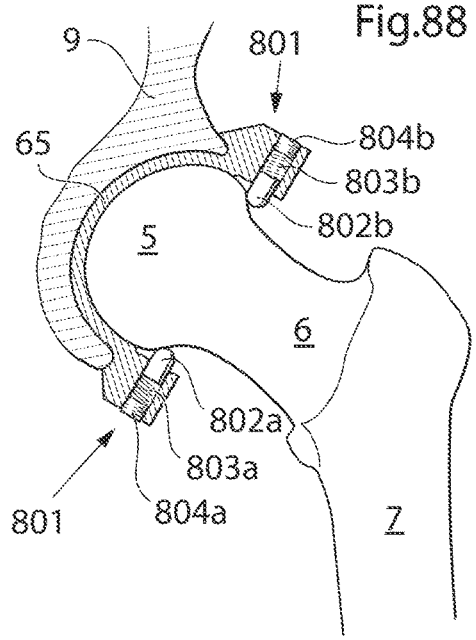
FIG. 88 shows the hip joint in section when a medical device has been provided, in a first state.

FIG. 88 shows the medical device according to an embodiment where the artificial bowl shaped acetabulum surface 65 comprises releasing members 801 comprising holding members 802a,b adapted to slide against the caput femur 5, or an artificial replacement therefore. The holding members are adapted to, in a first state, hold the caput femur 5, or an artificial replacement therefore, which is a ball shaped part attached to the collum femur 6 in position in the hip joint to the artificial bowl shaped acetabulum cup 65 placed in the pelvic bone 9. In a second state the releasing member 801 is adapted to release the caput femur 5, or an artificial replacement therefore, from the artificial bowl shaped acetabulum cup 65 placed in the pelvic bone 9. The holding members 802a,b are spring loaded through a spring 803a,b being placed between a calibration member, being a calibration screw 804a,b, and the holding members 802a,b. The force exerted on the holding members 802a,b from the spring 803a,b is adapted to hold the caput femur 5, or an artificial replacement therefore, in the artificial acetabulum 65 in normal, functional hip joint movements, but release the caput femur 5, or an artificial replacement therefore, from the artificial acetabulum 65 when a pre-determined strain is placed on the releasing member preferably being caused by an abnormal movement of the hip joint, e.g. as the result of the patient falling. The calibration screws 804a,b enables the pre-determination of the strain which will cause the holding members 802a,b to change from being in a first state to being in a second state.

Figure 89:
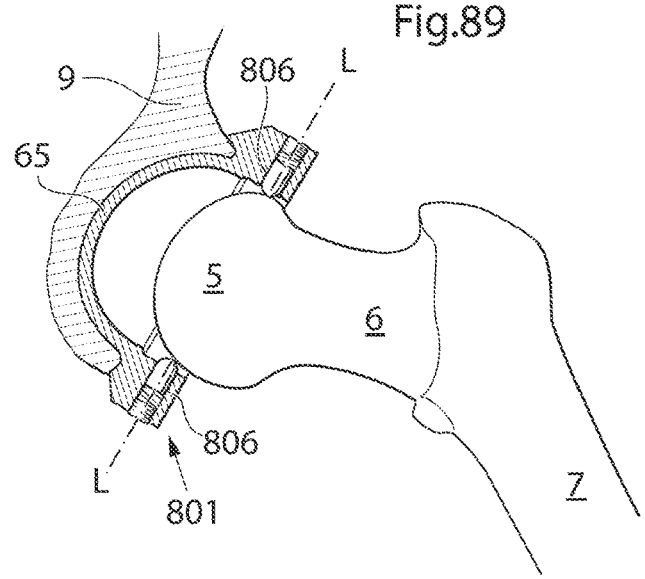
FIG. 89 shows the hip joint in section when a medical device has been provided, in a second state.

FIG. 89 shows the releasing members in their second state, when a pre-determined strain has been exceeded, preferably being caused by an abnormal movement of the hip joint, e.g. as the result of the patient falling. The holding members 802a,b are retracted into sleeves 806 of the artificial acetabulum surface 65, thereby compressing the springs 803a,b. The retraction of the holding members 802a,b causes the caput femur 5, or an artificial replacement therefore, to be dislocated/luxated from its position in the artificial acetabulum surface 65, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b.

Figure 90:
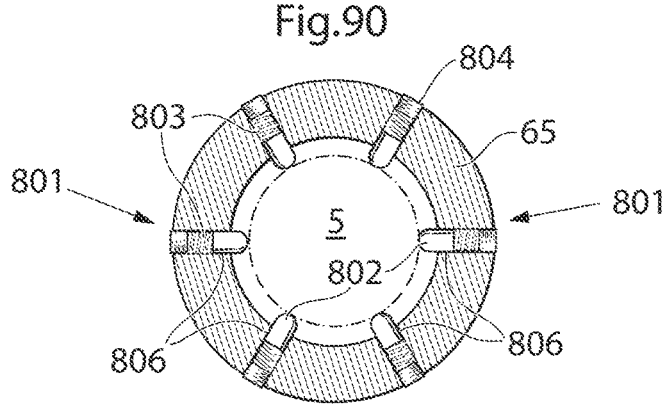
FIG. 90 shows the medical device in section.

FIG. 90 shows the artificial acetabulum 65 in section with the holding members 802, placed in sleeves 806 evenly distributed along the cross-section of the artificial acetabulum 65, holding the caput femur 5, or an artificial replacement therefore, in position in the artificial acetabulum 65.

Figure 91:
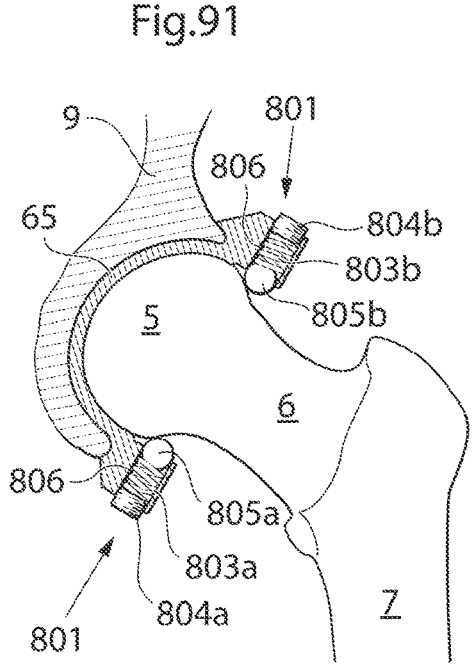
FIG. 91 shows an alternative embodiment of the medical device shown in FIG. 88, in a first state.

FIG. 91 shows an alternative embodiment of the principle shown in FIGS. 88-90, wherein the holding members 802a, b, comprises ball shaped members 805a,b in contact with the caput femur 5, or an artificial replacement therefore, ant being adapted to roll against the caput femur 5, or an artificial replacement therefore, holding the caput femur 5, or an artificial replacement therefore, in place in the artificial acetabulum 65 by the holding members 802a,b exerting force on the caput femur 5, or an artificial replacement therefore, through the contact with the springs 803a,b supported by the calibration screws 804a,b.

Figure 92:
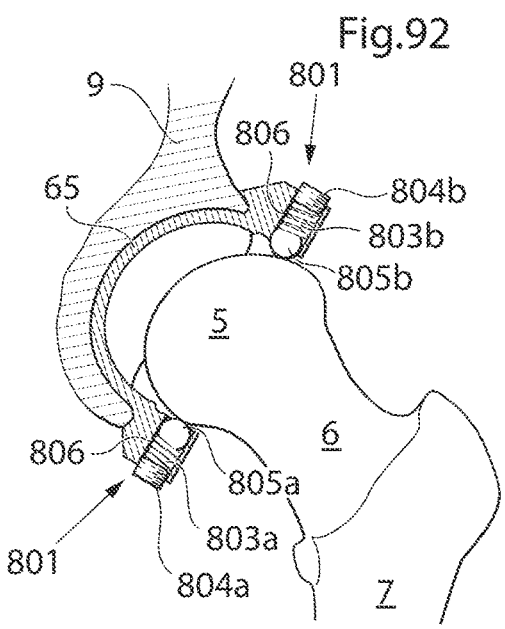
FIG. 92 shows an alternative embodiment of the medical device shown in FIG. 88, in a second state.

FIG. 92 shows the releasing members in their second state, when a pre-determined strain has been exceeded, preferably being caused by an abnormal movement of the hip joint, e.g. as the result of the patient falling. The holding members 802a,b, comprising the ball shaped members 805a, b, are retracted into sleeves 806 of the artificial acetabulum surface 65, thereby compressing the springs 803a,b. The retraction of the holding members 802a,b causes the caput femur 5, or an artificial replacement therefore, to be dislocated/luxated from its position in the artificial acetabulum surface 65, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b, which enables the caput femur 5, or an artificial replacement therefore, to be replaced in the artificial acetabulum 65 without a surgical procedure.

Figure 93:
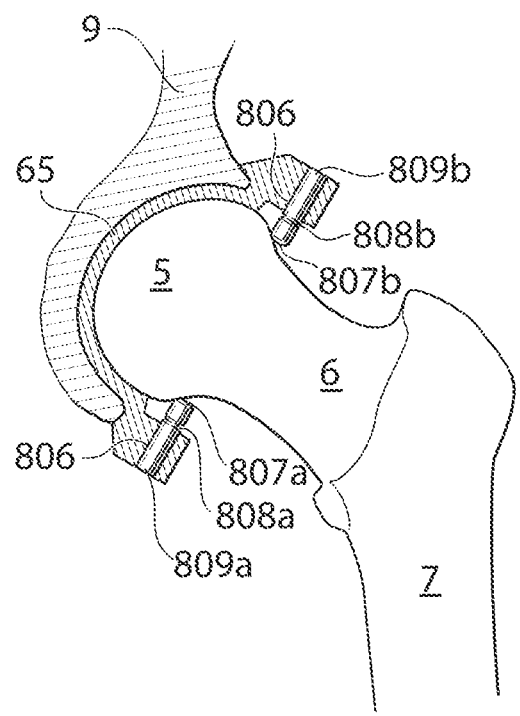
FIG. 93 shows the hip joint in section, when a medical device according to yet another embodiment is provided, in a first state.

FIG. 93 shows the medical device in an embodiment wherein the releasing members 801 comprises a rupture device 807, 808, 809 adapted to fail at a pre-determined strain. According to this embodiment the rupture device is a rupture pin 807, 808, 809 comprising a base part 809a,b fixated to the artificial acetabulum 65 and a rupture part 807a,b attached to the base part 809a,b through a weakened section 808a,b, in which section the rupture part 807a,b is detached from the base part 809a,b when a predetermined strain is placed on the rupture device in contact with the caput femur 5, or an artificial replacement therefore.

Figure 94:
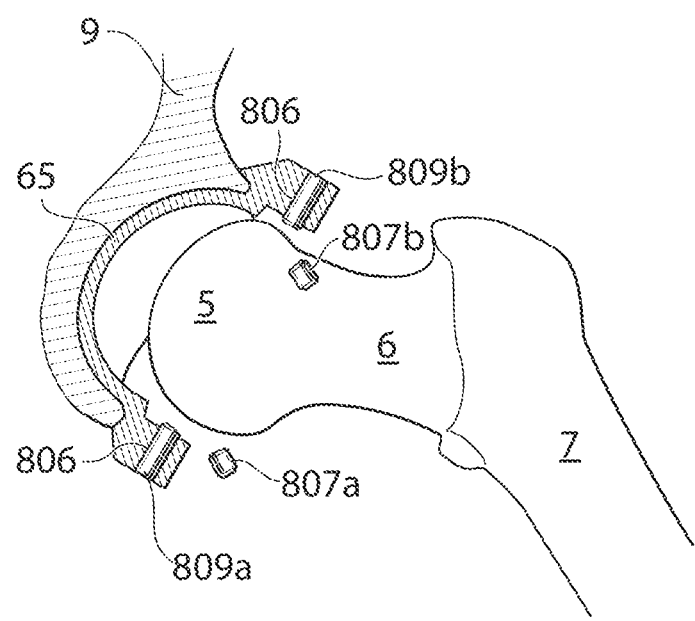
FIG. 94 shows the hip joint in section, when a medical device according to yet another embodiment is provided, in a second state.

FIG. 94 shows the medical device according to the embodiment of FIG. 93 when the rupture device has failed due to a pre-determined strain on the rupture device being exceeded. According to one embodiment, (not shown) the rupture parts 807a,b are secured to the base part through a security wire keeping rupture parts 807a,b in proximity to the base part 809a,b even after the failure of the rupture device.

Figure 95A:
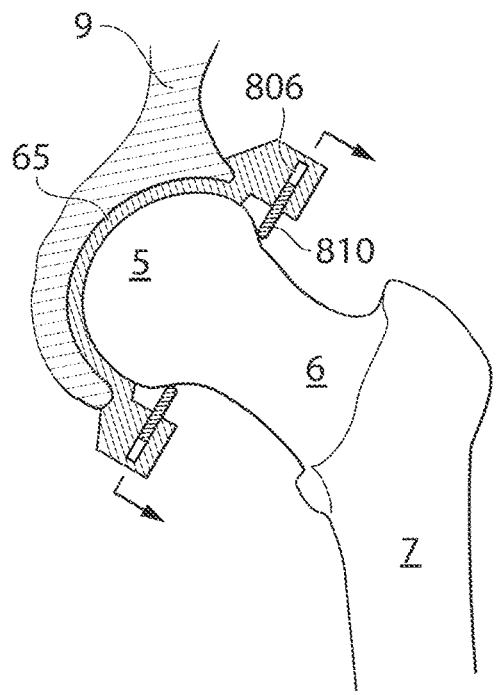
FIG. 95a shows the hip joint in section when a medical device comprising an elastic or rupture band has been provided, in a first state.

FIG. 95a shows the medical device according to an embodiment where the artificial acetabulum 65 comprises a circular sleeve 806, in which an elastic or rupture band 810 is provided. The elastic or rupture band 810 is adapted to at least partly encircle the ball shaped caput femur 5, or artificial replacement therefore. When a pre-determined strain is placed on the elastic or rupture band 810 the circular opening encircling the caput femur 5, or an artificial replacement therefore, is expanded and the caput femur 5, or an artificial replacement therefore, is released from the artificial acetabulum 65, to which it is held by means of the elastic band 610. In embodiments where the medical device comprises a rupture band 810 holding the caput femur 5, or an artificial replacement therefore, in the artificial acetabulum 65, a weakened portion 811 of the band 810 fails and thus the circular opening encircling the caput femur 5, or an artificial replacement therefore, is expanded and the caput femur 5, or an artificial replacement therefore, is released from the artificial acetabulum 65. In the embodiments where the band 810 is an elastic band 810 it is conceivable that the band 810 comprises an elastic part or section, or that the entire band 810 is made of an elastic material.

Figure 95B:
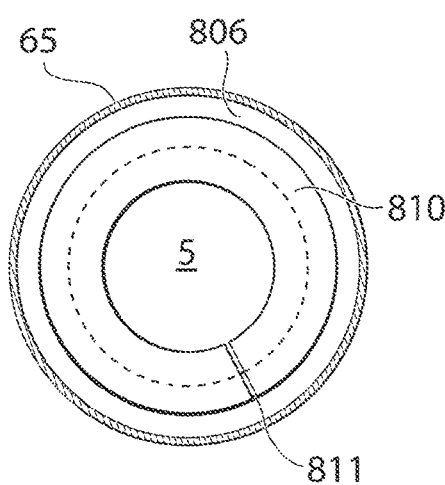
FIG. 95b shows the medical device of FIG. 95a, in section, in a first state.

FIG. 95 b shows the medical device in section when the elastic or rupturing band 810, holding the caput femur 5, or an artificial replacement therefore, is placed in a circular sleeve 806 in the artificial acetabulum 65. An opening or weakened portion 811 is provided perpendicular to the circumference of the band 810.

Figure 96A:
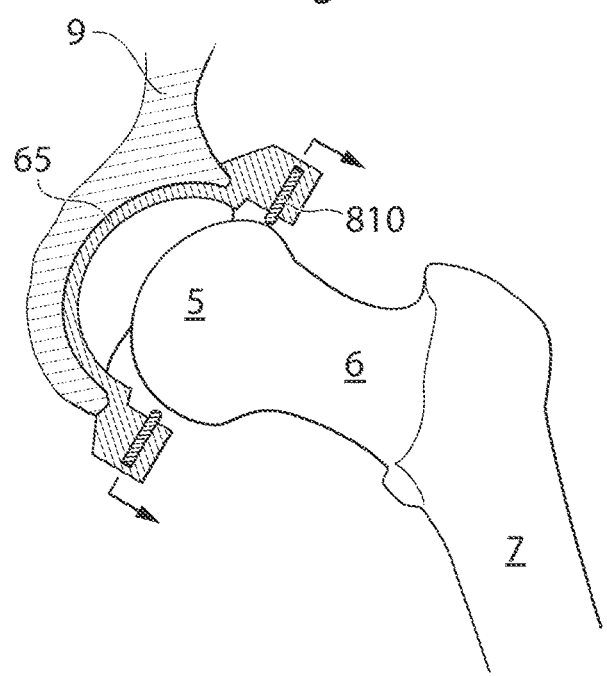
FIG. 96a shows the hip joint in section when a medical device comprising an elastic or rupture band is provided, in a second state.
Figure 96B:
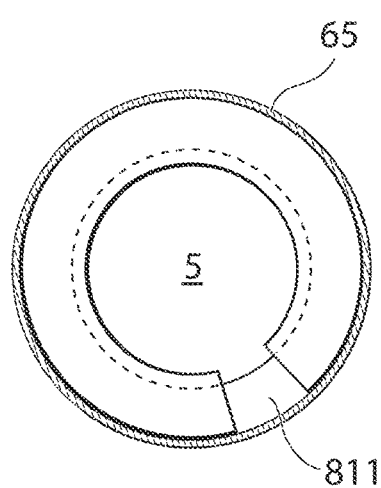
FIG. 96b shows the medical device of FIG. 19a, in section, in a second state.

FIG. 96a shows the medical device in a second state where the caput femur 5, or an artificial replacement therefore, is released from the connection with the acetabulum, after a pre-determined stain has been placed on the elastic or rupture band 810. As shown in FIG. 96b the gap or weakened part has been expanded, thereby allowing the caput femur, or an artificial replacement therefore, 5 to pass through the opening defined by the elastic or rupture band 810. The medical device could be adapted to non-invasively be able to change from the first state to the second state and from the second state to the first state, when a pre-determined strain is placed on the band 810, which enables the caput femur 5, or an artificial replacement therefore, to be replaced in the artificial acetabulum 65 without a surgical procedure.

Figure 97:
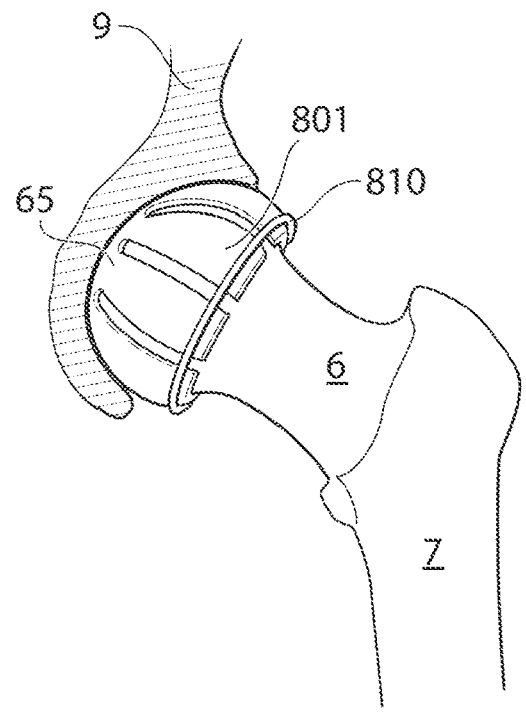
FIG. 97 shows the hip joint in section, when a medical device according to yet another embodiment has been provided, in a first state.

FIG. 97 shows the medical device according to an embodiment where the releasing member 801 comprises an elastic wing of the artificial acetabulum 65, which is assisted by an elastic or rupture band 810 encircling the medical device by enclosing the caput femur 5, or an artificial replacement therefore, in the artificial acetabulum 65 passing beyond the point of the caput femur 5, or an artificial replacement therefore, having a largest. The elastic or rupture band 810 is held in place to the artificial acetabulum 65 by means of the band 810 being placed in a groove along the circumference of the artificial acetabulum 65. However, said groove could be assisted or replaced by an adhesive or a mechanical fixation element.

Figure 98:
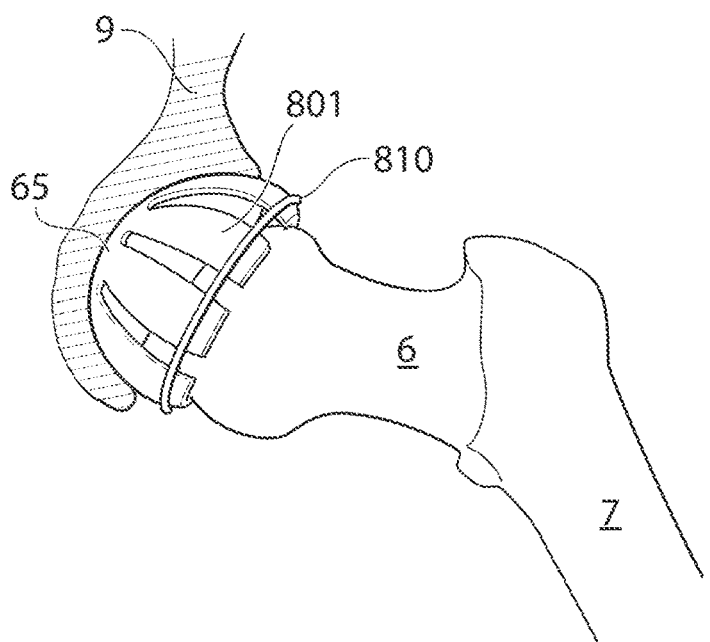
FIG. 98 shows the hip joint in section, when a medical device according to yet another embodiment has been provided, in a second state.

FIG. 98 shows the medical device when in its second state, in which the releasing member 801 releases the caput femur 5, or an artificial replacement therefore, from the artificial acetabulum 65. In embodiments when the band 810 is an elastic band 810 it is expanded, thereby enlarging the hole through which the caput femur 5, or an artificial replacement therefore, can pass. In embodiment where the band 810 is a rupture band, the band 810 has failed and thereby the caput femur 5, or an artificial replacement therefore, is held in place solely by the releasing member 801 which is adapted to release the caput femur 5, or an artificial replacement therefore, at a pre-defined strain. The medical device could be adapted to non-invasively be able to change from the first state to the second state and from the second state to the first state, when a pre-determined strain is placed on the band 810 and/or the releasing member 801, which enables the caput femur 5, or an artificial replacement therefore, to be replaced in the artificial acetabulum 65 without a surgical procedure.

Figure 99:
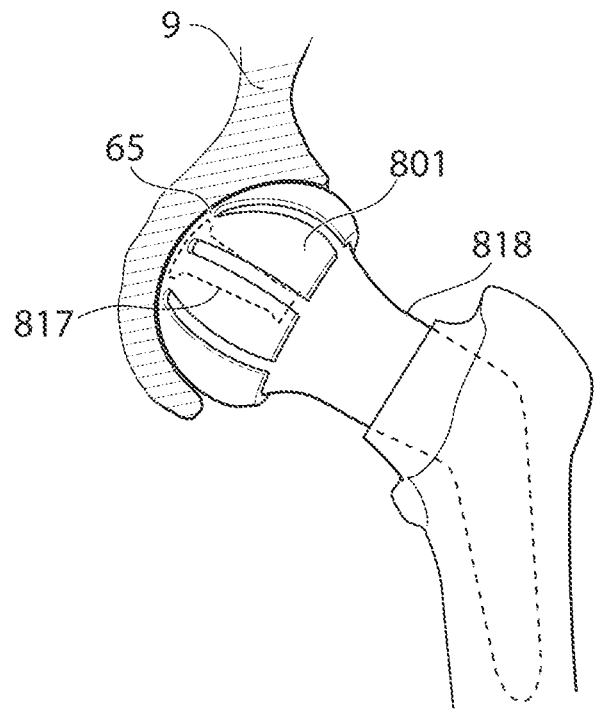
FIG. 99 shows the hip joint in section, when a medical device according to yet another embodiment has been provided, in a first state.

FIG. 99 shows a prosthetic part 818 according to an embodiment where the prosthetic part 818 is fixated to the femoral bone 7 and comprises a caput femur 812 comprising a cavity 816 adapted to enable the hip joint to perform functional hip joint movements while in a first state held to the artificial acetabulum using an elastic bend 817 fixated to a fixation portion 814 of the artificial caput femur 812, and a fixating portion 815 of the artificial acetabulum 65, and a releasing member 801 according to the embodiment shown in FIGS. 9 and 10. The combination of the releasing member 801 and the elastic band 817 is adapted to, in a first state hold the prosthetic part 818 to the artificial acetabulum 65, and in a second state release the prosthetic part 818 from the artificial acetabulum 65. According to another embodiment (not shown) the prosthetic part is held to the artificial acetabulum 65 solely using the elastic band 817, of course also supported by the remainder of the hip joint capsule and the affected muscles.

Figure 100:
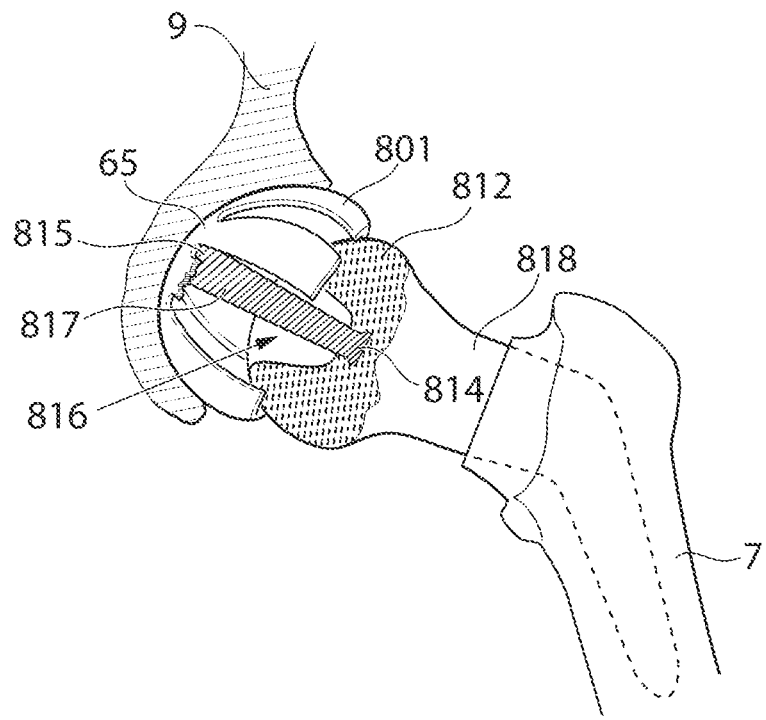
FIG. 100 shows the hip joint in section, when a medical device according to yet another embodiment has been provided, in a second state.

FIG. 100 shows the embodiment of the medical device according to FIG. 99, in a second state in which the elastic band 817 is stretched such that the prosthetic part 818 is released from the artificial acetabulum artificial acetabulum 65. The elastic band 817 could be fixated to a fixation portion 814 of the artificial caput femur 812, and/or a fixating portion 815 of the artificial acetabulum 65 using: at least one screw, at least one pin, form fitting, welding, adhesive, pin, wire, a ball mounted into a bowl, a male portion of one part mounted into a female portion of the other part, a key introduced into a lock being portions of said parts, band, or other mechanical connecting members. The failing of the rupture band 813 is preferably caused by an abnormal movement of the hip joint, e.g. as the result of the patient falling. Preferably the elastic band 817 comprises an elastic part or section, which could be the entire elastic band 818, made from an elastic material, such as an elastic polymer material such as: a copolymer material such as polystyrene, poly(ethylene-butylene) or polystyrene. It is also conceivable that the material is a polyurethane elastomeric material, polyamide elastomeric materials and polyester elastomeric materials elastic copolymers of ethylene and at least one vinyl monomer such as, for example, vinyl acetates, unsaturated aliphatic monocarboxylic acids, and esters of such monocarboxylic acids. The elastic band 813 could comprise a barrier coating, which cannot be penetrated by body cells. Preferably, the barrier coating comprises a Parylene coating, or a biocompatible metal coating, such as gold, silver or titanium. According to other embodiments the elastic band comprises a spring type member, a combination of metal and plastic materials, a combination of metal and carbon based material or a combination of carbon and plastic based material.

Figure 101:
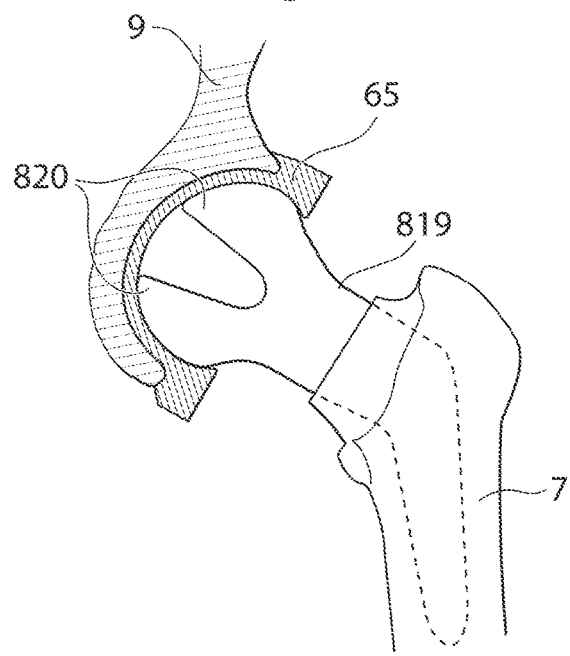
FIG. 101 shows the hip joint in section when a medical device, according to an embodiment where the artificial acetabulum surface comprises elastic elements, has been provided, in a first state.

FIG. 101 shows the hip joint in section in an embodiment where the medical device comprises a prosthetic part 819 adapted to be fixated to the femoral bone 7. The prosthetic part comprises an artificial caput femur which is adapted to comprise elastic elements 820 which act as a releasing member holding the artificial caput femur inside of the artificial acetabulum 65 fixated to the pelvic bone. The elastic elements 820 of the artificial caput femur, is preferably made of an elastic material, which for example could be an elastomeric polymer material or an elastic metal material. It is conceivable that the elastic material comprises an outer layer in connection with the artificial acetabulum 65 which is adapted to resist the wear from the contact with the artificial acetabulum surface, which could be a ceramic material. The elastic element is adapted to compress when a pre-determined strain is placed on the hip joint and thereby on the elastic elements 820. When the elastic elements 820 are compressed the artificial caput femur is released from the artificial acetabulum 65.

Figure 102:
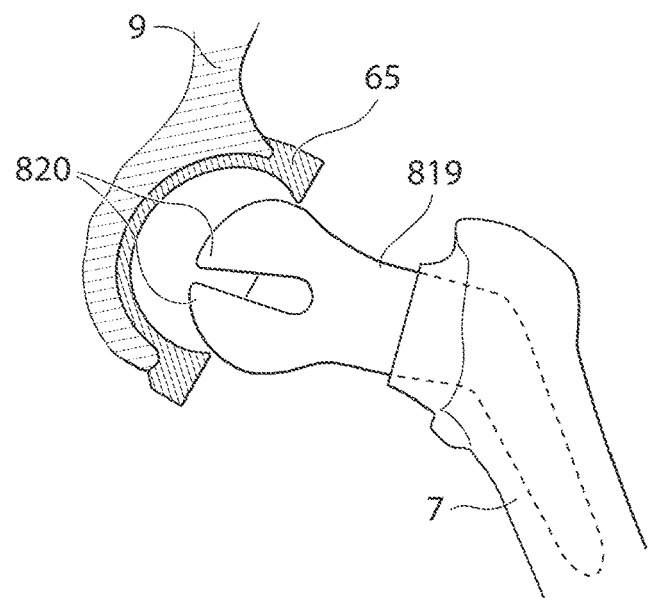
FIG. 102 shows the hip joint in section when a medical device, according to an embodiment where the artificial acetabulum surface comprises elastic elements, has been provided, in a second state.

FIG. 102 shows the medical device according to the embodiment shown in FIG. 101, in a second state, in which the elastic element 820 has been compressed, following a pre-determined strain being placed on the medical device. The medical device is thereby placed in a second state, in which the artificial caput femur is released from the artificial acetabulum 65, wherein it has been held.

Figure 103:
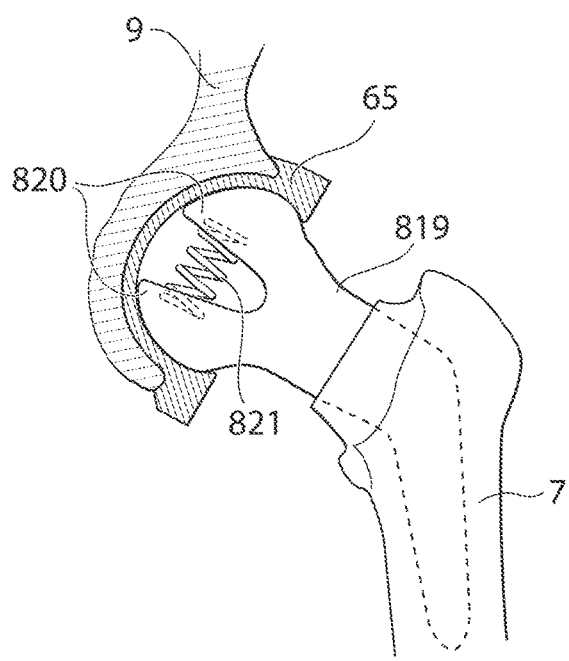
FIG. 103 shows an alternative embodiment of the medical device shown in FIG. 101.

FIG. 103 shows an embodiment of the medical device in which the elastic elements 820 are further assisted by a spring 821 in connection with two elastic elements 820, the spring 821 is compressed alongside the elastic members 820, when a pre-determined strain is placed on the prosthetic part 819 comprising the artificial caput femur.

Figure 104:
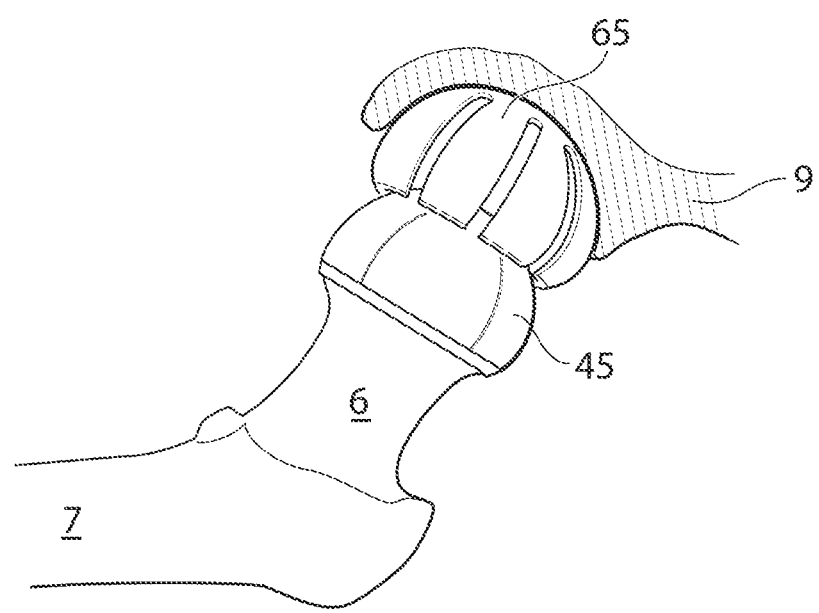
FIG. 104 shows an embodiment in which an artificial acetabulum surface has been fixated to the pelvic bone, and an artificial caput femur surface has been fixated to the caput femur.

FIG. 104 shows an artificial expandable acetabulum surface 65 being fixated in the pelvic bone 9. The artificial acetabulum surface 65 is adapted to travel beyond the maximum diameter of the caput femur 5 and thereby clasping the caput femur 5. An artificial caput femur surface 45 has been provided on the caput femur 5, the artificial caput femur passing beyond the maximum diameter of the caput femur 5 and thereby clasping the caput femur 5. The construction with surfaces passing beyond the maximum diameter of the caput femur 5 enables a stable fixation of the hip joint surfaces and reduces the risk of luxation.

A different approach to the step of providing an artificial hip joint surface will now be described. This approach comprises the steps of casting an artificial hip joint surface inside of the hip joint. These steps can be performed by means of a mould; such mould may also be using human parts such as caput femur and/or acetabulum or any of the artificial hip joint surfaces.

Figure 105:
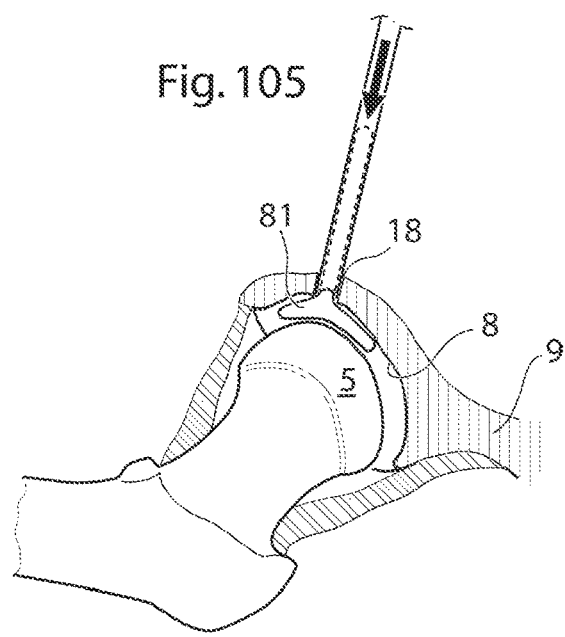
FIG. 105 shows a hip joint in section when a mould is being inserted.

FIG. 105 shows the step of placing a mould 81 inside of the hip joint of a human patient through a hole 18 in the pelvic bone 9. The step of placing said mould 81 can be performed in the surgical, or in the laparoscopic/arthroscopic method.

Figure 106A:
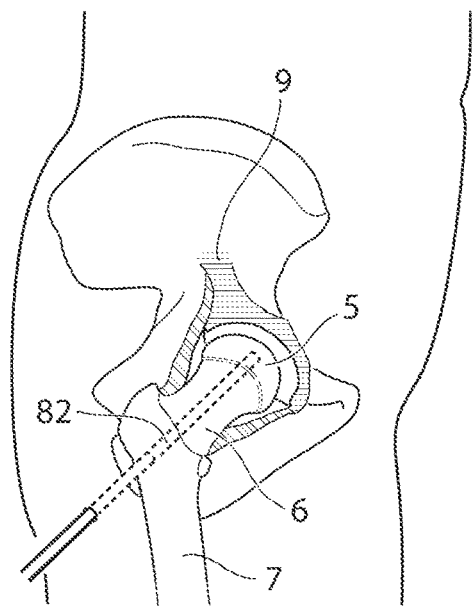
FIG. 106a shows the creation of a hole in the femoral bone.
Figure 106B:
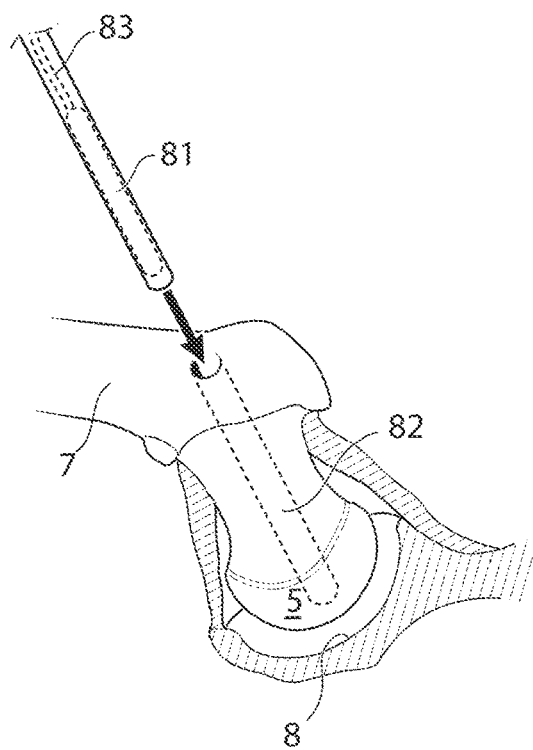
FIG. 106b shows an instrument able to introduce objects into a hip joint through the femoral bone.

FIG. 106a,b,c,d shows an alternative approach to placing said mould 81 in the hip joint of a human patient. Said alternative approach comprises the steps of creating a hole 82 in the femoral bone 7 following a length axis of the collum femur 6, said hole starting from the lateral side of the thigh, penetrating the cortex of the femoral bone 7 and eventually reaching the cortex of the caput femur 5 from the inside thereof, penetrating said cortex and entering into the hip joint. After the creation of the hole 82 in the femoral bone 7 the mould 81 is inserted into the hip joint through the hole 82 using a surgical instrument 83 adapted therefore, shown in FIG. 106b.

Figure 106C:
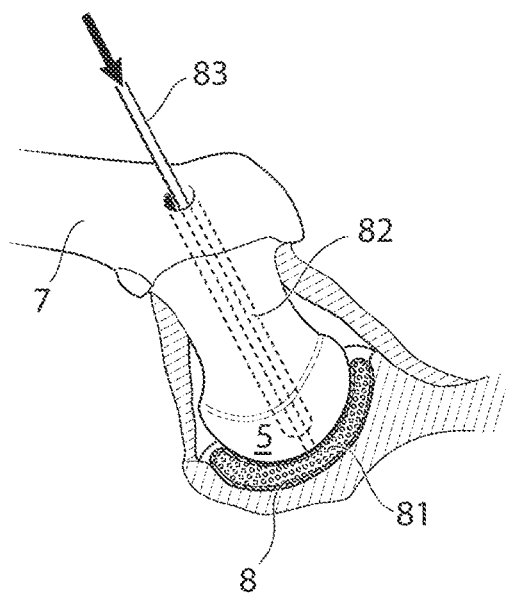
FIG. 106c shows the placing of a mould inside of the hip joint using an instrument that operates through the femoral bone.

FIG. 106c shows the mould 82 when being inserted into the hip joint using the surgical instrument 83 adapted therefore.

Figure 106D:
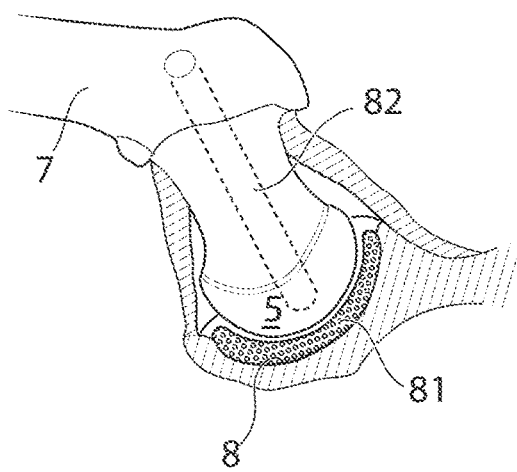
FIG. 106d shows the hip joint in section after the placing of a mould inside of the hip joint using an instrument that operates through the femoral bone.

FIG. 106d shows the mould 82 after insertion into the hip joint, the surgical instrument used to place said mould 82 in the hip joint is retracted after the insertion is completed. It is also conceivable that the hip joint surface is provided by casting the hip joint surface inside of the hip joint without the use of a mould.

Figure 107:
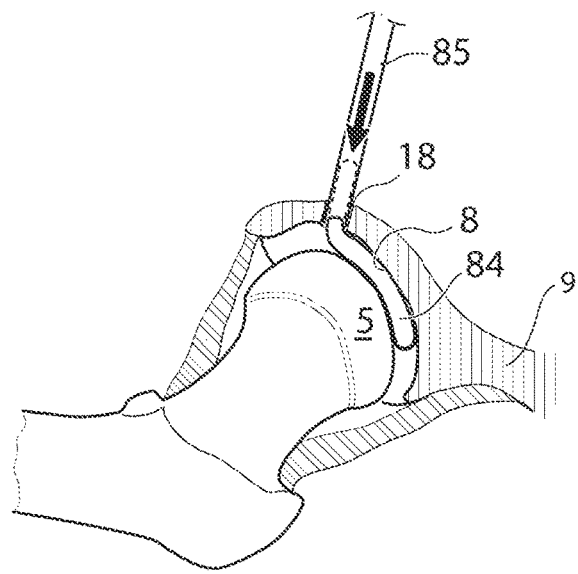
FIG. 107 shows the insertion of a first sealing member into a hip joint.

FIG. 107 shows the hip joint in section wherein a first sealing member 84 is inserted through a hole 18 in the pelvic bone 9 using an instrument adapted therefore 85. The step of placing said first sealing member 84 can be performed in the surgical, or in the laparoscopic/arthroscopic method.

Figure 108:
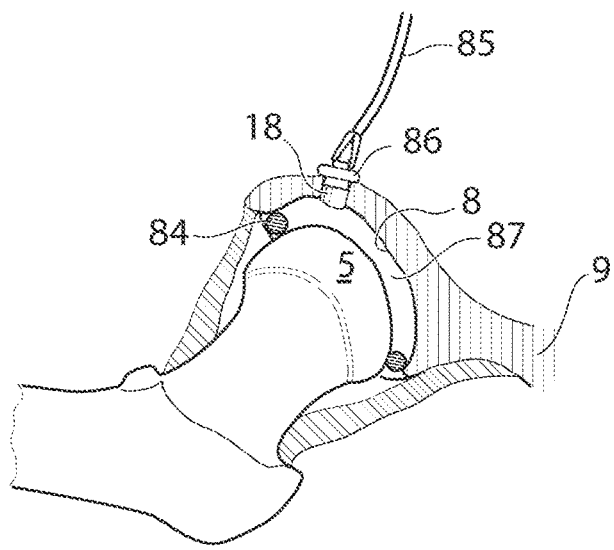
FIG. 108 shows the insertion of a second sealing member.

FIG. 108 shows the hip joint in section wherein a second sealing member 86 is inserted through the surgical or laparoscopic/arthroscopic method. The first 84 and second 86 sealing members creates a sealed space 87 between the acetabulum 8 and the caput femur 5 or one or two artificial replacements therefore, adapted to be used as a mould for providing an artificial acetabulum 65 and/or a caput femur surface 45.

Figure 109A:
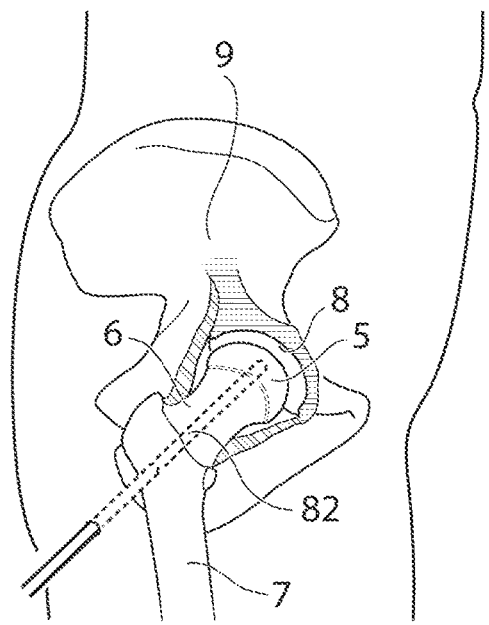
FIG. 109a shows the creation of a hole in the femoral bone.
Figure 109B:
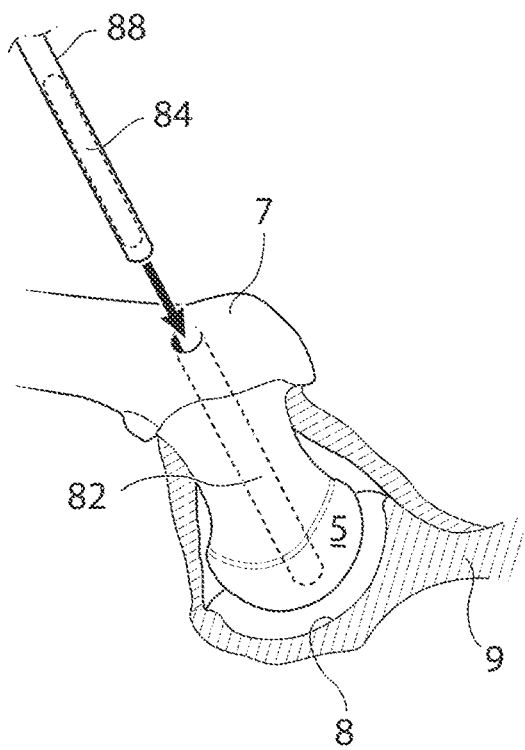
FIG. 109b shows an instrument able to introduce objects into a hip joint through the femoral bone.
Figure 109C:
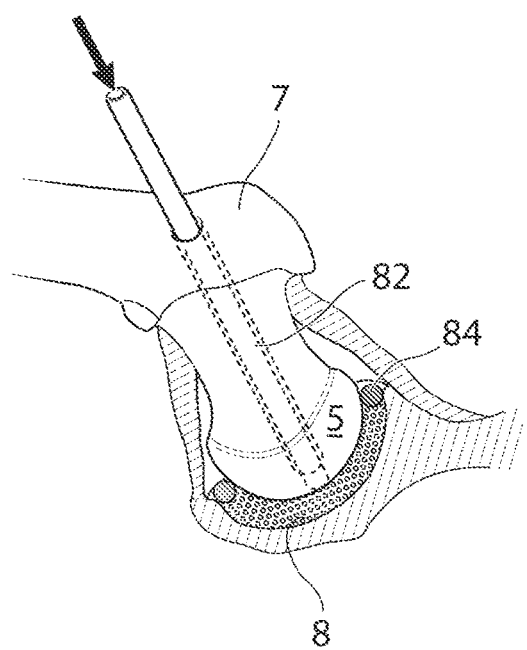
FIG. 109c shows the placing of a sealing member inside of the hip joint using an instrument that operates through the femoral bone.

FIG. 109a,b,c shows an alternative approach to placing said first sealing member 84 in the hip joint of a human patient. Said alternative approach comprises the steps of creating a hole 82 in the femoral bone 7 following a length axis of the collum femur 6, as shown in FIG. 46a, said hole starting from the lateral side of the thigh, penetrating the cortex of the femoral bone 7 and eventually reaching the cortex of the caput femur 5 from the inside thereof, penetrating said cortex and entering into the hip joint. After the creation of the hole 82 in the femoral bone 7 the first sealing member 84 is inserted into the hip joint through the hole 82 using a surgical instrument 88 adapted therefore, as shown in FIG. 109c.

Figure 110A:
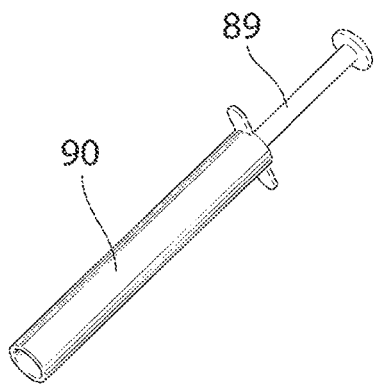
FIG. 110a shows an instrument for insertion of a mould or a sealing member into a hip joint.

FIG. 110a,b,c shows the surgical instrument adapted to insert a mould 81 and/or a first and second sealing member 84,86 into the hip joint of a human patient through a hole 18 in the pelvic bone 9 or a hole 82 in the femoral bone 9.

Figure 110B:
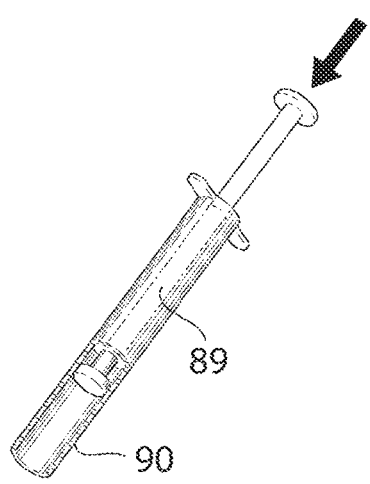
FIG. 110b shows the instrument for insertion of a mould or a sealing member into a hip joint in section.

FIG. 110b shows a section of the surgical instrument 83,85,88 comprising a tube like element for housing of the mould 81 and/or said first and second sealing members 84,86. A piston 89 used to transport said mould 81 and/or first and second sealing members 84,86 into the hip joint of a human patient is also shown.

Figure 110C:
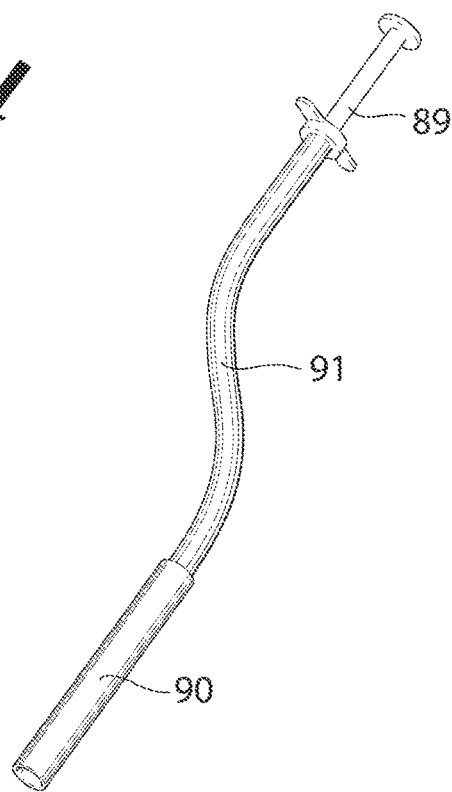
FIG. 110c shows the instrument for insertion of a mould or a sealing member into a hip joint according to a second embodiment.

FIG. 110c shows a the surgical instrument 83,85,88 adapted to insert a mould 81 and/or a first and second sealing member 84,86 into the hip joint of a human patient, the second embodiment further comprises a flexible or bent part 91 improving the reach of the surgical instrument.

After the steps of providing a mould 81 or a sealed space 87, fluid is injected into said mould 81 or into said sealed space 87 through the hole 18 in the pelvic bone 9 or the hole 82 in the femoral bone 7.

Figure 111:
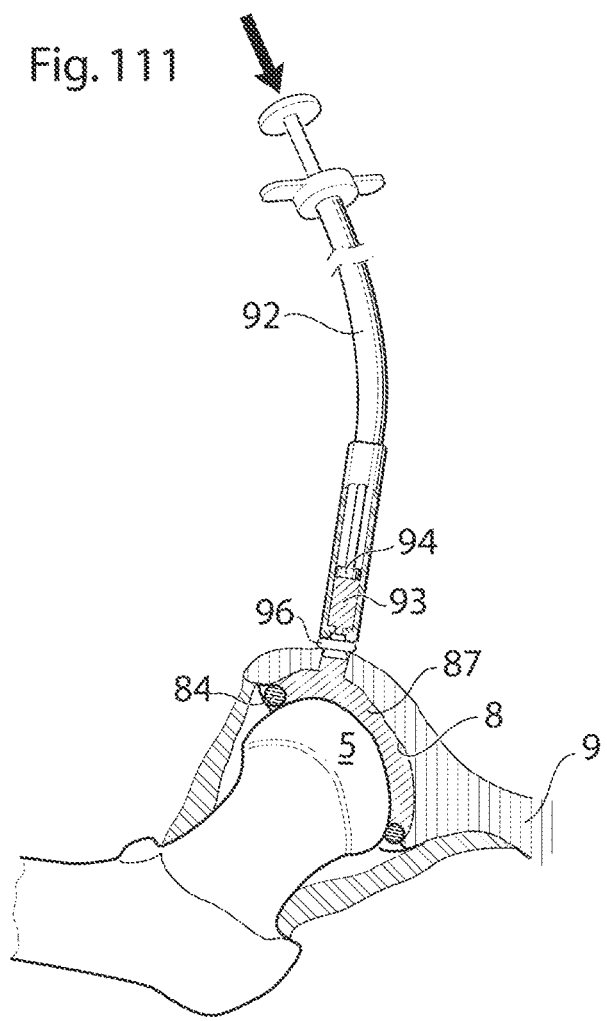
FIG. 111 shows the filling of a sealed area inside of the hip joint using an instrument that operates through the pelvic bone.

FIG. 111 shows the hip joint in section wherein an injecting member 92 injects a fluid 93 into a sealed area 87 in the hip joint through a hole 18 in the pelvic bone 9 from the opposite side from acetabulum 8. Said sealed area 87, is sealed by a first 84 and second 86 sealing member. The injecting member 92 comprises a piston 94 that pushes said fluid 93 into the sealed area 87.

Figure 112:
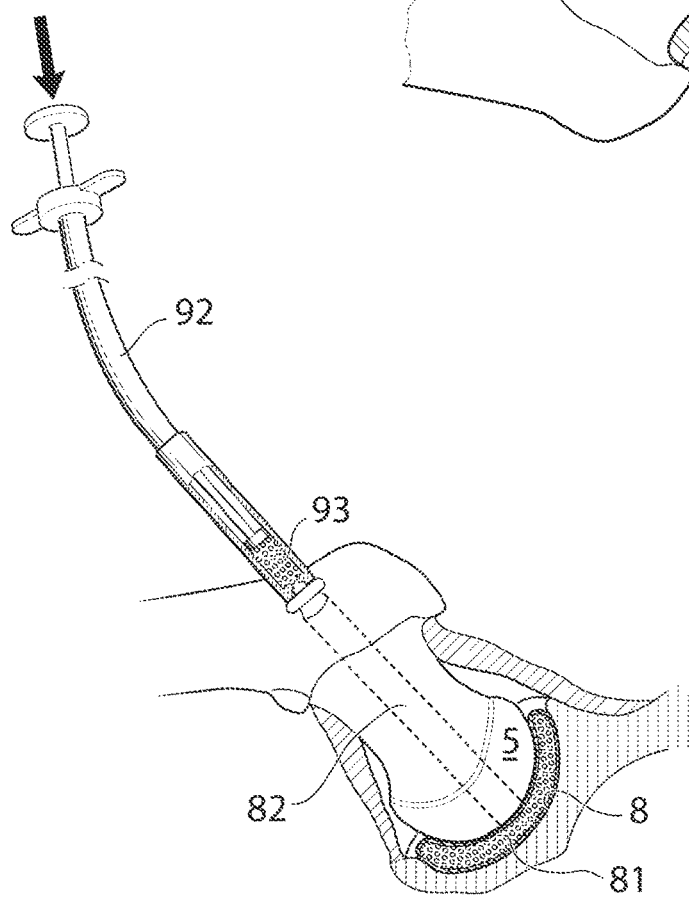
FIG. 112 shows the filling of a mould inside of the hip joint using an instrument that operates through the femoral bone.

FIG. 112 shows the hip joint in section wherein an injecting member 92 injects a fluid 93 into a mould 81 in the hip joint through a hole 82 in the femoral bone 7. The injecting member 92 comprises a piston 94 that pushes said fluid 93 into the mould 81.

Figure 113:
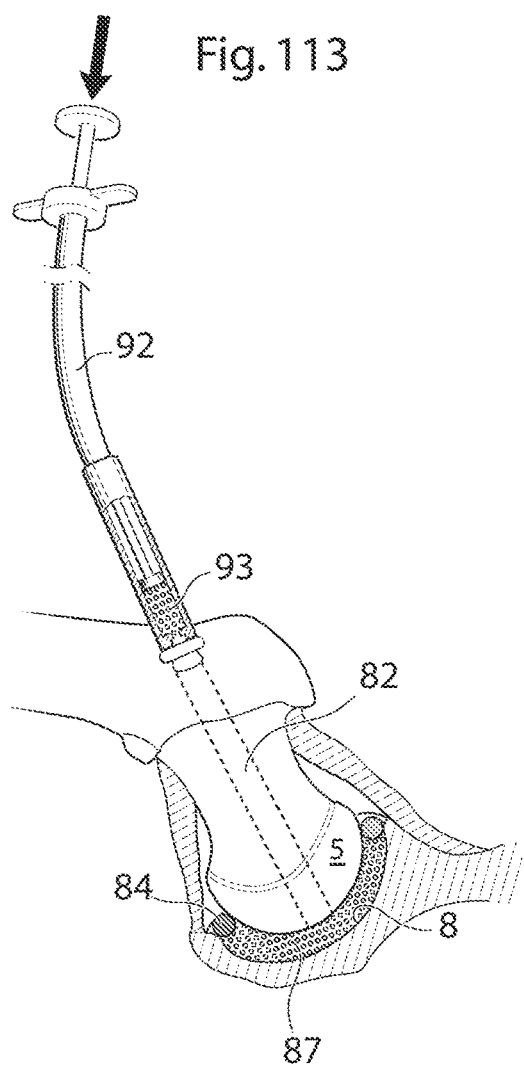
FIG. 113 shows the filling of a sealed area inside of the hip joint using an instrument that operates through the femoral bone.

FIG. 113 shows the hip joint in section wherein an injecting member 92 injects a fluid 93 into a sealed area 87 in the hip joint through a hole 82 in the femoral bone 7. The sealed area 87 is sealed by at least a first 84 sealing member. The injecting member 92 comprises a piston 94 that pushes said fluid 93 into the sealed area 87.

Figure 114:
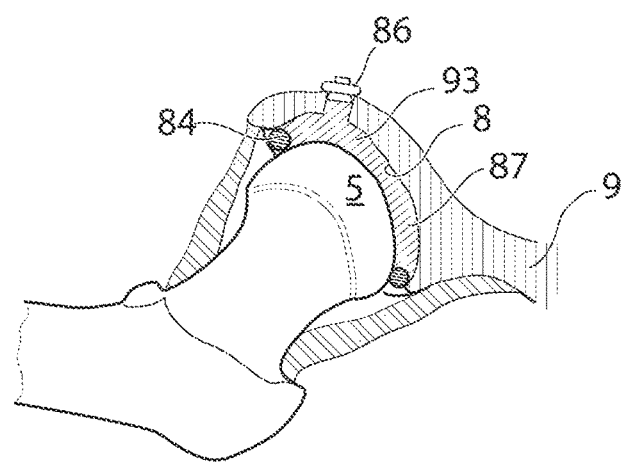
FIG. 114 shows a hip joint in section after a sealed area in the hip joint has been filled with a fluid.

FIG. 114 shows the sealed area 87, sealed by the first 84 and second 86 sealing member together with the caput femur 5 and the pelvic bone 9. A fluid adapted to harden 93 has been injected into said sealed area, and after the hardening of said fluid it provides at least one hip joint surface.

Figure 115:
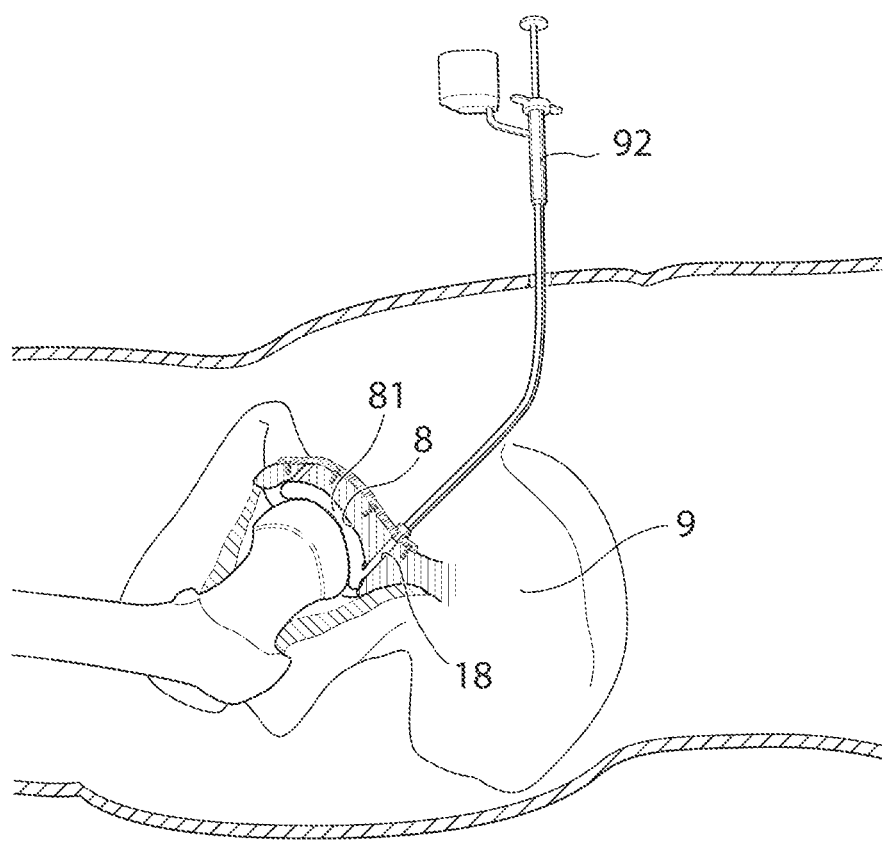
FIG. 115 shows the insertion of fluid into an area of the hip joint.

FIG. 115 shows a lateral section of the human body wherein an injecting member 92 injects a fluid into a mould 81 in the hip joint through a hole 18 in the pelvic bone 9 from the opposite side from acetabulum 8.

After the injecting member 92 has injected a fluid 93 into a mould 81 or a sealed are 87 it is being retracted from the area.

The mould 81 and the first and second sealing members 84,86 according to any of the embodiments can further be adapted to be resorbable by the human body or to melt after they have served their purpose.

After at least one hip joint surface has been provided through a hole 18 in the pelvic bone 9, in accordance with any of the embodiment above, said hole 18 needs to be closed. All embodiments described above related to a mould or molding or injecting, injecting also by human tissue created space or any instruments related to any method above may also be used inserting any part through the hip joint capsule. Both the first and second sealing member may be inserted that way.

Figure 116:
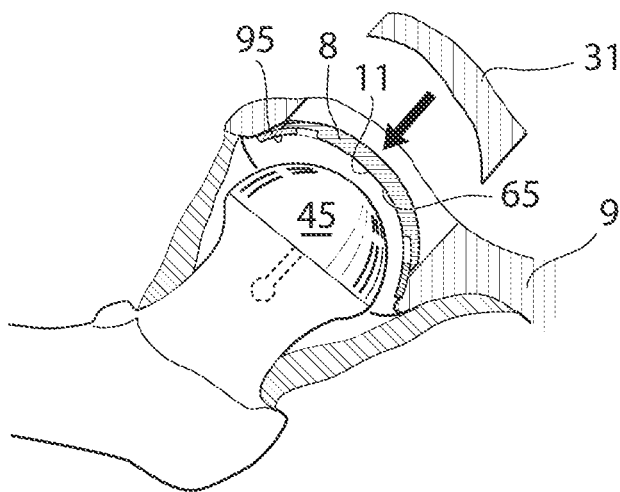
FIG. 116 shows the closing of a hole in the hip joint using a bone plug.

FIG. 116 shows the hip joint of a human patient in section wherein a bone plug 31 is placed in the hole 18 in the pelvic bone 9 to close said hole 18. According to a first embodiment the artificial acetabulum surface 65 comprises supporting members 94 which carries the load placed on the acetabulum 8 from weight of the human patient through the contact with the caput femur 5. Said supporting members can be adapted to be displaceable 97 supporting members. The bone plug 31 can be attached to the artificial acetabulum surface 11 and/or the pelvic bone 9 by means of bone cement, adhesive, at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 117:
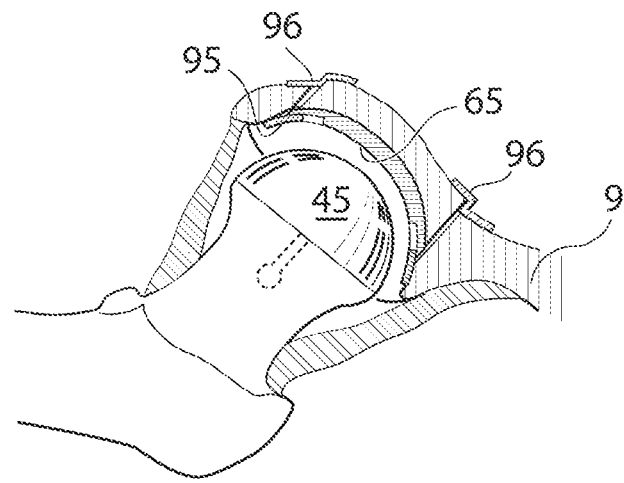
FIG. 117 shows the fixation of a bone plug in the pelvic bone.

FIG. 117 shows the hip joint of a human patient in section wherein the bone plug 31 placed in the hole 18 in the pelvic bone 9 is further supported by supporting means 96 placed between the bone plug 31 and the pelvic bone 9 on the opposite side from acetabulum 8 using at lest one of: bone cement, adhesive, at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 118:
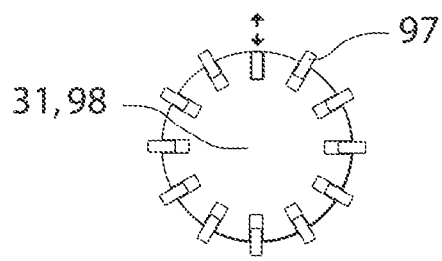
FIG. 118 shows a part for closing a hole in the pelvic bone having displaceable supporting members.

FIG. 118 shows a bone plug 31 or a prosthetic part 98 comprising several displaceable supporting members adapted to carry the load placed on the acetabulum 8 from weight of the human patient through the contact with the caput femur 5. The displaceable parts 97 are displaced into a corresponding part in or at the edge of the hole 18 in the pelvic bone 9. According to a second embodiment the closing of the hole 18 in the pelvic bone is done by means of a prosthetic part 98.

Figure 119A:
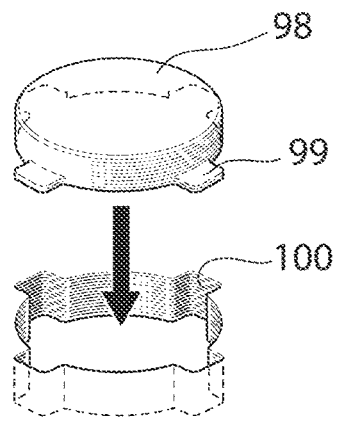
FIG. 119a shows a prosthetic part being used to close a hole in the pelvic bone.

FIG. 119a shows the prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

Figure 119B:
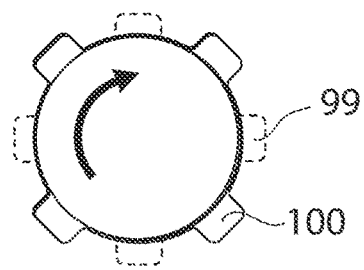
FIG. 119b shows how sections of a prosthetic part is used as support against the edges of the hole in the pelvic bone.

FIG. 119b shows the prosthetic part 98 when rotated to carry the load placed on the acetabulum 8 from weight of the human patient through the contact with the caput femur 5. This supporting means could be constructed in many different ways and this should be seen as examples.

Figure 119C:
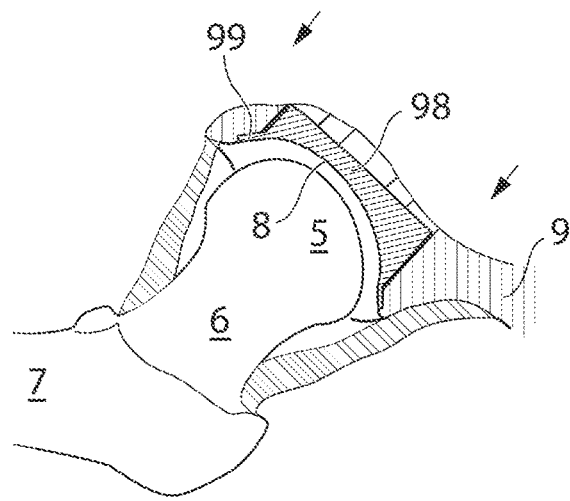
FIG. 119c shows the insertion of a prosthetic part in the hole in the pelvic bone.

FIG. 119c shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Figure 120:
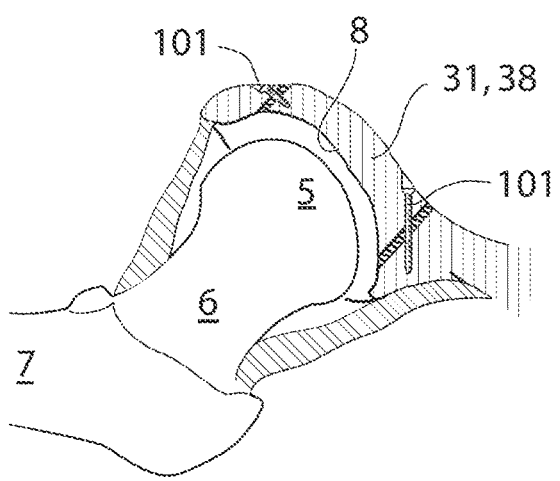
FIG. 120 shows how screws are being used to fixate a bone plug or a prosthetic part in the hole in the pelvic bone of a human patient.
Figure 121:
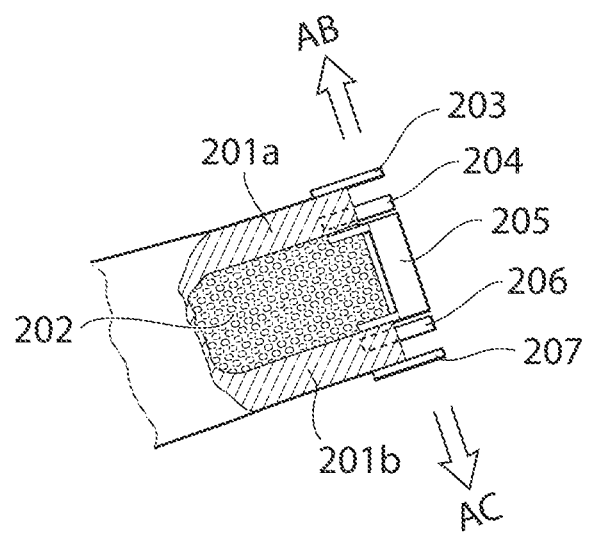
FIG. 121 shows a cross-sectional view of the pelvic bone.

FIG. 120 shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support. This construction may be performed in many different ways for FIG. 121 is a schematic figure of the pelvic bone in section. The pelvic bone comprises an inner cortex 201a placed on the abdominal side of the pelvic bone AB, and an outer cortex 201b placed on the acetabulum side of the pelvic bone AC. The inner and outer cortex 201a,b comprises cortical bone, which is a more dense sclerotic bone. The pelvic bone further comprises cancellous bone 202, placed in the bone marrow between said inner cortex 201a and said outer cortex 201b. The supporting members of the medical device according to any of the embodiments above can be adapted to be in contact with the outside of the inner cortex 201a as supporting member 203, or be placed inside of the inner cortex 201a as supporting member 204, which enables the supporting member to carry loads in the direction of the abdomen AB as well as in the direction of the acetabulum AC. It is furthermore conceivable that the supporting member is placed in the middle of the inner cortex 201a and the outer cortex 201b, in the cancellous bone, as supporting member 205, in which case the supporting member could be in contact with the inner cortex 201a, on the inside thereof, and the outer cortex 201b, on the inside thereof, which enables the supporting member to carry loads in the direction of the abdomen AB as well as in the direction of the acetabulum AC. Further, the supporting members can be adapted to be in contact with the outside of the outer cortex 201b as supporting member 207, or be placed inside of the outer cortex 201b as supporting member 206, which enables the supporting member to carry loads in the direction of the abdomen AB as well as in the direction of the acetabulum AC.

Figure 122A:
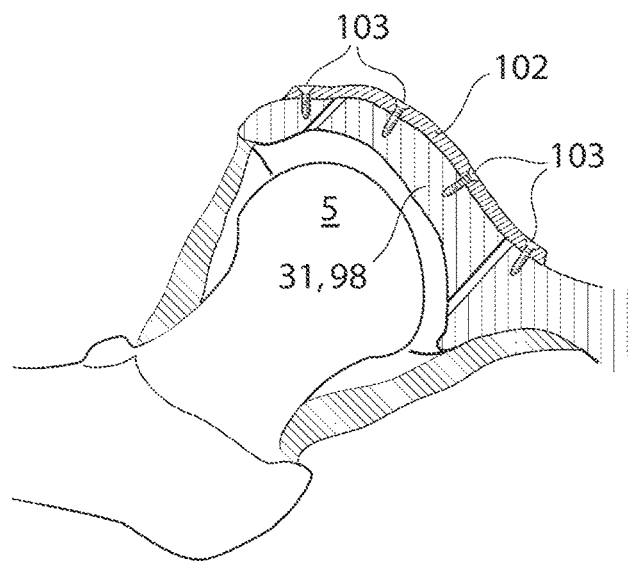
FIG. 122a shows how a supporting plate is being used to fixate a bone plug or a prosthetic part in the hole in the pelvic bone of a human patient.

FIG. 122a shows the hip joint of a human patient in section wherein bone plug 31 or prosthetic part 98 is attached to the pelvic bone 9 by means of a plate 102 at least partly covering said bone plug 31 or prosthetic part 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

Figure 122B:
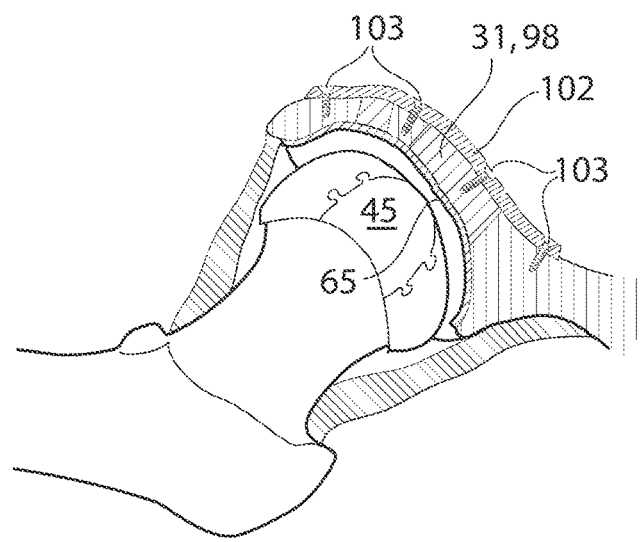
FIG. 122b shows two bone plugs or prosthetic parts being fixated using a supporting plate.

FIG. 122b shows the hip joint of a human patient in section wherein two bone plugs 31 or prosthetic parts 98 are attached to the pelvic bone 9 by means of a plate 102 at least partly covering said bone plugs 31 or prosthetic parts 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 122b also shows the provided artificial acetabulum surface 65.

Figure 122C:
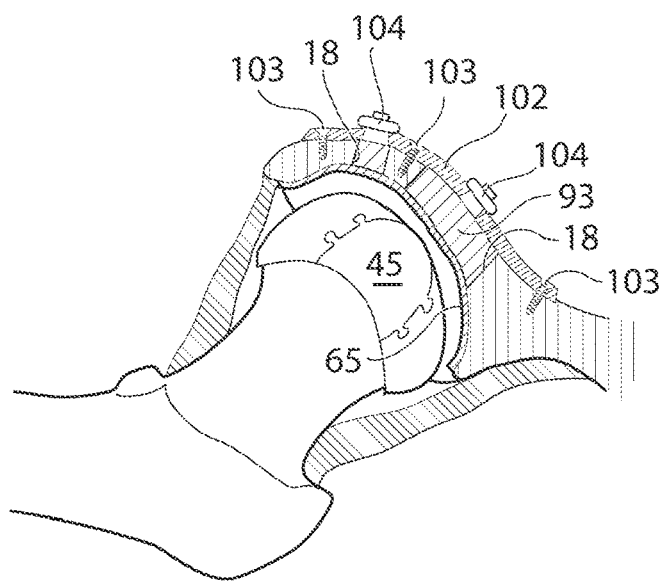
FIG. 122c shows a section of the hip joint after two holes in the pelvic bone have been filled with a fluid.

FIG. 122c shows the hip joint of a human patient in section wherein two holes 18 in the pelvic bone has been covered by means of a fluid injected into said holes 18, through sealing members 104, said fluid 93 being adapted to harden. Furthermore a plate 102 has been provided at least partly covering said holes 18. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 122c also shows the provided artificial acetabulum surface 65, and the provided artificial caput femur surface 45.

Figure 123A:
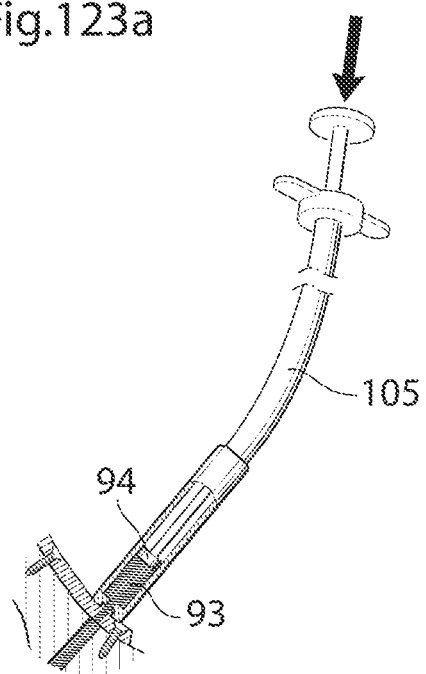
FIG. 123a shows an injecting member adapted to inject a fluid into an area of the hip joint.

FIG. 123a shows an injecting member 105 for injecting a fluid adapted to harden 93, preferably bone cement or adhesive to be used as support in the closing of the hole 18 in the pelvic bone 9. The injecting member 105 comprises a piston 94 that pushes said fluid 93 the area where it is wanted.

Figure 123B:
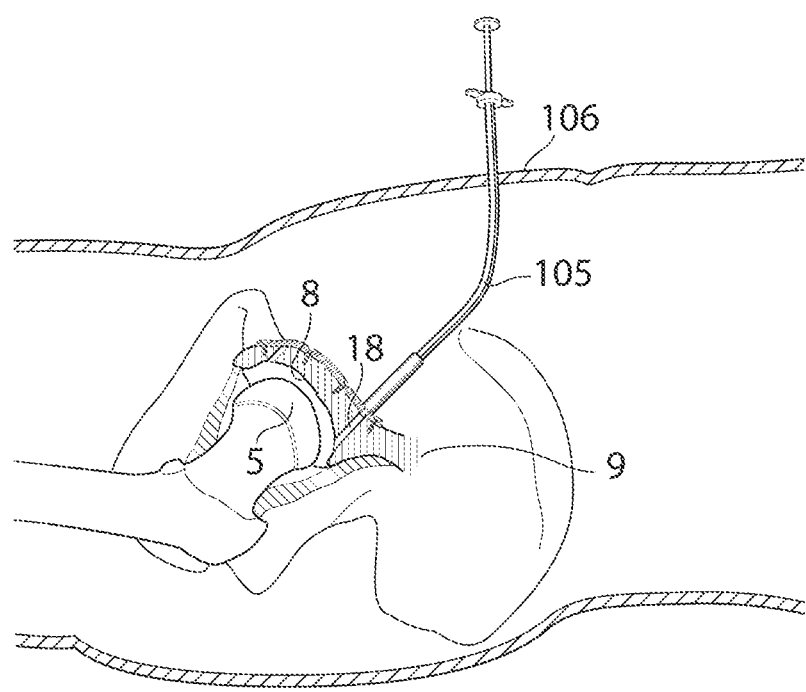
FIG. 123b shows an injecting member adapted to inject a fluid into an area of the hip joint when injecting a fluid.

FIG. 123b shows the injecting member 105 as it is inserted through the skin 106 of a human patient in the surgical or laparoscopic/arthroscopic method, and is further placed in connection with the hip joint through the hole 18 in the pelvic bone 9. The injecting member 105 is adapted to inject a fluid 93 adapted to harden.

Figure 124:
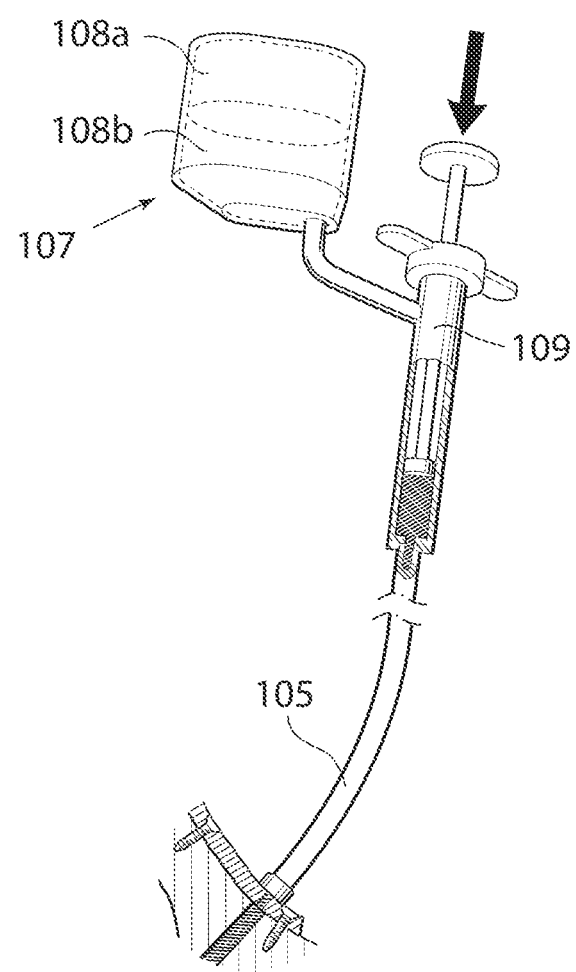
FIG. 124 shows an injecting member in further detail.

FIG. 124 shows the injecting member 105 according to any of the embodiments above, adapted to inject fluid 93 into a mould 81, a sealed area 87 or a connecting area between the pelvic bone 9 and a prosthetic part, the pelvic bone 9 and a bone plug 31 or the caput femur 5 and a prosthetic part. Said injecting member 105 comprises a container 107 adapted to hold a fluid for injection. According to a first embodiment said container 107 comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) a container is adapted to keep said fluid sterile. According to a third embodiment (not shown) a container is adapted to keep said fluid cold and according to a fourth embodiment (not shown) a container is adapted to keep said fluid in a dark environment. Furthermore a combination of the above mentioned embodiments is conceivable.

After the step of closing the hole in the pelvic bone of the human patient is concluded all instruments are retracted and the final step of the surgical or laparoscopic/arthroscopic method is performed. The final step comprises suturing or stapling the affected tissue and finally suturing or stapling the skin of the human patient.

Figure 125A:
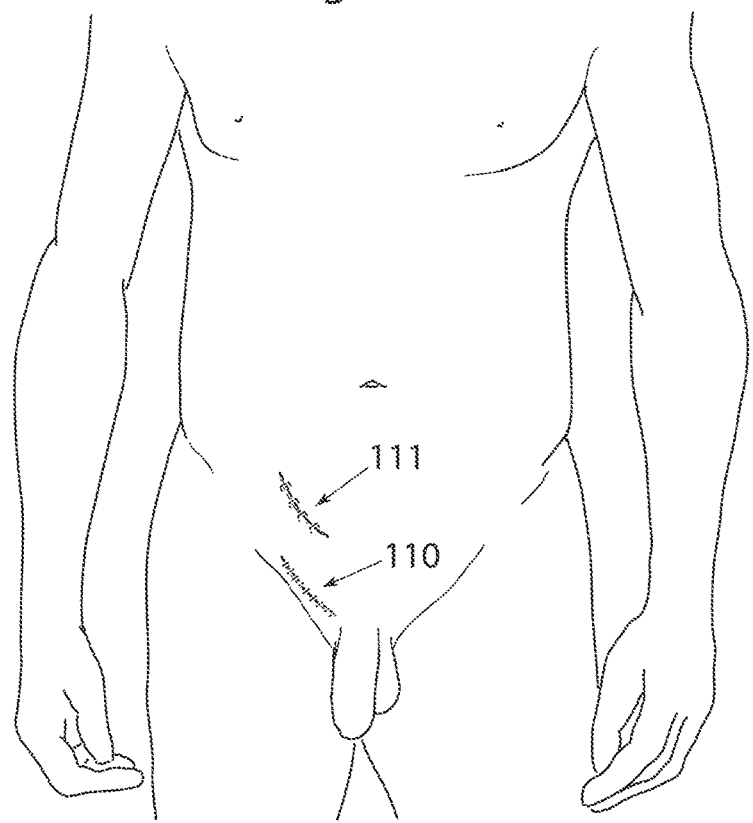
FIG. 125a shows the step of suturing or stapling in the surgical method.
Figure 125B:
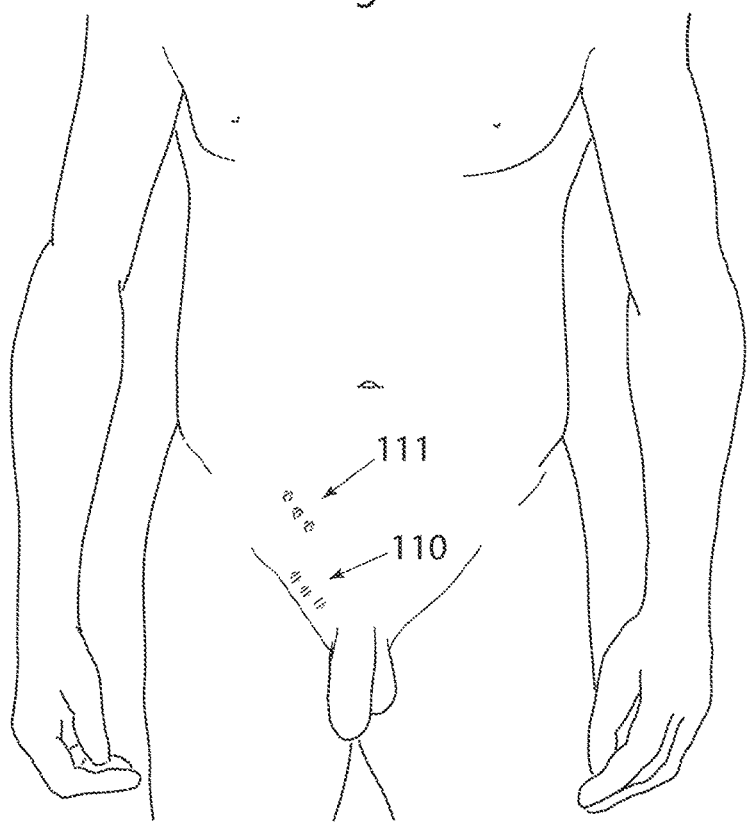
FIG. 125b shows the step of suturing or stapling in the laparoscopic/arthroscopic method.

FIG. 125a shows the step of suturing 110 or stapling 111 the skin 106 of the human patient in the surgical method, whereas FIG. 125b shows the step of suturing 110 or stapling 111 the skin 106 of the human patient in the laparoscopic/arthroscopic method. The laparoscopic/arthroscopic method may not need any suturing.

Figure 126:
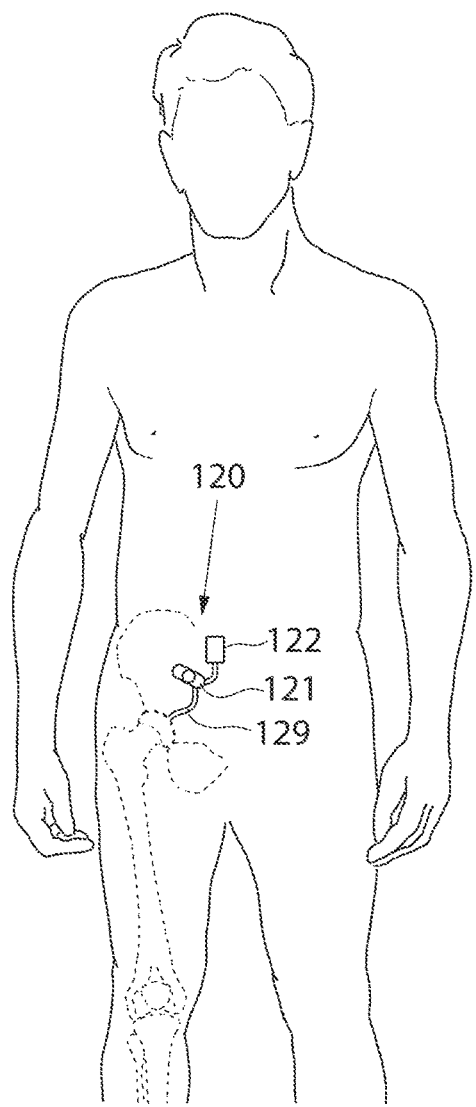
FIG. 126 shows a frontal view of a patient when a lubricating system is provided.

FIG. 126 shows the human patient in a frontal view when an implantable lubrication system 120 has been implanted. The implantable lubrication system 120 is adapted to inject a lubricating fluid continuously, intermittently or when needed into said hip joint. According to the embodiment shown in FIG. 126 the implantable lubricating system comprises two interconnected units 121, 122. The two interconnected units are placed in the abdominal region of the human patient and is in connection with the hip joint through a fluid transferring member 129.

Figure 127:
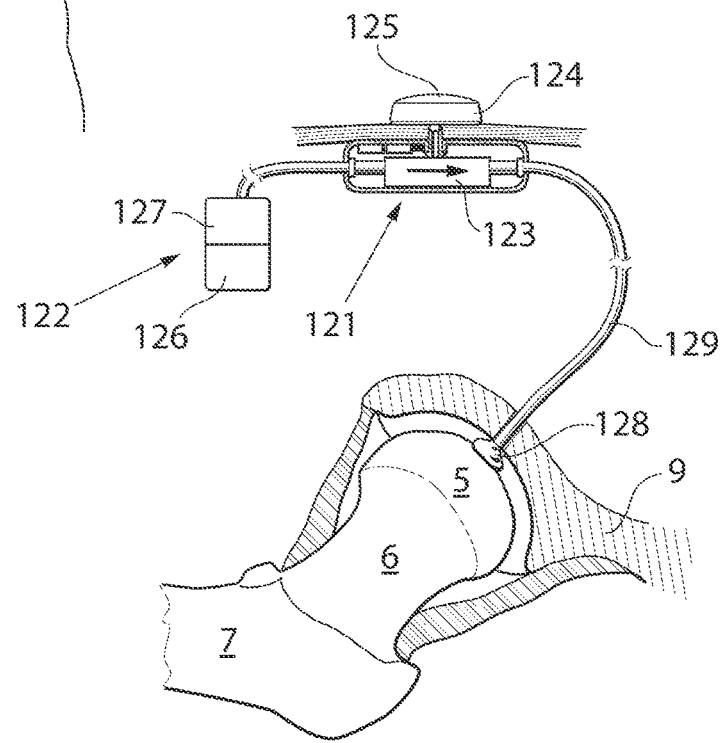
FIG. 127 shows the hip joint and lubricating system in further detail.

FIG. 127 shows the implantable lubricating system 120 in further detail, According to the embodiment shown the implantable lubricating system comprises a first unit 121 comprising a pumping member 123 adapted to pump the lubricating fluid from a reservoir 127 to an area of the hip joint. The first unit 121 furthermore comprises an injection port 125 for filling the reservoir 127 from outside of the human body without having to perform a surgical procedure. The injection port 125 comprises a self-sealing membrane which is penetratable with a needle attached to a syringe. The first unit 121 further comprises a receiver of wireless energy 124 preferably comprising a coil. Said receiver of wireless energy is used to charge a battery 126. According to this embodiment the implantable lubrication system 120 further comprises a second unit 122 which in turn comprises a battery 126 and a fluid reservoir 127. The lubricating fluid 128 is pumped from the reservoir, through the first unit 121 with the pumping device, through the fluid transferring member 129 and into the area of the hip joint where it helps lubricating the hip joint surfaces. The lubricating fluid is preferably a biocompatible lubricating fluid such as hyaluronic acid.

Figure 128:
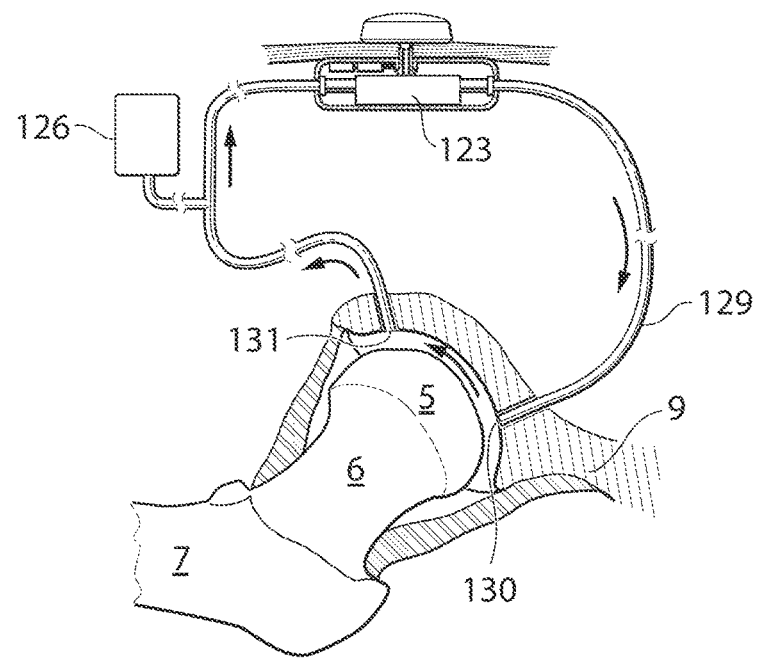
FIG. 128 shows a circling lubricating system.

FIG. 128 shows the implantable lubricating system according to an embodiment wherein the implantable lubricating system is a circulating lubricating system comprising one inlet 130 into the joint to be lubricated and one outlet 131. Preferably this system is a system for continuous lubrication where the pumping member 123 continuously circulates the lubricating fluid 128 inside of the hip joint.

Figure 129:
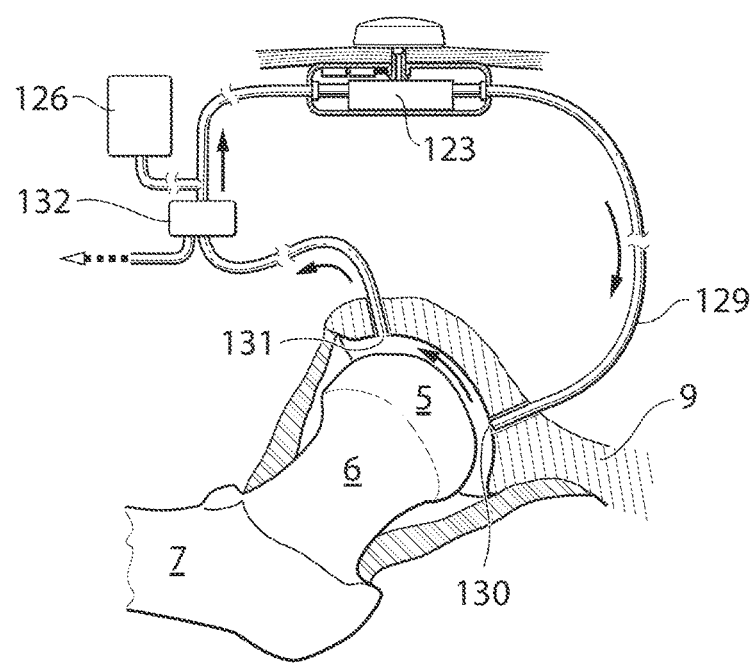
FIG. 129 shows a circling lubricating system, with filter.

FIG. 129 shows an implantable lubricating system for circulating lubrication wherein the lubricating system further comprises a filtering member 132 for filtering the lubricating fluid. The filter is adapted to be self cleaning and the out filtered matter is disposed through the disposal channel 133, either into the abdomen of the human patient, or into a container attached to the disposal channel 133. Through the filtering of the lubricating fluid 128 the circulating lubricating system can operate for long periods without the need of any surgical procedures.

Please note that any embodiment or part of embodiment as well as any method or part of method could be combined in any way. All examples herein should be seen as part of the general description and therefore possible to combine in any way in general terms.

The invention claimed is:

1. A method of treating a hip joint of a human patient by providing a medical device comprising at least one partly ball or bowl shaped artificial hip joint surface adapted to replace at least one hip joint surface in a functional hip joint, said hip joint comprising a caput femur and an acetabulum, said method comprising the steps of:
   inserting a needle or a tube like instrument into the patient's body,
   using the needle or tube like instrument to fill a part of the patient's body with gas and thereby expanding a cavity within said body,
   placing at least two laparoscopic/arthroscopic trocars in said cavity,
   inserting a camera through one of the laparoscopic/arthroscopic trocars into said cavity,
   inserting at least one dissecting tool through one of said at least two laparoscopic/arthroscopic trocars,
   dissecting an area of the pelvic bone on the opposite side from the acetabulum,
   creating a hole in said dissected area, said hole passing through the pelvic bone and into said hip joint of the patient, and
   providing said medical device to the hip joint, through said hole in the pelvic bone of the patient.

2. The method according to claim 1, wherein said medical device comprising an artificial caput femur.

3. The method according to claim 1, further comprising the step of reaming the caput femur.

4. The method according to claim 1, further comprising the step of fixating said hip joint surface to the caput femur or to the acetabulum.

5. The method of treating a hip joint of a human patient according to claim 4, wherein said fixation is performed by means of mechanical fixating members, bone cement or adhesive.

6. The method according to claim 1, further comprising the step of closing said hole.

7. The method according to claim 6, wherein said hole is placed in the pelvic bone, wherein said closing of said hole in the pelvic bone is performed by means of a prosthetic part.

8. The method according to claim 1, further comprising the step of placing a mould inside of the hip joint.

9. The method according to claim 8, further comprising the step of injecting a fluid into said mould placed inside of the hip joint of the human patient.

10. The method according to claim 1, further comprising the steps of:
    placing at least one sealing member between the acetabulum and the caput femur, thus creating a sealed area between the acetabulum and the caput femur, and
    injecting a fluid into said sealed area.

11. A method of treating a hip joint of a human patient by providing a medical device comprising at least one partly ball or bowl shaped artificial hip joint surface adapted to replace at least one hip joint surface in a functional hip joint, said hip joint comprising a caput femur and an acetabulum, said method comprising the steps of:
    cutting the skin of the patient,
    dissecting an area of the pelvic bone on the opposite side from the acetabulum,
    creating a hole in said dissected area, said hole passing through the pelvic bone and into the hip joint of the patient, and
    providing said medical device to the hip joint, through said hole in the pelvic bone of the patient,
wherein said medical device comprises an artificial caput femur.

12. The method according to claim 11, further comprising the step of reaming the caput femur.

13. The method according to claim 11, further comprising the step of fixating said hip joint surface to the caput femur or to the acetabulum.

14. The method of treating a hip joint of a human patient according to claim 13, wherein said fixation is performed by means of mechanical fixating members, bone cement or adhesive.

15. The method according to claim 11, further comprising the step of closing said hole.

16. The method according to claim 15, wherein said hole is placed in the pelvic bone, wherein said closing of said hole in the pelvic bone is performed by means of a prosthetic part.

17. The method according to claim 11, further comprising the step of placing a mould inside of the hip joint.

18. The method according to claim 17, further comprising the step of injecting a fluid into said mould placed inside of the hip joint of the human patient.

19. The method according to claim 11, further comprising the steps of:
    placing at least one sealing member between the acetabulum and the caput femur, thus creating a sealed area between the acetabulum and the caput femur, and
    injecting a fluid into said sealed area.

* * * * *